US012150713B2

(12) United States Patent
Saeidi et al.

(10) Patent No.: US 12,150,713 B2
(45) Date of Patent: Nov. 26, 2024

(54) CONFIDENCE-BASED ROBOTICALLY-ASSISTED SURGERY SYSTEM

(71) Applicants: University of Maryland, College Park, College Park, MD (US); The Johns Hopkins University, Baltimore, MD (US); Children's National Medical Center, Washington, DC (US)

(72) Inventors: Hamed Saeidi, College Park, MD (US); Axel Krieger, Alexandria, VA (US); Simon Leonard, State College, PA (US); Justin Opfermann, Washington, DC (US); Michael Kam, Greenbelt, MD (US)

(73) Assignees: UNIVERSITY OF MARYLAND, COLLEGE PARK, College Park, MD (US); THE JOHNS HOPKINS UNIVERSITY, Baltimore, MD (US); CHILDREN'S NATIONAL MEDICAL CENTER, Washington, DC (US)

( * ) Notice: Subject to any disclaimer, the term of this patent is extended or adjusted under 35 U.S.C. 154(b) by 892 days.

(21) Appl. No.: 17/098,990

(22) Filed: Nov. 16, 2020

(65) Prior Publication Data
US 2021/0077195 A1 Mar. 18, 2021

Related U.S. Application Data

(63) Continuation of application No. PCT/US2020/033270, filed on May 15, 2020, which
(Continued)

(51) Int. Cl.
*A61B 34/10* (2016.01)
*A61B 18/14* (2006.01)
(Continued)

(52) U.S. Cl.
CPC .............. *A61B 34/10* (2016.02); *A61B 18/14* (2013.01); *A61B 34/25* (2016.02); *A61B 34/32* (2016.02);
(Continued)

(58) Field of Classification Search
CPC ..... A61B 34/32; A61B 34/10; A61B 18/1477; A61B 34/25; A61B 18/14; A61B 90/39;
(Continued)

(56) References Cited

U.S. PATENT DOCUMENTS

| 4,604,787 A | * | 8/1986 | Silvers, Jr. ............. B23Q 7/046 |
| | | | 414/730 |
| 5,111,590 A | | 5/1992 | Park |

(Continued)

FOREIGN PATENT DOCUMENTS

| WO | 2012018816 A2 | 2/2012 |
| WO | 2014005139 A2 | 1/2014 |

(Continued)

OTHER PUBLICATIONS

Alemzadeh, H. et al., Adverse Events in Robotic Surgery: A Retrospective Study of 14 Years of FDA Data, PLoS ONE, 2016, 11(4):e0151470, pp. 1-20.

(Continued)

*Primary Examiner* — Congvan Tran
(74) *Attorney, Agent, or Firm* — Quarles & Brady LLP

(57) ABSTRACT

The present disclosure provides a system and method for controlling an articulating member including a tool. The system may include a dual camera system that captures near-infrared (NIR) images and point cloud images of a tissue or other substance that includes NIR markers. The system may generate a three-dimensional (3D) path based on identified positions of the NIR markers, may filter the generated path, and may generate a 3D trajectory for con-
(Continued)

trolling the articulated arm of a robot having a tool to create an incision along the filtered path. In a shared control mode, an operator may generate manually control commands for the robot to guide the tool along such a path, while automated control commands are generated in parallel. One or more allocation functions may be calculated based on calculated manual and automated error models, and shared control signals may be generated based on the allocation functions.

20 Claims, 42 Drawing Sheets

Related U.S. Application Data is a continuation-in-part of application No. PCT/US2019/032635, filed on May 16, 2019.

(60) Provisional application No. 62/907,872, filed on Sep. 30, 2019, provisional application No. 62/848,979, filed on May 16, 2019, provisional application No. 62/672,485, filed on May 16, 2018.

(51) Int. Cl.
  A61B 34/00     (2016.01)
  A61B 34/32     (2016.01)
  A61B 90/00     (2016.01)
  A61B 18/00     (2006.01)
  A61B 18/16     (2006.01)

(52) U.S. Cl.
  CPC .... *A61B 90/39* (2016.02); *A61B 2018/00595* (2013.01); *A61B 18/16* (2013.01); *A61B 2034/107* (2016.02); *A61B 34/76* (2016.02); *A61B 2090/371* (2016.02); *A61B 2090/3979* (2016.02)

(58) Field of Classification Search
  CPC .............. A61B 90/13; A61B 2090/371; A61B 2090/3979; A61B 34/76; A61B 18/16; A61B 34/37; A61B 2018/00595; A61B 2034/107
  See application file for complete search history.

(56) References Cited

U.S. PATENT DOCUMENTS

| | | | |
|---|---|---|---|
| 6,325,808 B1 | 12/2001 | Bernard et al. | |
| 7,164,968 B2 | 1/2007 | Treat et al. | |
| 7,831,292 B2 | 11/2010 | Quaid et al. | |
| 8,718,372 B2* | 5/2014 | Holeva | G06T 7/20 382/181 |
| 9,220,570 B2 | 12/2015 | Kim et al. | |
| 9,788,903 B2 | 10/2017 | Kim et al. | |
| 9,805,306 B1 | 10/2017 | Bataller et al. | |
| 10,864,640 B1* | 12/2020 | Innes | B08B 9/0933 |
| 2005/0154295 A1 | 7/2005 | Quistgaard et al. | |
| 2009/0326713 A1 | 12/2009 | Moriya | |
| 2011/0202068 A1 | 8/2011 | Diolaiti et al. | |
| 2014/0039517 A1 | 2/2014 | Bowling et al. | |
| 2015/0223683 A1* | 8/2015 | Davidovics | A61B 3/152 351/210 |
| 2016/0000631 A1 | 1/2016 | Becker | |
| 2016/0058517 A1 | 3/2016 | Kim et al. | |
| 2016/0161444 A1 | 6/2016 | Shimizu et al. | |
| 2017/0249844 A1 | 8/2017 | Perkins et al. | |
| 2018/0193099 A1 | 7/2018 | Kim et al. | |
| 2019/0001380 A1* | 1/2019 | Amaiwa | B29C 33/72 |
| 2021/0315637 A1 | 10/2021 | Ida et al. | |
| 2022/0383531 A1 | 12/2022 | Santini et al. | |
| 2023/0054209 A1 | 2/2023 | Roh et al. | |

FOREIGN PATENT DOCUMENTS

| | | |
|---|---|---|
| WO | 2014121262 A2 | 8/2014 |
| WO | 2018209042 A2 | 11/2018 |

OTHER PUBLICATIONS

Alexa, M. et al., Computing and Rendering Point Set Surfaces, IEEE TVCG, 2003, 9(1):1-12.
Anderson, C. et al., A Meta-Analysis of Margin Size and Local Recurrence in Oral Squamous Cell Carcinoma, Oral Oncology, 2015, 51(5):464-469.
Bargar, W. et al., Primary and Revision Total Hip Replacement Using the Robodoc(R) System, Clinical Orthopaedics and Related Research, 1998, 354:82-91.
Baumhauer, M. et al., Navigation in Endoscopic Soft Tissue Surgery: Perspectives and Limitations, Journal of Endourology, 2008, 22(4):751-766.
Beck, F. et al., tuw_checkerboard, http://wiki.ros.org/tuw_checkerboard, Version dated Oct. 20, 2018, Accessed online at https://web.archive.org/web/20181020082321/http://wiki.ros.org/tuw_checkerboard, 3 pages.
Bodner, J. et al., First Experiences with the da Vinci(TM) Operating Robot in Thoracic Surgery, European Journal of Cardio-Thoracic Surgery, 2004, 25(5):844-851.
Colas, F. et al., 3D Path Planning and Execution for Search and Rescue Ground Robots, IEEE/RSJ Int. Conf. on Intelligent Robots and Systems, 2013, pp. 722-727.
Coulson, C. et al., An Autonomous Surgical Robot for Drilling a Cochleostomy: Preliminary Porcine Trial, Clinical Otolaryngology, 2008, 33:343-347.
Decker, R. et al., A Biocompatible Near-Infrared 3D Tracking System, IEEE Trans. Biomed. Eng., 2017, 64 (3):549-556.
Dijkstra, E., A Note on Two Problems in Connexion with Graphs, Numerische Mathematik, 1959, 1:269-271.
Ferlay, J. et al., Cancer Incidence and Mortality Worldwide: Sources, Methods and Major Patterns in GLOBOCAN 2012, International Journal of Cancer, 2015, 136(5):E359-E386.
Fu, T. et al., The Role of Transoral Robotic Surgery, Transoral Laser Microsurgery, and Lingual Tonsillectomy in the Identification of Head and Neck Squamous Cell Carcinoma of Unknown Primary Origin: A Systematic Review, Journal of Otolaryngology—Head & Neck Surgery, 2016, 45:28, pp. 1-10.
Fullum, T. et al., Comparison of the Clinical and economic Outcomes Between Open and Minimally Invasive Appendectomy and Colectomy: Evidence from a Large Commercial Payer Database, Surgical Endoscopy, 2010, 24 (4):845-853.
Haidegger, T., Autonomy for Surgical Robots: Concepts and Paradigms, IEEE Transactions on Medical Robotics and Bionics, 2019, 1(2):65-76.
Hennersperger, C. et al., Towards MRI-Based Autonomous Robotic US Acquisitions: A First Feasibility Study, IEEE Transactions on Medical Imaging, 2017, 36(2):538-548.
Hu, D. et al., Semi-Autonomous Image-Guided Brain Tumor Resection Using an Integrated Robotic System: A Bench-Top Study, International Journal of Medical Robotics, 2018, 14(1):e1872, 40 pages.
Huang, S. et al., Oral Cancer: Current Role of Radiotherapy and Chemotherapy, Med Oral Patol Oral Cir Buscal, 2013, 18(2):e233-e240.
Jackson, R. et al., Needle Path Planning for Autonomous Robotic Surgical Suturing, IEEE International Conference on Robotics and Automation, 2013, 2013:1669-1675.
Jackson, R. et al., Needle-Tissue Interaction Force State Estimation for Robotic Surgical Suturing, IEEE/RSJ International Conference on Intelligent Robots and Systems (IROS), 2016, pp. 3659-3664.
Jackson, R. et al., Real-Time Visual Tracking of Dynamic Surgical Suture Threads, IEEE Trans Autom Sci Eng, 2018, 15(3):1078-1090.
Kazanzides, P. et al., An Integrated System for Cementless Hip Replacement, IEEE Engineering in Medicine and Biology Magazine, 1995, 14(3):307-313.

(56) References Cited

OTHER PUBLICATIONS

Knoll, A. et al., Selective Automation and Skill Transfer in Medical Robotics: A Demonstration on Surgical Knot-Tying, International Journal of Medical Robotics and Computer Assisted Surgery, 2012, 8:384-397.
Lavalle, S. et al., Randomized Kinodynamic Planning, International Journal of Robotics Research, 2001, 20 (5):378-400.
Le, H. et al., Experimental Assessment of a 3-D Plenoptic Endoscopic Imaging System, Chin Opt Lett, 2017, 15(5), 15 pages.
Le, H. et al., Semi-Autonomous Laparoscopic Robotic Electro-Surgery with a Novel 3D Endoscope, IEEE International Conference on Robotics and Automation, 2018, 2018:6637-6644.
Leonard, S. et al., Smart Tissue Anastomosis Robot (STAR): A Vision-Guided Robotics System for Laparoscopic Suturing, IEEE Transactions on Biomedical Engineering, 2014, 61(4):1305-1317.
Leonard, S. et al., Smart Tissue Anastomosis Robot (STAR): Accuracy Evaluation for Supervisory Suturing Using Near-Infrared Fluorescent Markers, IEEE International Conference on Robotics & Automation, 2014, pp. 1889-1894.
Liu, M., Robotic Online Path Planning on Point Cloud, IEEE Transactions on Cybernetics, 2016, 46(5):1217-1228.
Liu, S. et al., Preoperative Surgical Planning for Robot-Assisted Liver Tumor Ablation Therapy Based on Collision-Free Reachable Workspaces, International Journal of Robotics and Automation, 2017, 32(5):440-457.
Marchand, E. et al., ViSP for Visual Servoing: A Generic Software Platform with a Wide Class of Robot Control Skills, IEEE Robotics and Automation Magazine, 2005, 12(4):40-52.
Marescaux, J. et al., Next Step in Minimally Invasive Surgery: Hybrid Image-Guided Surgery, Journal of Pediatric Surgery, 2015, 50(1):30-36.
Mercante, G. et al., Transoral Robotic Surgery (TORS) for Tongue Base Tumours, Acta Otorhinolaryngologica Italica, 2013, 33(4):230-235.
Newcombe, R. et al., DynamicFusion: Reconstruction and Tracking of Non-Rigid Scenes in real-Time, Proceedings of the IEEE Conference on Computer Vision and Pattern Recognition, 2015, pp. 343-352.
Opfermann, J. et al., Semi-autonomous Electrosurgery for Tumor Resection Using a Multi-Degree of Freedom Electrosurgical Tool and Visual Servoing, Int. Conf. Intell. Robots and Sys., 2017, pp. 3653-3660.
Quigley, M. et al., ROS: An Open-Source Robot Operating System, ICRA Workshop on Open Source Software, 2009, vol. 3, 6 pages.
REFLEXXES. Reflexxes Motion Libraries, Version dated Sep. 20, 2018, http://web.archive.org/web/20180920075318/http://www.reflexxes.ws/reflexxes-motion-libraries-details.html, 2 pages.
Rosten, E. et al., Fusing Points and Lines for High Performance Tracking, Tenth IEEE International Conference on Computer Vision (ICCV'05), 2005, 2:1508-1515.
Rusu, R. et al., 3D is Here: Point Cloud Library (PCL), IEEE International Conference on Robotics and Automation, 2011, pp. 1-4.
Saeidi, H. et al., A Mixed-Initiative Haptic Teleoperation Strategy for Mobile Robotic Systems Based on Bidirectional Computational Trust Analysis, IEEE Transactions on Robotics, 2017, 33(6):1500-1507.
Saeidi, H. et al., A Confidence-Based Shared Control Strategy for the Smart Tissue Autonomous Robot (STAR), 2018 IEEE/RSJ International Conference on Intelligent Robots and Systems (IROS), 2018, pp. 1268-1275.
Saeidi, H. et al., Autonomous Laparoscopic Robotic Suturing with a Novel Actuated Suturing Tool and 3D Endoscope, IEEE International Conference on Robotics and Automation, 2019, 2019:1541-1547.
Salman, M. et al., Use, Cost, Complications, and Mortality of Robotic Versus Nonrobotic General Surgery Procedures Based on a Nationwide Database, The American Surgeon, 2013, 79(6):553-560.
Schnabel, R. et al., Efficient RANSAC for Point-Cloud Shape Detection, Computer Graphics Forum, 2007, 26(2):214-226.
Shademan, A. et al., Feasibility of Near-Infrared Markers for Guiding Surgical Robots, Optical Modeling and Performance Predictions VI, Proc. of SPIE, 2013, vol. 8840, 10 pages.
Shademan, A. et al., Supervised Autonomous Robotic Soft Tissue Surgery, Science Translational Medicine, 2016, 8 (337):108.
Sinclair, D., S-hull: A Fast Radial Sweep-Hull Routine for Delaunay Triangulation, arXiv:1604.01428, 2016, pp. 1-7.
Smits, R., KDL: Kinematics and Dynamics Library, Published Feb. 25, 2010, http://web.archive.org/web/20201128223717/https://www.orocos.org/kdl/release-102.html, 1 page.
Stephan, D. et al., First Experiences with the New Senhance(R) Telerobotic System in Visceral Surgery, Visceral Medicine, 2018, 34(1):31-36.
Stewart, C. et al., Robotic Surgery Trends in General Surgical Oncology from the National Inpatient Sample, Surgical Endoscopy, 2019, 33(8):2591-2601.
Sucan, I. et al., The Open Motion Planning Library, IEEE Robotics & Automation Magazine, 2012, 19(4):72-82.
Tirelli, G. et al., NBI Utility in the Pre-Operative and Intra-Operative Assessment of Oral Cavity and Oropharyngeal Carcinoma, American Journal of Otolaryngology, 2017, 38(1):65-71.
Van Der Merwe, R. et al., The Unscented Particle Filter, Advances in Neural Information Processing Systems, 2001, pp. 584-590.
Vicini, C. et al., A Novel Approach Emphasising Intra-Operative Superficial Margin Enhancement of Head-Neck Tumours with Narrow-Band Imaging in Transoral Robotic Surgery, Acta Otorhinolaryngologica Italica, 2015, 35:157-161.
Wan, E. et al., The Unscented Kalman Filter for Nonlinear Estimation, Proceedings of the IEEE 2000 Adaptive Systems for Signal Processing, Communications, and Control Symposium (Cat. No.00EX373), Oct. 2000, pp. 153-158.
Wu, T. et al., Optical Imaging for Medical Diagnosis Based on Active Stereo Vision and Motion Tracking, Optics Express, 2007, 15(16):10421-10426.
Wu, C. et al., In-Vivo Optical Imaging in Head and Neck Oncology: Basic Principles, Clinical Applications and Future Directions, International Journal of Oral Science, 2018, 10(2):1-13.
Xia, T. et al., An Integrated System for Planning, Navigation and Robotic Assistance for Skull Base Surgery, Int. J. Med. Robot., 2008, 4(4):321-330.
Yip, M. et al., Chapter 1, Robot Autonomy for Surgery, Encyclopedia of Medical Robotics, 2017, 1:281-313.
Zhou, X. et al., Path Planning for Robot-Enhanced Cardiac Radiofrequency Catheter Ablation, IEEE International Conference on Robotics and Automation, 2016, pp. 4172-4177.
PCT International Search Report and Written Opinion, PCT/US2019/032635, Jul. 29, 2019, 8 pages.
PCT International Search Report and Written Opinion, PCT/US2020/033270, Jul. 17, 2020, 9 pages.

* cited by examiner

CONFIDENCE-BASED ROBOTICALLY-ASSISTED SURGERY SYSTEM

PRIORITY CLAIM

This application is a continuation-in-part of International Application No. PCT/US2019/032635, filed May 16, 2019, which claims the benefit of, and claims priority to, U.S. Provisional Application No. 62/672,485, filed May 16, 2018, and is a continuation of International Application No. PCT/US2020/033270, filed May 15, 2020, which claims the benefit of, and claims priority to, U.S. Provisional Application No. 62/848,979, filed May 16, 2019 and U.S. Provisional Application No. 62/907,872, filed Sep. 30, 2019. Each of the preceding patent applications is hereby incorporated by reference herein in its entirety.

STATEMENT REGARDING FEDERALLY SPONSORED RESEARCH

This invention was made with government support under R01 EB020610, and R21 EB024707 awarded by the National Institutes of Health. The government has certain rights in the invention.

BACKGROUND

Advances in robotic and camera technology has led to dramatic changes in medical robotics over the past two decades. Many robotically-assisted surgery (RAS) systems are based on tele-operation (e.g., remote operation or operation at a distance), and include robotic arms or similar equipment, cameras, highly dexterous surgical tools, etc. Many RAS systems provide a minimally invasive surgery (MIS) approach, which can be faster, safer and require less patient recovery time. Additionally, an RAS system can reduce human errors and improve patient outcomes by leveraging robotic accuracy and repeatability during certain surgical procedures. However, the degree of interaction between RAS systems and human operators has not been found to be optimal. For example, a completely autonomous RAS system has not been feasible for many surgical situations, procedures and environments. Therefore, a need exists for an RAS system that optimizes the amount of autonomous and manual interaction with an operator.

SUMMARY

In an example embodiment, a system may include a camera system that includes a first camera and a second camera, an articulating member that includes a tool, and a computer. The computer may include at least one processor and a non-transitory memory configured to store computer-readable instructions which, when executed, cause the at least one processor to, receive image data from the first camera, receive point cloud image data from the second camera, wherein the image data and the point cloud image data correspond to a tissue on which markers are disposed, identify marker positions of the markers based on the image data and the point cloud image data, generate a path between a first point on the point cloud and a second point on the point cloud based at least on the marker positions, filter the path, receive real-time position data corresponding to the articulating member, generate a three-dimensional (3D) trajectory based on the filtered path and the real-time position data, generate control commands based on the 3D trajectory, and control the articulating member and the tool to follow the 3D trajectory based on the control commands.

In some embodiments, the tool may include an electrocautery tool. The computer-readable instructions which cause the at least one processor to control the articulating member and the tool may further cause the electrocautery tool to cut the tissue along the path.

In some embodiments, the first camera may include a near-infrared (NIR) camera, the second camera may include a red-blue-green-depth (RGBD) camera, the image data may include NIR image data, and the markers may include NIR markers.

In some embodiments, the computer-readable instructions which cause the at least one processor to generate the path may further cause the at least one processor to identify projected marker positions by applying an offsetting technique to project the marker positions outward on a point cloud of the point cloud image data, and reference waypoints on the point cloud between two of the projected marker positions, such that the reference waypoints of the path are separate from the marker positions by at least a predetermined margin, wherein the path comprises the reference waypoints.

In some embodiments, the computer-readable instructions which cause the at least on processor to filter the path may further cause the at least one processor to select tracked waypoints as a subset of the reference waypoints, and generate filtered waypoints by applying a filtering algorithm to track the tracked waypoints.

In some embodiments, the filtering algorithm may be selected from the group consisting of a recursive least square algorithm, a Kalman filter, an extended Kalman filter, an unscented Kalman filter, and a particle filter.

In some embodiments, the computer-readable instructions, when executed, may further cause the at least one processor to calculate at least one autonomous confidence indicator based on autonomous incision error, calculate a manual confidence indicator based on manual incision error, generate at least one allocation function based on the manual confidence indicator and the at least one autonomous confidence indicator, and generate the control commands based on the at least one allocation function.

In some embodiments, the at least one autonomous confidence indicator may be selected from the group consisting of a roll angle confidence indicator which is generated based on roll angle error, a pitch angle confidence indicator which is generated based on pitch angle error, a distance confidence indicator which is generated based on distance error, and a density confidence indicator which is generated based on density error. The at least one allocation function may include multiple of allocation functions corresponding to movement of the articulating member in three-dimensional directions, and roll, pitch, and yaw of the articulated member.

In an example embodiment, a method may include steps for generating image data and point cloud image data corresponding to a region of interest on which markers are disposed, identifying marker positions of the markers based on the image data and the point cloud image data, generating a path between a first point of the point cloud image data and a second point of the point cloud image data, based at least on the marker positions, receiving real-time position data corresponding to an articulating member, generating a three-dimensional (3D) trajectory for the articulating member based on the path and the real-time position data, generating control commands based on the 3D trajectory, and controlling the articulating member to follow the 3D trajectory based on the control commands.

In some embodiments, the articulating member may include a robotic arm, and controlling the articulating member may include causing the robotic arm to cut tissue in the region of interest along the path.

In some embodiments, the step of generating the path may include identifying projected marker positions by applying an offsetting technique to project the marker positions outward on a point cloud of the point cloud image data, and generating reference waypoints on the point cloud between two of the projected marker positions, such that the reference waypoints of the path are separate from the marker positions by at least a predetermined margin, wherein the path comprises the reference waypoints.

In some embodiments, the step of filtering the path may include selecting tracked waypoints as a subset of the reference waypoints, and generating filtered waypoints by applying a filtering algorithm to track the tracked waypoints.

In some embodiments, the filtering algorithm may be selected from the group consisting of: a recursive least square algorithm, a Kalman filter, an extended Kalman filter, an unscented Kalman filter, and a particle filter.

In some embodiments, the method may further include steps for calculating at least one autonomous confidence indicator based on autonomous incision error, calculating a manual confidence indicator based on manual incision error, generating at least one allocation function based on the manual confidence indicator and the at least one autonomous confidence indicator, and generating the control commands based on the at least one allocation function.

In some embodiments, the at least one autonomous confidence indicator may include at least one confidence indicator selected from a group consisting of a roll angle confidence indicator which is generated based on roll angle error, a pitch angle confidence indicator which is generated based on pitch angle error, a distance confidence indicator which is generated based on distance error, and a density confidence indicator which is generated based on density error. In some embodiments, the at least one allocation function comprises a plurality of allocation functions corresponding to movement of the articulating member in three-dimensional directions, and roll, pitch, and yaw of the articulated member.

In some embodiments, the image data may include near-infrared (NIR) image data, and the markers may include NIR markers.

In an example embodiment, a system may include an articulating member including a tool, and a computer, coupled to the articulating member. The computer may include at least one processor configured to, determine a first confidence indicator based on a manual control mode for the articulating member, determine a second confidence indicator based on an autonomous control mode for the articulating member, generate an allocation function based on the first confidence indicator and the second confidence indicator, and generate a control command for the articulating member based on the allocation function.

In some embodiments, the system further comprises a camera system that includes a first camera and a second camera, wherein the processor is further configured to: receive image data from the first camera; receive point cloud image data from the second camera, wherein the image data and the point cloud image data correspond to a tissue on which markers are disposed; identify marker positions of the markers based on the image data and the point cloud image data; generate a path between a first point on the point cloud and a second point on the point cloud based at least on the marker positions; filter the path; receive real-time position data corresponding to the articulating member; generate a three-dimensional (3D) trajectory based on the filtered path and the real-time position data; generate control commands based on the 3D trajectory; and control the articulating member and the tool to follow the 3D trajectory based on the control commands.

In some embodiments, the first confidence indicator is based on first data acquired when the processor is operating in the manual control mode during a first performance of a predetermined task using the tool, and the first data include manual tracking error data associated with a first trajectory of the tool during the first performance of the predetermined task.

In some embodiments, the second confidence indicator is based on second data acquired when the processor is operating in the autonomous control mode during a second performance of the predetermined task, and the second data include autonomous tracking error data associated with a second trajectory of the tool during the second performance of the predetermined task.

In some embodiments, when the processor is operating in a shared control mode to perform the predetermined task using the tool, the processor is further configured to: generate a manual control command for the articulating member based on input data received from an input device coupled to the processor; generate an autonomous control command for the articulating member; generate the control command based on the allocation function, the autonomous control command and the manual control command; convert the control command into a robot-specific control signal; and send the robot-specific control signal to the articulating member.

In some embodiments, the allocation function selects either the manual control command or the autonomous control command as the control command.

In some embodiments, the allocation function defines at least one decision threshold and determines which of the manual control command or the autonomous control command is selected as the control command.

In some embodiments, the control command is a combination of the manual control command and the autonomous control command, and the allocation function defines respective percentages of the manual control command and the autonomous control command.

In some embodiments, the processor is further configured to provide a graphical user interface (GUI) on a display coupled to the processor, the GUI including an image of a work space in which the predetermined task is performed, a desired trajectory of the tool for the predetermined task, at least one manual control mode region along the desired trajectory, and at least one autonomous control mode region along the desired trajectory.

In some embodiments, the processor is further configured to receive, from the input device, a user selection of either the manual control command or the autonomous control command as the control command.

In some embodiments, the predetermined task is a two-dimensional pattern cutting surgical task.

In an example embodiment, a method may include determining a first confidence indicator based on a manual control mode for an articulating member, determining a second confidence indicator based on an autonomous control mode for the articulating member, generating an allocation function based on the first confidence indicator and the second confidence indicator, and generating a control command for the articulating member based on the allocation function.

DETAILED DESCRIPTION

Figure 1:
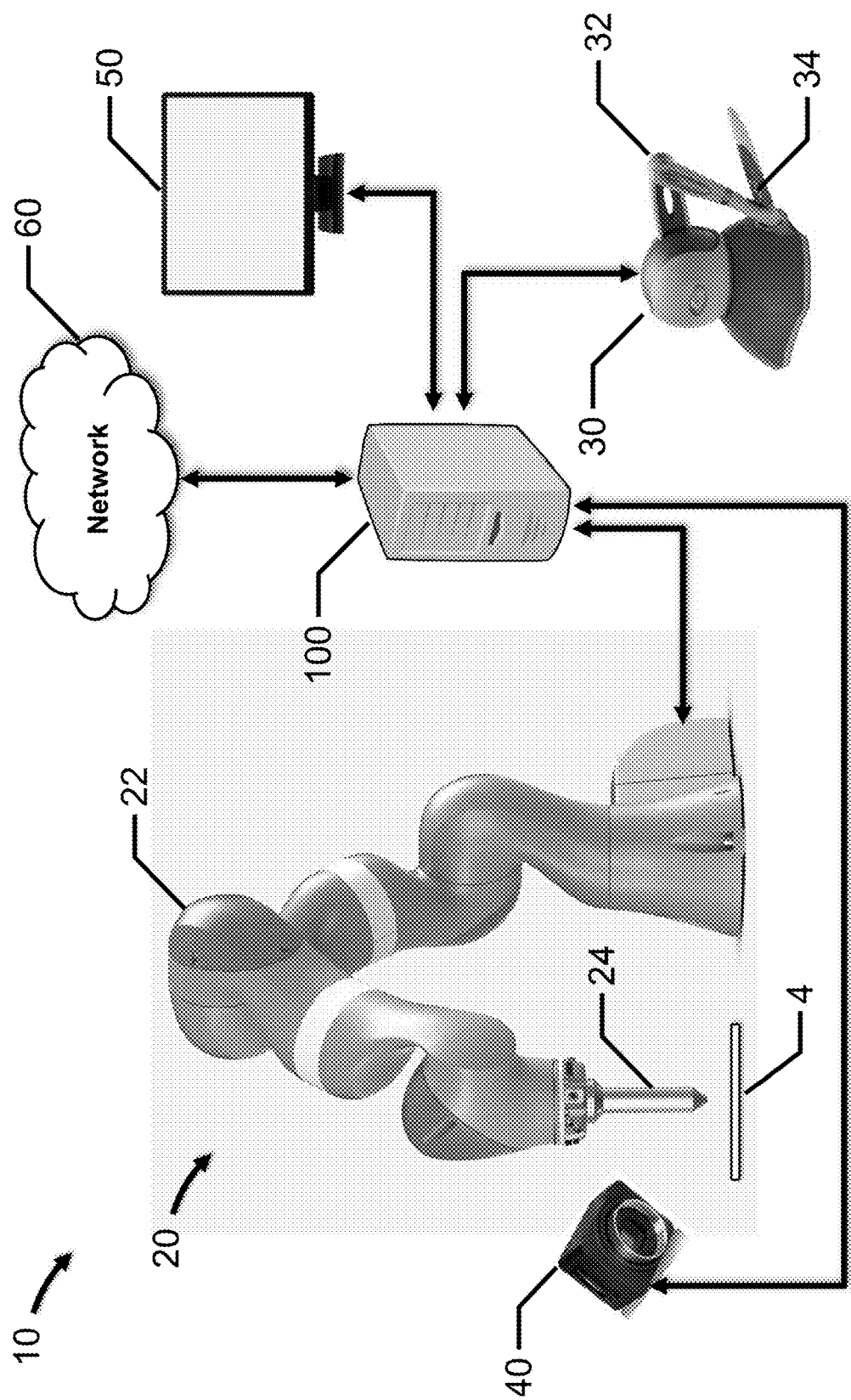
FIG. 1 depicts a schematic diagram of an RAS system, in accordance with an embodiment of the present disclosure.

Embodiments of the present disclosure will now be described with reference to the drawing figures, in which like reference numerals refer to like parts throughout.

Embodiments of the present disclosure advantageously improve both RAS system efficiency and patient outcomes by combining the best features of automation with the complementary skills of the surgeon operating the RAS system. While automation of the RAS system may provide greater accuracy and repeatability in certain surgical situations, automation is not infallible and safe operation requires surgeon supervision and possible intervention. Accordingly, the present disclosure provides a control system that allows surgical procedures to be performed collaboratively between robot and surgeon with the highest possible degree of autonomy, while ensuring safe operation at all times.

More particularly, embodiments of the present disclosure provide a confidence-based shared control system that provides an automated control allocation during a surgical task, situation, procedure, etc. Importantly, the confidence-based shared control system improves the surgical performance of any surgeon by reducing not only the overall error committed by the surgeon, but also the workload of the surgeon during the task.

FIG. 1 depicts a schematic diagram of RAS system 10, in accordance with an embodiment of the present disclosure.

RAS system 10 includes computer 100 coupled to robot 20, input device 30, camera 40 and display 50. Tissue 4 may include one or more tissue samples, a region of interest of a patient, etc. Robot 20 includes articulated member or arm 22 and tool 24. Generally, tool 24 is an extension of arm 22, and may be, for example, a surgical tool, an electro-surgical tool, a laser, etc. The movement of tool 24 is controlled by commands to robot 20. Input device 30 includes stylus 32 and one or more switches or buttons 34. Computer 100 may also be coupled to network 60, which may include one or more local area networks, wide area networks, the Internet, etc.

In one embodiment, robot 20 is a Smart Tissue Autonomous Robot (STAR) that includes a KUKA LBR iiwa robot with a 7-DOF (degree of freedom) lightweight arm 22 and a surgical tool 24. Robot 20 receives control commands or signals from computer 100, and sends positional information for arm 22 to computer 100. The control commands or signals may include one or more of the following types of data: position, velocity, acceleration, force, torque, etc.

In one embodiment, surgical tool 24 is an electro-cautery tool that is based on a 2-DOF laparoscopic grasper Radius T manufactured by Tuebingen Scientific. Electro-cautery tool 24 includes a shaft, a quick release interface that is electrically isolated from the shaft, and two conductors, disposed within the center of electro-cautery tool 24, that are electrically coupled to an electro-surgical generator (ESG) (not depicted for clarity). In operation, a needle electrode is inserted into the quick-release interface, and a cutting waveform is selected on the ESG. When the surgeon activates an input control for the ESG, such as, for example, a foot pedal, a button or switch, etc., the ESG receives a control signal. In response, the ESG generates an electrical signal representing the cutting waveform, and then sends the electrical signal to the needle electrode. A grounding pad, disposed underneath the tissue sample, patient, etc. in task space 2, is coupled to the ESG to complete the electrical circuit. The electrical signal vaporizes tissue in contact with the electrode, thereby cutting the tissue. Alternatively, computer 100 may receive the ESG control signal from input device 30, and then send the ESG control signal to the ESG. For example, input device 30 may include a button or switch that is mapped to the ESG control signal. Alternatively, input device 30 may be coupled to the ESG and provide the ESG control signal directly thereto.

Other embodiments of robot 20, including different arms 22 and tools 24, are also contemplated, such as, for example, a motorized suturing device, etc.

In one embodiment, input device 30 is a 6-DOF Sensable Technologies Phantom Omni haptic device 30 that allows the surgeon to manually control robot 20. In this embodiment, haptic device 30 sends positional information for stylus 32 and commands received through buttons 34 to computer 100, and may receive haptic feedback from computer 100. If haptic feedback is provided, haptic device 30 includes one or more haptic actuators that render the haptic feedback to the surgeon. Haptic feedback may include force, vibration, motion, texture, etc. Other embodiments of input device 30 are also contemplated.

In one embodiment, camera 40 is a Point Grey Chameleon RGB (red green blue) camera. Camera 40 sends image data to computer 100 that provide visual feedback to the surgeon and input data for the autonomous control mode discussed below. Other embodiments of camera 40 are also contemplated.

Figure 2:
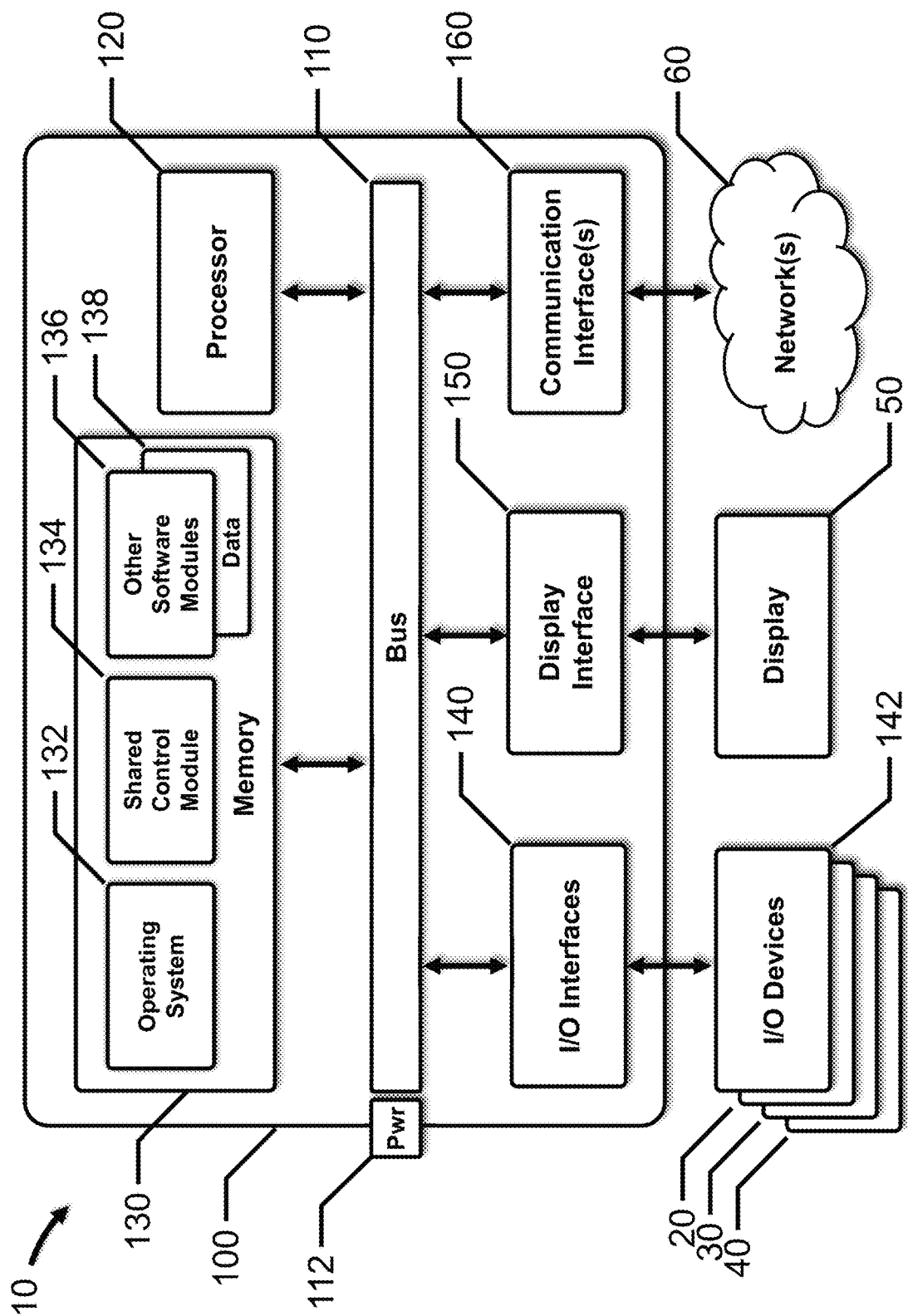
FIG. 2 depicts a block diagram of the RAS system depicted in FIG. 1, in accordance with an embodiment of the present disclosure.

FIG. 2 depicts a block diagram of RAS system 10 depicted in FIG. 1, in accordance with an embodiment of the present disclosure.

Computer 100 includes bus 110, processor 120, memory 130, I/O interfaces 140, display interface 150, and one or more communication interfaces 160. Generally, I/O interfaces 140 are coupled to I/O devices 142 using a wired or wireless connection, display interface 150 is coupled to display 50, and communication interface 160 is connected to network 60 using a wired or wireless connection.

Bus 110 is a communication system that transfers data between processor 120, memory 130, I/O interfaces 140, display interface 150, and communication interface 160, as well as other components not depicted in FIG. 1. Power connector 112 is coupled to bus 110 and a power supply (not shown).

Processor 120 includes one or more general-purpose or application-specific microprocessors to perform computation and control functions for computer 100. Processor 120 may include a single integrated circuit, such as a microprocessing device, or multiple integrated circuit devices and/or circuit boards working in cooperation to accomplish the functions of processor 120. In addition, processor 120 may execute computer programs or modules, such as operating system 132, shared control module 134, other software modules 136, etc., stored within memory 130.

Memory 130 stores information and instructions for execution by processor 120. Generally, memory 130 may include a variety of non-transitory computer-readable medium that may be accessed by processor 120. In various embodiments, memory 130 may include volatile and non-volatile medium, non-removable medium and/or removable medium. For example, memory 130 may include any combination of random access memory ("RAM"), dynamic RAM (DRAM), static RAM (SRAM), read only memory ("ROM"), flash memory, cache memory, and/or any other type of non-transitory computer-readable medium.

Memory 130 contains various components for retrieving, presenting, modifying, and storing data. For example, memory 130 stores software modules that provide functionality when executed by processor 120. The software modules include an operating system 132 that provides operating system functionality for computer 100. The software modules also include shared control module 134 that provides functionality for controlling robot 20. In certain embodiments, shared control module 134 may include a plurality of modules, each module providing specific individual functionality for controlling robot 20. Other software modules 136 may cooperate with shared control module 134 to provide functionality for controlling robot 20, such as planning algorithms, robot controllers, computer vision, control allocation strategies, etc.

In certain embodiments, other software modules 136 may include a Robot Operating System (ROS), which provides a flexible collection of tools, libraries, device drivers, such as robot device drivers, sensor device drivers, etc., conventions, etc. For example, other software modules 136 may include an OpenCV (Open Source Computer Vision) library that provides a common infrastructure for computer vision applications, one or more Reflexxes Motion Libraries that provide instantaneous trajectory generation capabilities for motion control systems, a Kinematics and Dynamics Library (KDL) in Open Robot Control Systems (OROCOS) that provides an application independent framework for modelling and computation of kinematic chains for robots, etc.

Data 138 may include data associated with operating system 132, shared control module 134, other software modules 136, etc.

I/O interfaces 140 are configured to transmit and/or receive data from I/O devices 142. I/O interfaces 140 enable connectivity between processor 120 and I/O devices 142 by encoding data to be sent from processor 120 to I/O devices 142, and decoding data received from I/O devices 142 for processor 120. Generally, data may be sent over wired and/or a wireless connections. For example, I/O interfaces 140 may include one or more wired communications interfaces, such as USB, Ethernet, etc., and/or one or more wireless communications interfaces, coupled to one or more antennas, such as WiFi, Bluetooth, cellular, etc.

Generally, I/O devices 142 provide input to computer 100 and/or output from computer 100. As discussed above, I/O devices 142 are operably connected to computer 100 using either a wireless connection or a wired connection. I/O devices 142 may include a local processor coupled to a communication interface that is configured to communicate with computer 100 using the wired or wireless connection. For example, I/O devices 142 include robot 20, input device 30, camera 40, and may include other devices, such as a joystick, keyboard, mouse, touch pad, etc.

Display interface 150 is configured to transmit image data from computer 100 to monitor or display 50.

Communication interface 160 is configured to transmit data to and from network 60 using one or more wired or wireless connections. Network 60 may include one or more local area networks, wide area networks, the Internet, etc., which may execute various network protocols, such as, for example, wired and wireless Ethernet, Bluetooth, etc. Network 60 may also include various combinations of wired and/or wireless physical layers, such as, for example, copper wire or coaxial cable networks, fiber optic networks, Bluetooth wireless networks, WiFi wireless networks, CDMA, FDMA and TDMA cellular wireless networks, etc.

Figure 3A:
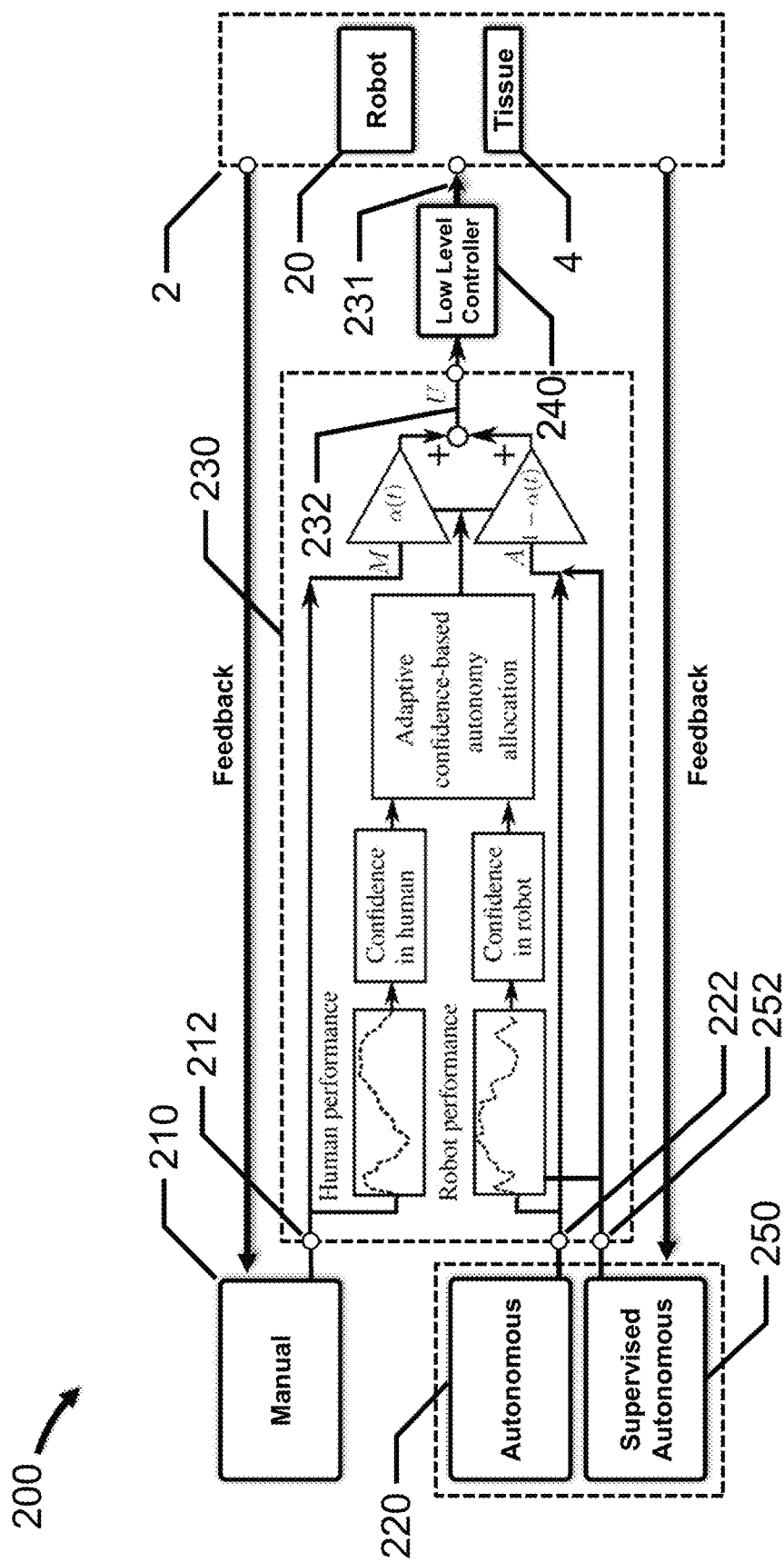
FIG. 3A depicts a block diagram of a shared control system, in accordance with an embodiment of the present disclosure.

FIG. 3A depicts a block diagram of shared control system 200, in accordance with an embodiment of the present disclosure. The functionality represented by this block diagram is provided by one or more software modules including shared control module 134, other software modules 136, etc.

Generally, shared control system 200 performs complex surgical procedures collaboratively between robot 20 and the surgeon with the highest possible degree of autonomy, while ensuring safe operation at all times. In one sense, shared control system 200 is "self-aware" of the limitations of its automation capabilities.

Shared control system 200 includes manual control subsystem 210, autonomous control subsystem 220, a shared control subsystem 230, and a supervised autonomous control subsystem 250 (e.g., described below in connection with FIG. 16). Also depicted in FIG. 3A is task space 2 including robot 20 and tissue 4. Tissue 4 may be one or more tissue samples, a region of interest of a patient, etc. Manual control subsystem 210 generates manual control command 212, which is input to shared control subsystem 230. Autonomous control subsystem 220 generates autonomous control command 222, which is input to shared control subsystem 230. Additionally or alternatively, the supervised autonomous control subsystem 250 may generate a supervised autonomous control command 252. Shared control subsystem 230 generates shared control command 232.

In the embodiment depicted in FIG. 3A, shared control command 232 is input to low level controller 240, which converts shared control command 232 to robot-specific control signal 231. Robot-specific control signal 231 is then sent to robot 20. For the embodiment including the KUKA LBR iiwa robot described above, low level controller 240 is a software module that is specific to this robot, such as the IIWA (Intelligent Industrial Work Assistant) Stack. In other embodiments, shared control command 232 may be sent directly to robot 20, which converts shared control command 232 to the appropriate robot-specific control signal.

Shared control subsystem 230 generates shared control command 232 according to the Equation 1:

$$U(t) = \alpha(t) \cdot M(t) + (1 - \alpha(t)) \cdot A(t) \quad (1)$$

In Equation 1, manual control commands from the surgeon, $M(t)$, are combined with autonomous control commands, $A(t)$, using complementary scales $\alpha(t) \in [0, 1]$ and $1 - \alpha(t)$, respectively, to form the shared control command to the robot, $U(t)$. The allocation function $\alpha(t)$ defines the respective percentages of the manual control command $M(t)$ and the autonomous control command $A(t)$ that are combined to form the shared control command $U(t)$. The allocation function $\alpha(t)$ defines these percentages with respect to an independent variable x that reflects or indicates certain performance criteria for the shared control subsystem 230. With respect to FIG. 3A, manual control command 212 represents $M(t)$, either the autonomous control command 222 or the supervised autonomous control command 252 may represent $A(t)$, and shared control command 232 represents $U(t)$.

When $\alpha(t)$ is 0, the allocation function selects the autonomous control command as the shared control command. In other words, the shared control command is not influenced by the manual control command when $\alpha(t)$ is 0. Conversely, when $\alpha(t)$ is 1, the allocation function selects the manual control command as the shared control command. In other words, the shared control command is not influenced by the autonomous control command when $\alpha(t)$ is 1. When $\alpha(t)$ is a number between 0 and 1, the allocation function blends or combines the manual control command and the autonomous control command, based on the value of the allocation function, to generate the shared control command.

Figure 9:
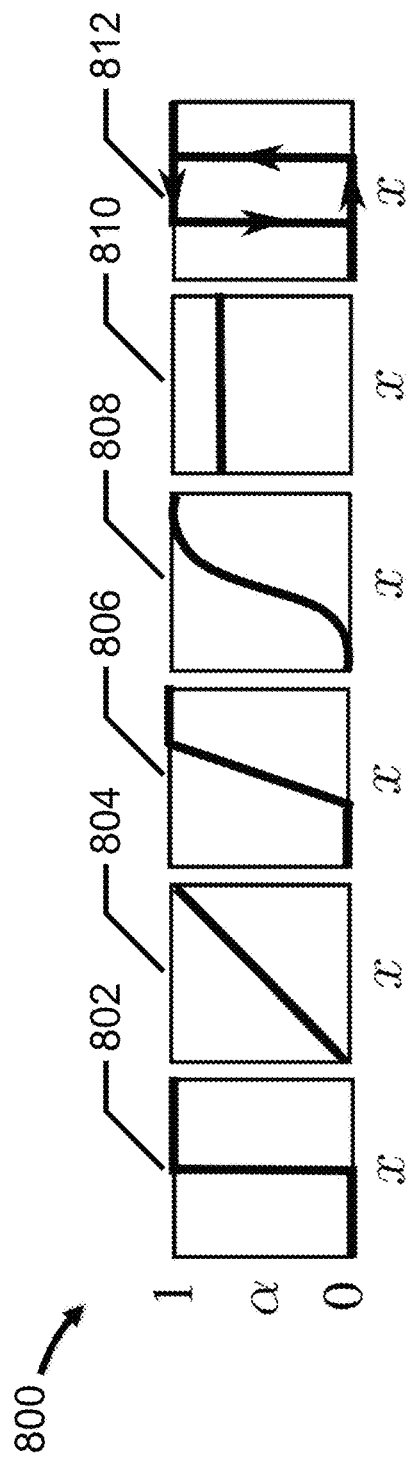
FIG. 9 depicts several allocation functions, in accordance with embodiments of the present disclosure.

Generally, the allocation function $\alpha(t)$ changes dynamically during the task and is a function of the independent variable x. Referring to FIG. 9, several allocation functions 800 are depicted, in accordance with embodiments of the present disclosure. Allocation function 802 is a function of tracking accuracy. Allocation function 804 is a function of proximity to obstacles and/or desired locations. Allocation function 806 is a function of the accuracy of predicting human intentions in controlling the robot. Allocation function 808 is a function of the level of manipulation precision. Allocation function 810 is a fixed function and does not change based on the performance criteria. Generally, performance criteria determine the confidence and hence the allocation function, which is task dependent. Allocation function 812 is a function of trust in the manual and/or autonomous control subsystems, and, more particularly, allocation function 812 is a function of the confidence in the manual and/or autonomous control subsystems and their dynamic uncertainties.

Generation of this confidence-based allocation function $\alpha(t)$ requires identification tests for both manual and autonomous control modes to reveal their respective strengths and weaknesses, and is described in more detail below. The factors affecting manual control mode performance include the angle of camera 40 and the dissimilarities between the kinematics of haptic device 30 and robot 20. The factors affecting autonomous control mode performance include random failures in detecting the desired cutting trajectory as well as any imprecision in the calculation of tool 24 location via the robot kinematic chain.

Figure 3B:
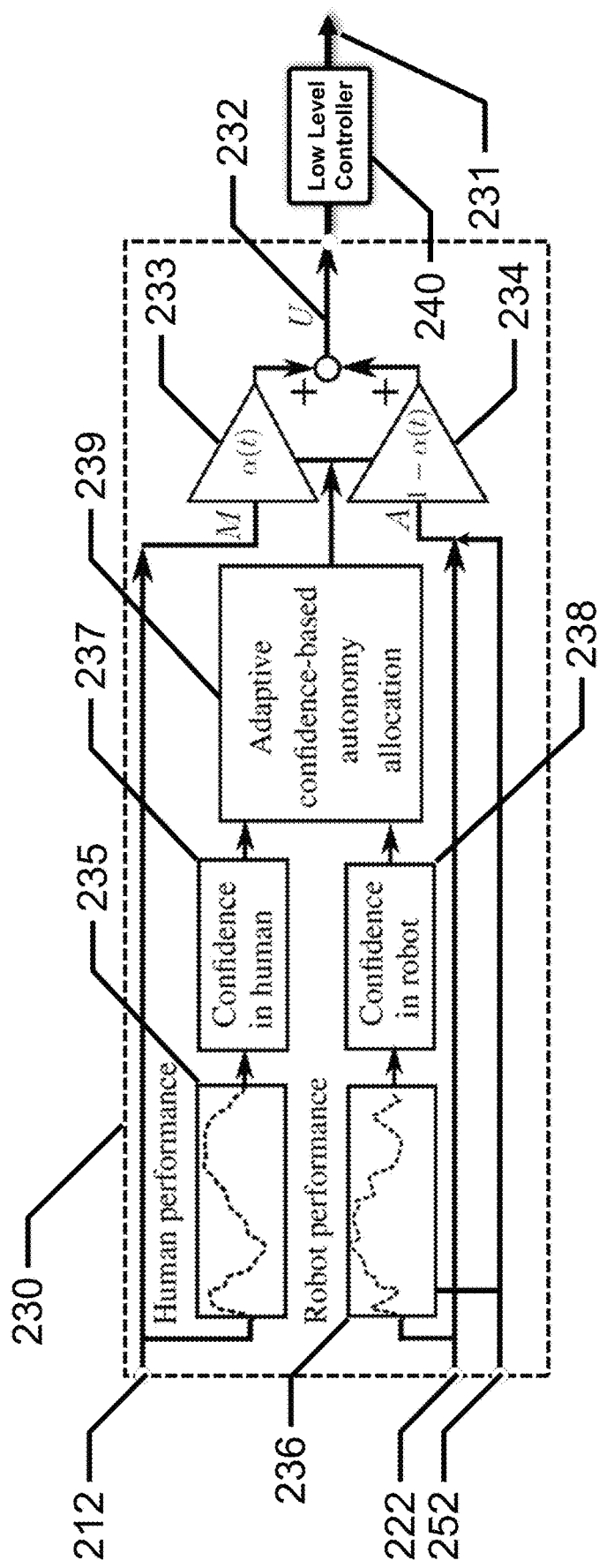
FIG. 3B depicts a block diagram of a shared control subsystem, in accordance with an embodiment of the present disclosure.

FIG. 3B depicts a block diagram of shared control subsystem 230, in accordance with an embodiment of the present disclosure. Also depicted in FIG. 3B is low level controller 240 which converts shared control command 232 into shared control signal 231. The functionality represented by this block diagram is provided by one or more software modules including shared control module 134, other software modules 136, etc.

Scale function 233 applies the allocation function $\alpha(t)$ to manual control command 212, and scale function 234 applies the allocation function $\alpha(t)$ to autonomous control command 222 or the supervised autonomous control command 252. The scaled commands are then combined to form shared control command 232.

Generation of the allocation function $\alpha(t)$ is performed by an adaptive confidence-based autonomy allocation module 239, based on manual confidence indicator 237 and autonomous confidence indicator 238. Manual confidence indicator 237 is determined based on manual tracking error data 235 that is acquired when processor 120 is operating in a manual control mode during performance of a predetermined task using tool 24. Manual tracking error data 235 are associated with the trajectory of tool 24 during performance of the predetermined task. Similarly, autonomous confidence indicator 238 is determined based on autonomous tracking error data 236 that are acquired when processor 120 is operating in an autonomous control mode during performance of the predetermined task using tool 24. The autonomous tracking error data 236 are associated with the trajectory of tool 24 during performance of the predetermined task. Performance of the predetermined task in manual control mode and autonomous control mode, in order to determine the manual and autonomous confidence indicators 237, 238, respectively, represents the identification tests noted above. This process is discussed in more detail below.

Figure 3C:
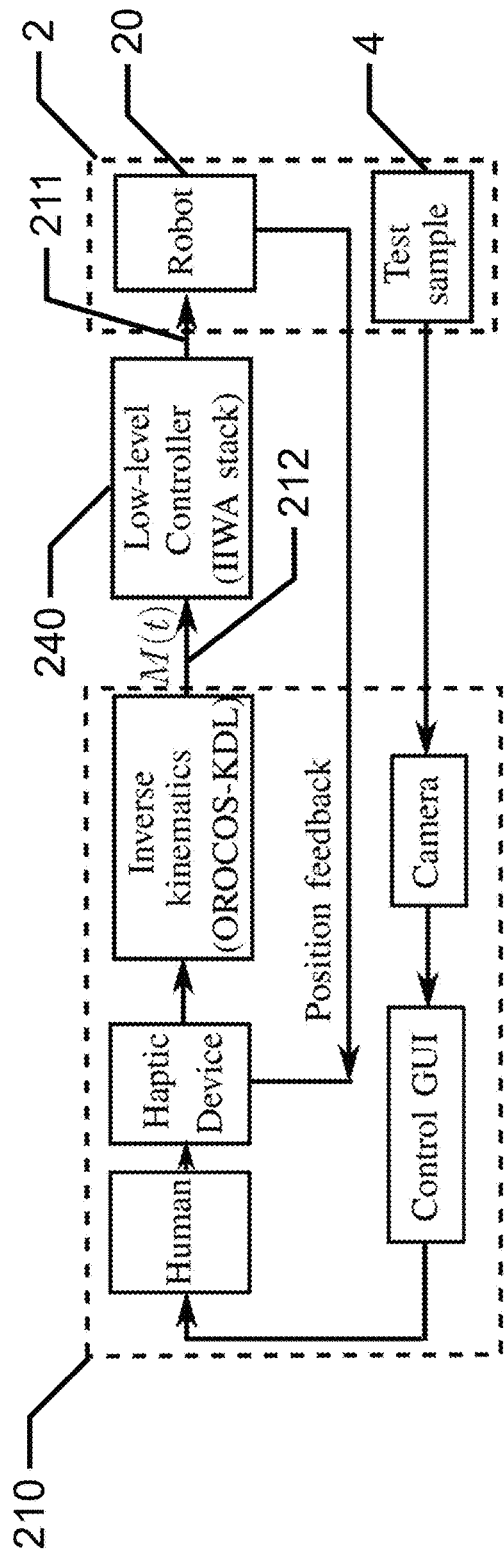
FIG. 3C depicts a block diagram of a manual control subsystem, in accordance with an embodiment of the present disclosure.

FIG. 3C depicts a block diagram of manual control subsystem 210, in accordance with an embodiment of the present disclosure. Also depicted in FIG. 3C are task space 2 including robot 20 and tissue 4, and low level controller 240 which converts manual control command 212 into manual control signal 211. The functionality represented by this block diagram is provided by one or more software modules including shared control module 134, other software modules 136, etc.

To perform a predetermined task in manual control mode, real-time video images from camera 40 are presented on display 50, and the surgeon plans the desired tool trajectory based on a reference trajectory inscribed on tissue 4, such as, for example, a circular pattern cut, and then follows the desired tool trajectory using haptic device 30. The position feedback from robot 20 and the position commands from haptic device 30 are used to determine reference positions of robot 20 in task space 2. In one embodiment, the initial position of robot 20 when the predetermined task starts is identified, and new reference positions read from the displacement of haptic device 30 are added to produce the final position of robot 20 in the Cartesian task-space. Inverse kinematics are applied to generate manual control command 212 in joint-space, and low level controller 240 then converts manual control command 212 to manual control signal 211. The manual control signal 211 is then sent to robot 20 over the appropriate I/O interface 140. In an alternative embodiment, the manual control command 212 is sent to robot 20 over the appropriate I/O interface 140, which processes the command as necessary.

Figure 3D:
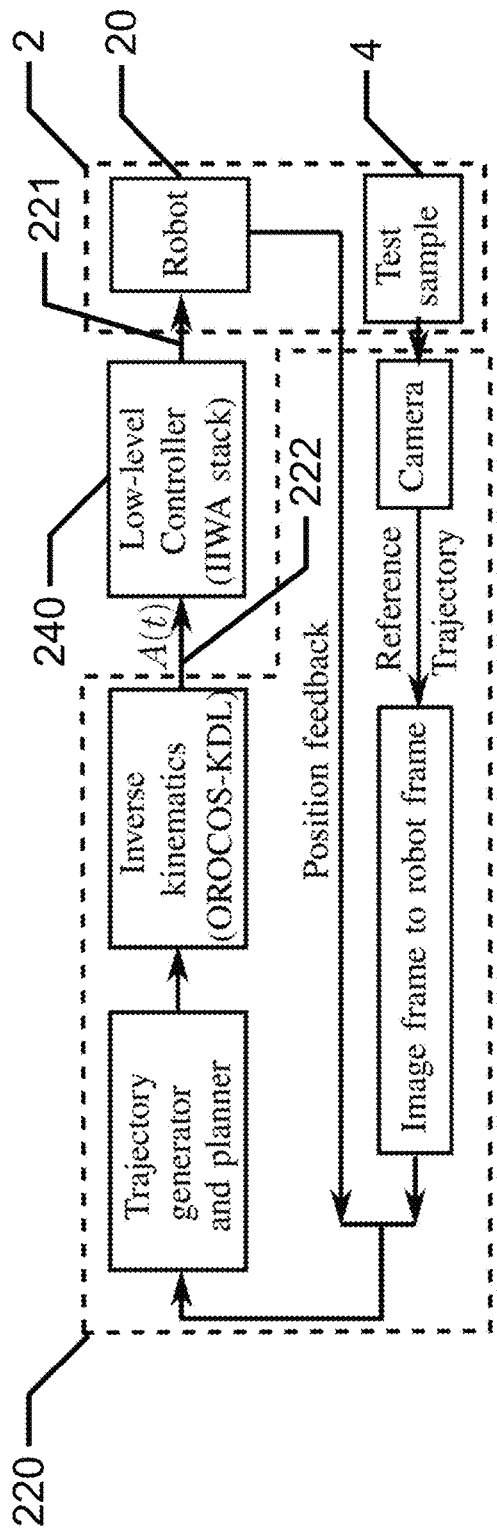
FIG. 3D depicts a block diagram of an autonomous control subsystem, in accordance with an embodiment of the present disclosure.

FIG. 3D depicts a block diagram of autonomous control subsystem 220, in accordance with an embodiment of the present disclosure. Also depicted in FIG. 3D are task space 2 including robot 20 and tissue 4, and low level controller 240 which converts autonomous control command 222 into autonomous control signal 221. The functionality represented by this block diagram is provided by one or more software modules including shared control module 134, other software modules 136, etc.

To perform a predetermined task in autonomous control mode, real-time video frames from camera 40 are processed to detect a reference trajectory inscribed on tissue 4, such as, for example, a circular pattern cut. Edge and contour detection algorithms in OpenCV are used to detect the reference cutting trajectory. Then, the reference trajectory is converted from the image frame to the Cartesian robot frame using a homography transformation. The resulting reference and the real-time positions of robot 20 are used in the trajectory generator and planner to produce multiple equidistant waypoints for the desired trajectory starting from the closest point on the desired trajectory to robot 20. Smooth, time-based desired trajectory segments are produced between the waypoints using, for example, Reflexxes Motion Libraries. Kinematics and Dynamics Library (KDL) in Open Robot Control Systems (OROCOS) may be used, for example, to transform the task-space trajectories of robot 20 to the joint-space trajectories and generate autonomous control command 222. Low level controller 240 then converts autonomous control command 222 to autonomous control signal 221.

Figure 4:
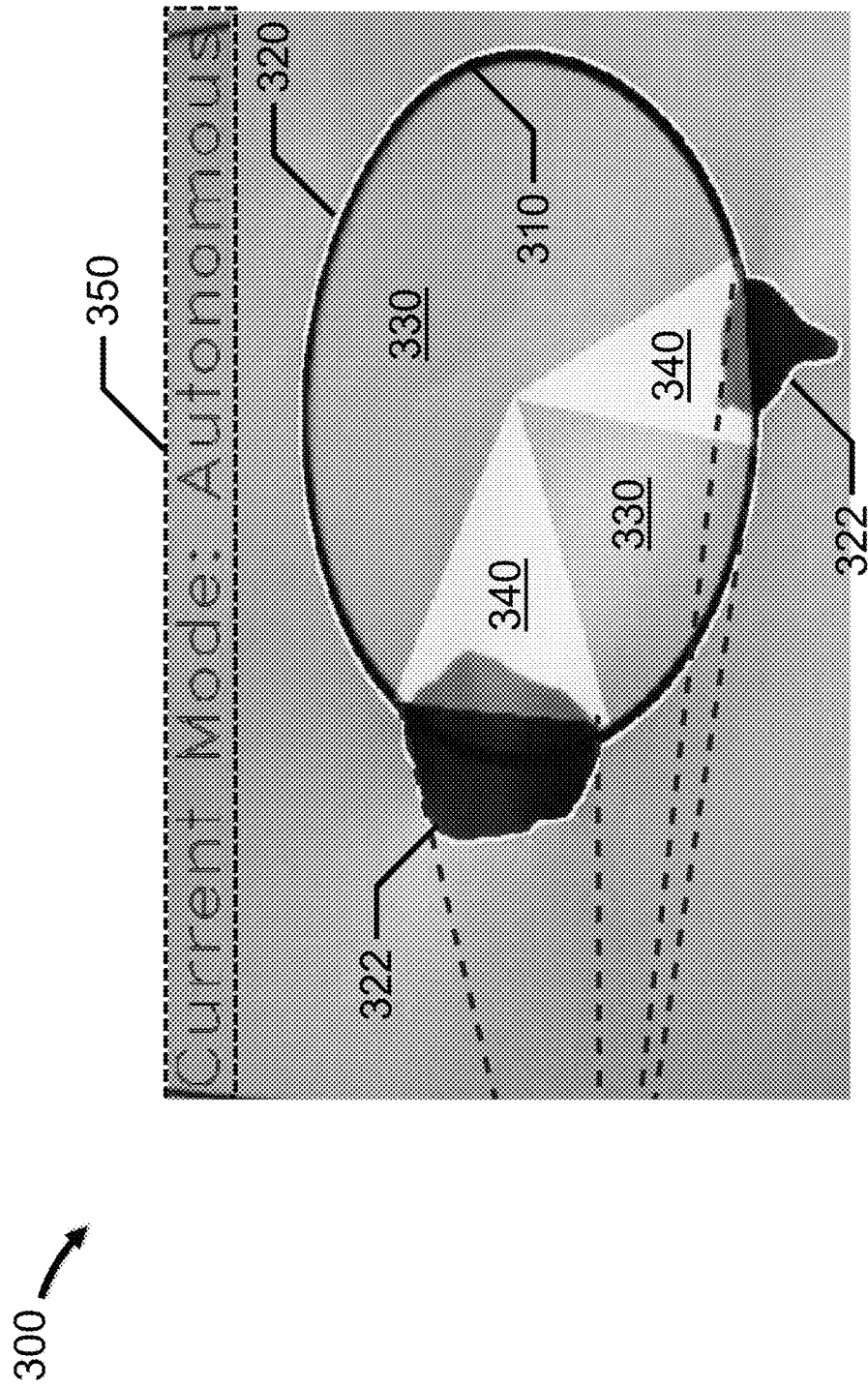
FIG. 4 depicts a graphical user interface for a shared control system, in accordance with an embodiment of the present disclosure.

FIG. 4 depicts a graphical user interface 300 for shared control system 200, in accordance with an embodiment of the present disclosure.

Graphical user interface (GUI) 300 depicts a video image of tissue 4 within task space 2, with reference trajectory 310 for the predetermined task inscribed thereon. GUI 300 also overlays a computer-generated image depicting desired trajectory 320 for the autonomous control mode, one or more suggested autonomous control mode regions 330, one or more suggested manual control mode regions 340, and control mode indicator 350. Suggested autonomous control mode regions 330 and suggested manual control mode regions 340 are determined based on the allocation function α(t). In certain embodiments, the shared control mode automatically switches between autonomous control mode and manual control mode based on the allocation function α(t) during the performance of the predetermined task. In other embodiments, the surgeon manually switches between the control modes, using haptic device 30, during the performance of the predetermined task.

Figure 5:
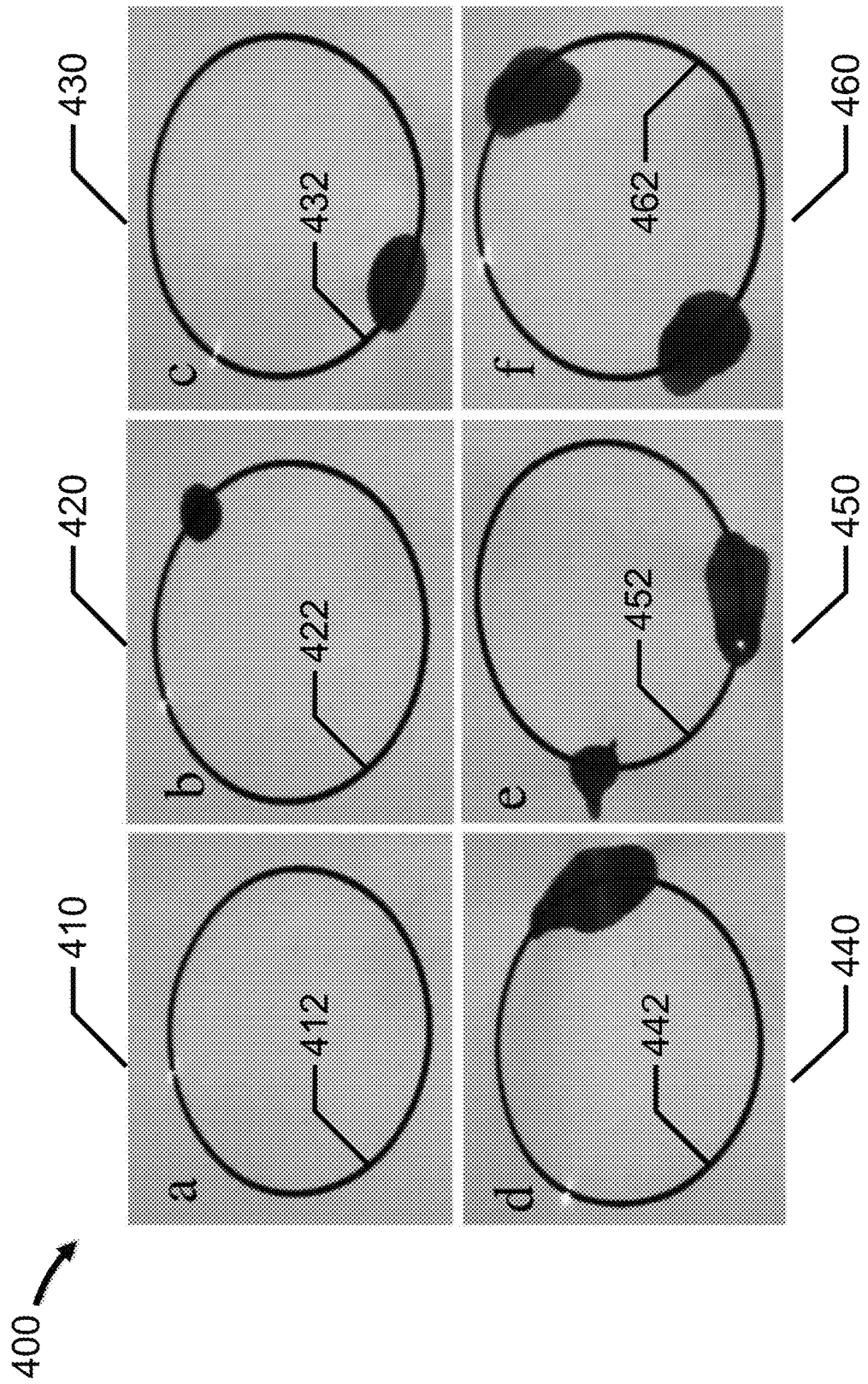
FIG. 5 illustrates a series of tissue samples, in accordance with an embodiment of the present disclosure.

FIG. 5 illustrates a series of tissue samples 400, in accordance with an embodiment of the present disclosure.

As discussed above, in order to determine manual confidence indicator 237 and autonomous confidence indicator 238, a predetermined task is first performed on different tissue samples in both manual control mode and autonomous control mode. In certain embodiments, the predetermined task is a circular pattern cut; other surgical procedures are also contemplated. Tissue samples 400 includes tissue sample 410 without pseudo-blood occlusions and with reference trajectory 412, tissue sample 420 with a small pseudo-blood occlusion and reference trajectory 422, tissue sample 430 with a medium pseudo-blood occlusion and reference trajectory 432, tissue sample 440 with a large pseudo-blood occlusion and reference trajectory 442, tissue sample 450 with a different size pseudo-blood occlusions and reference trajectory 452, and tissue sample 460 with symmetric, medium pseudo-blood occlusions and reference trajectory 462.

In certain embodiments, a laser pointer is attached to tool 24 and used to project a laser dot on tissue samples 400. Performance of the circular cut pattern on tissue samples 400 using a laser pointer attached to tool 24 sufficiently identifies the tracking accuracy of the autonomous and manual control modes. Tool 24 and attached laser pointer follow the desired cutting trajectory for each control mode for each tissue sample 400. In one embodiment, the motion of robot 20 was constrained to a plane parallel to the X-Y plane of tissue samples 400 at a fixed height and orientation to minimize laser-pointing inaccuracies.

In one embodiment, two identification tests are performed on each tissue sample 400. The first identification test performs the circular cut pattern on the tissue sample 400 under manual control mode, and the second identification test performs the circular cut pattern on the tissue sample under autonomous control mode. For each identification test, the actual trajectory of the laser dot is captured by camera 40, and the image data are processed to determine the tracking error of tool 24 by comparing the actual trajectory of the laser dot to the reference trajectory. In this embodiment, the laser dot and the location and size of any pseudo-blood occlusions are detected using functionality provided by the OpenCV library. Perspective transformations are applied to the image data to generate a top view of the laser dot trajectory, and then the image data is mapped to a new image frame that is a square 500×500 pixel plane. In this embodiment, each pixel represents 0.2 mm on the trajectory plane. The location of the laser dot is then tracked using color thresholding and blob detection, and the locations of any pseudo-blood occlusions in that tissue sample are similarly determined. The position of the laser dot is compared to the reference trajectory for that tissue sample, and the tracking error for that identification test is determined.

Figure 6:
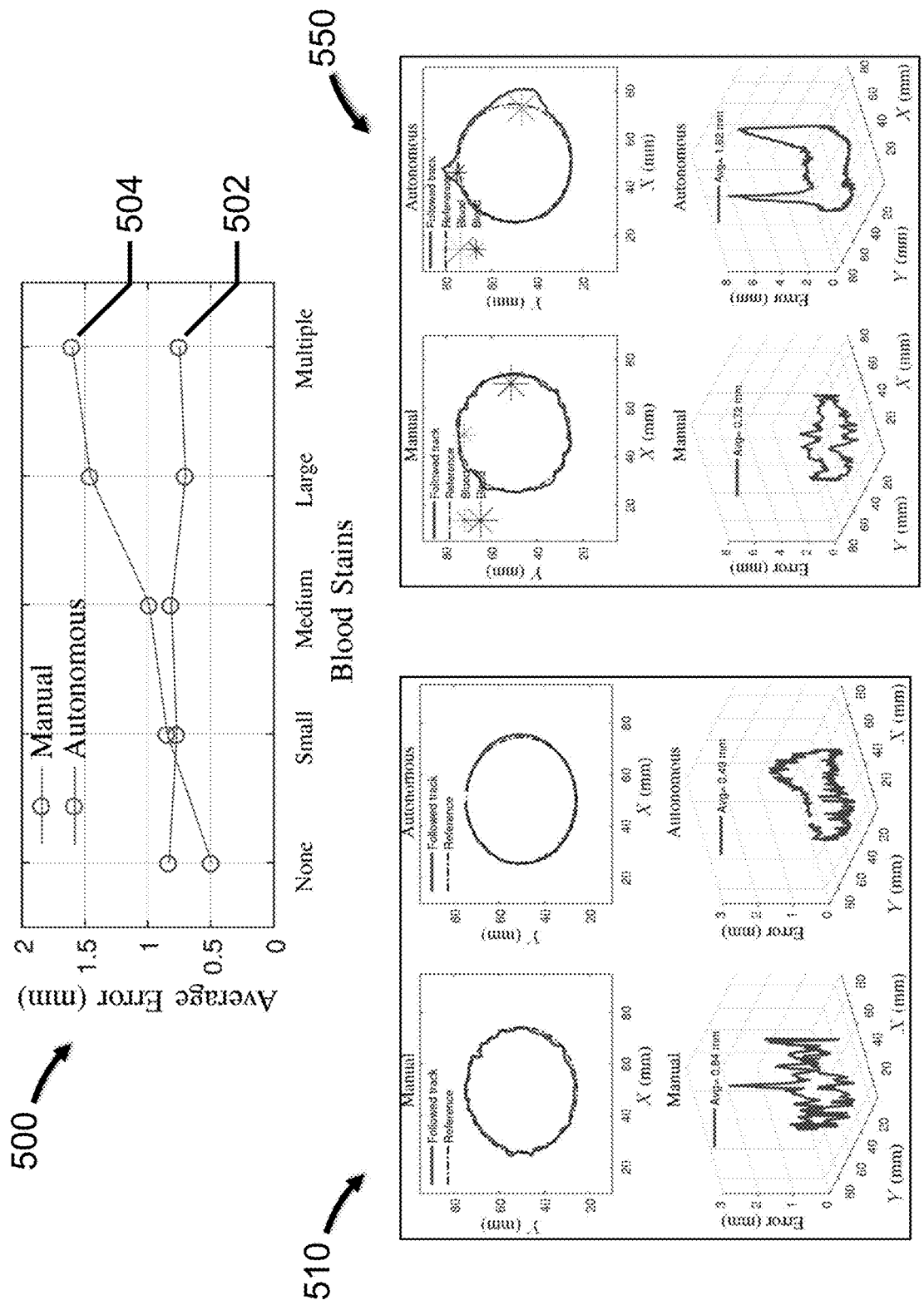
FIG. 6 depicts average tracking error graphs for tissue samples, in accordance with an embodiment of the present disclosure.

FIG. 6 depicts average tracking error graph 500 for tissue samples 400, in accordance with an embodiment of the present disclosure. Also depicted in FIG. 6 are tool trajectory and tracking error graphs 510 for tissue sample 410, and tool trajectory and tracking error graphs 550 for tissue sample 450.

Average tracking error graph 500 depicts average tracking error for manual control mode 502 and average tracking error for autonomous control mode 504 for identification tests performed on tissue sample 410, i.e., "none," tissue sample 420, i.e., "small," tissue sample 430, i.e., "medium," tissue sample 440, i.e., "large," and tissue samples 450, 460, i.e., "multiple."

Tissue sample 410 does not have pseudo-blood occlusions. Average tracking error graph 500 for tissue sample 410 indicate that the autonomous control mode outperforms the manual control mode—the average tracking error for the autonomous control mode was about 0.5 mm, while the average tracking error for the manual control mode was about 0.8 mm. However, as the complexity of the tissue sample increases due to the size and number of pseudo-blood occlusions, the average tracking error of the autonomous control mode increases from about 0.5 mm to about 1.6 mm, while the average tracking error of the manual control mode essentially remains within the same range for all of the samples, i.e., from about 0.6 mm to about 0.8 mm. More particularly, when pseudo-blood occlusions on the desired trajectory interferes with the detection algorithms of the autonomous control mode, the tracking error for the autonomous control mode locally increases near the pseudo-blood occlusions.

Tool trajectory and tracking error graphs 510 present more detailed data for tissue sample 410, including plots of the reference trajectory and the actual trajectory in the X-Y plane, and graphs of the trajectory tracking errors, for the manual control mode and the autonomous control mode. Tool trajectory and tracking error graphs 550 present more detailed data for tissue sample 450, including plots of the reference trajectory and the actual trajectory in the X-Y plane, and graphs of the trajectory tracking errors, for the manual control mode and the autonomous control mode. These data indicate that the local performance of the autonomous control mode on non-occluded regions of each desired trajectory is superior to the local of performance of the manual control mode on these regions. Conversely, the local performance of the manual control mode on occluded regions of each desired trajectory is superior to the local of performance of the autonomous control mode on these regions.

The shared control mode advantageously leverages the local performance strengths of both control modes to provide a more accurate control system by identifying confidence indicators for the autonomous control mode and the manual control mode in the vicinity of the occluded regions. The confidence indicators provide insight on how and when to switch the control modes to improve the overall task performance.

Figure 7:
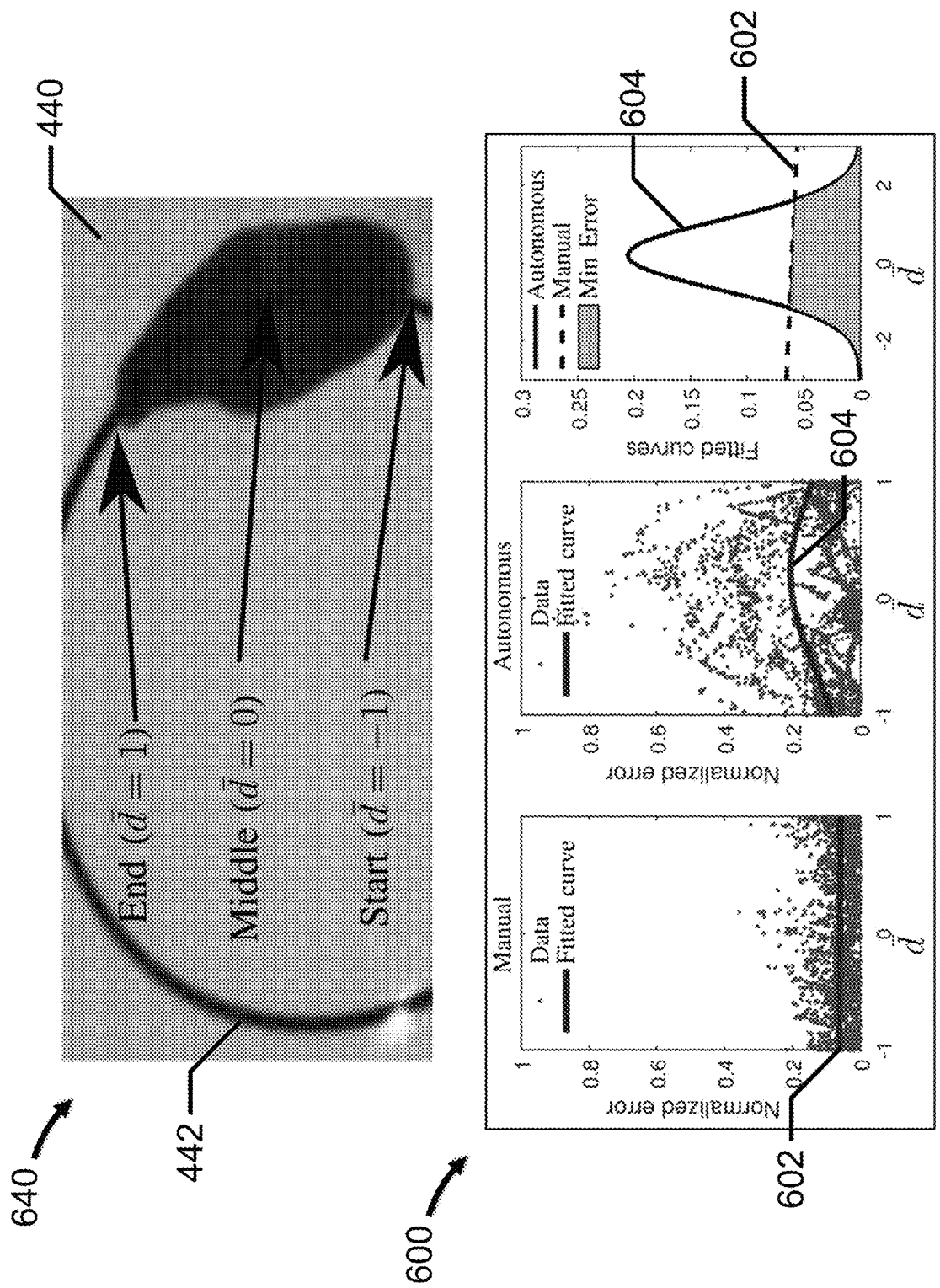
FIG. 7 depicts normalized tracking error graphs, in accordance with an embodiment of the present disclosure.

FIG. 7 depicts normalized tracking error graphs 600, in accordance with an embodiment of the present disclosure. FIG. 7 also depicts annotated tissue sample 640.

To determine the confidence indicators for the manual control mode and the autonomous control mode, in one embodiment, the tracking error data are normalized using a metric related to the size of the occlusion in each tissue sample 400. Other normalization metrics may also be used.

In this embodiment, the normalization metric, d, identifies the intersection of the reference trajectory with the pseudo-blood occlusion. Annotated tissue sample 640 depicts a portion of tissue sample 440 with reference trajectory 442, and several values for d. When approaching the pseudo-blood occlusion along the reference trajectory, the start of the pseudo-blood occlusion is defined as $d=-1$, the middle of the pseudo-blood occlusion is defined as $d=0$, and the end of the pseudo-blood occlusion is defined as $d=1$. Using these definitions, the intersection of the reference trajectory with pseudo-blood occlusions is normalized based on the size of the occlusion. In one embodiment, OpenCV blob detection algorithms are used to find the location and size of the pseudo-blood occlusions or blobs on the reference trajectory, and to normalize their intersections. The tracking error along d for each identification test was determined and normalized based on the blob sizes. Other blob detection algorithms are also contemplated.

The performances of autonomous control mode and the manual control mode, over all of the identification tests, are then analyzed based on the normalized proximity to the pseudo-blood occlusions. After the tracking error data is normalized for each control mode, a curve is fitted to each normalized control mode tracking error data set. In one example, the fitted curve for the manual control mode is a linear function, i.e., manual control mode curve 602, while the fitted curve for the autonomous control mode is a skewed Gaussian function, i.e., autonomous control mode curve 604. In this example, the fitted function for the manual control mode is governed by Equation 2, while the fitted function for the autonomous control mode is governed by Equation 3.

$$y_M = a_M \, d + b_M \tag{2}$$
with $a_M = -0.002$ and $b_M = 0.061$ $$y_A = a_A e^{\left(\frac{d-b_A}{c_A}\right)} \tag{3}$$
with $a_A = 0.206$, $b_A = 0.213$, $c_A = 1.257$ Normalized tracking error graphs 600 include manual control mode normalized tracking error data, autonomous control mode normalized tracking error data, and the fitted curves for each data set.

These data suggest that the manual control mode is effective in pseudo-blood occlusion regions, while the autonomous control mode is more effective elsewhere. Based on these data, the confidence indicator for manual control mode is defined as $C_M=1-y_M$, and the confidence indicator for the autonomous control mode is defined as $C_A=1-y_A$.

Figure 8:
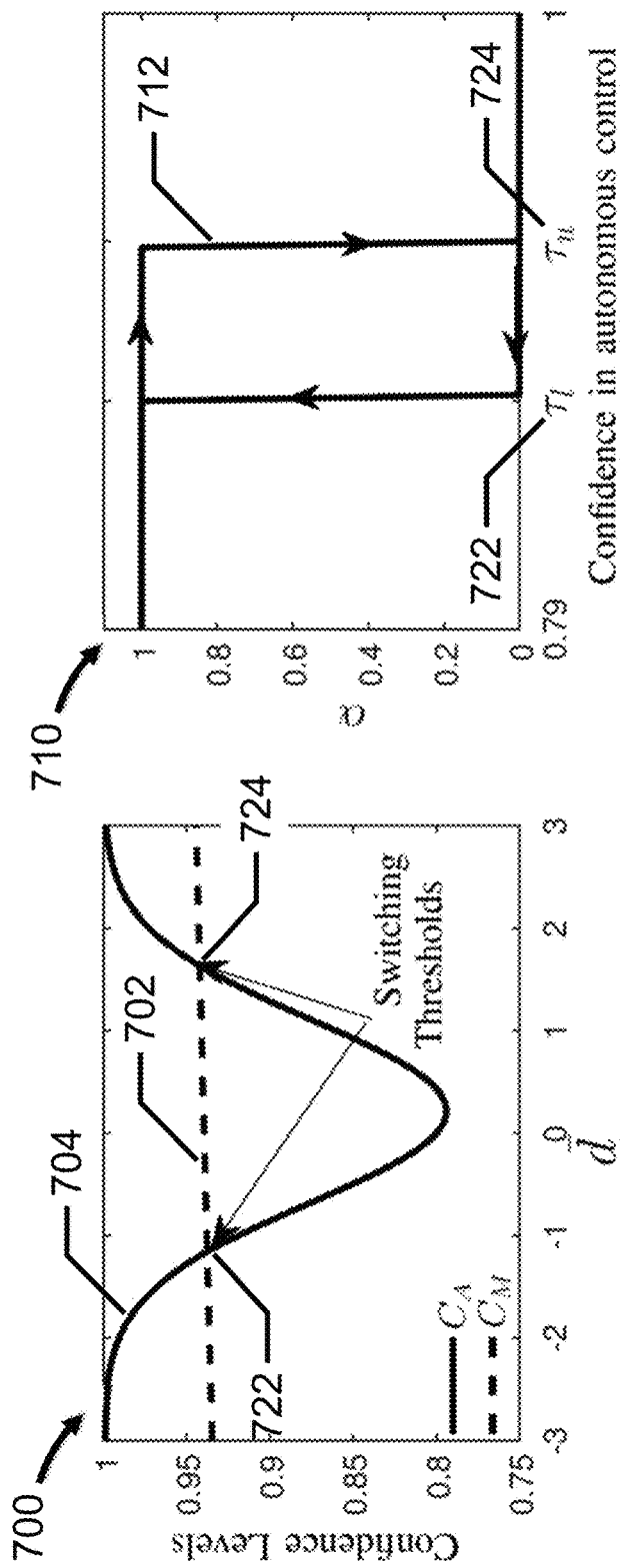
FIG. 8 depicts a confidence indicator graph and an allocation function graph, in accordance with an embodiment of the present disclosure.

FIG. 8 depicts confidence indicator graph 700 and allocation function graph 710, in accordance with an embodiment of the present disclosure.

Confidence indicator graph 700 depicts manual control mode confidence indicator 702 and autonomous control mode confidence indicator 704 for the experimental tests described above. After confidence indicators 702, 704 are determined, the allocation function α(t) is generated based on these confidence indicators. In one embodiment, confidence indicators 702, 704 are used to locally select the most reliable control mode as the predetermined task is performed. Because confidence indicator 702 is more or less constant, the allocation function α(t) and the decision thresholds for locally switching between manual control mode and autonomous control mode are determined based on confidence indicator 704.

Referring to the confidence indicator graph 700, as d approaches 0 from negative values, confidence indicator 704 is greater than confidence indicator 702. In other words, confidence in the autonomous control mode is greater than the manual control mode. As confidence indicator 704 gradually decreases from 1, a lower decision threshold, $T_{lower}$ 722, is reached at the point where confidence indicator 704 intersects confidence indicator 702 ($T_{lower}=0.93$ at $d=-1.15$). As the middle of the pseudo-blood occlusion is approached (d~0), confidence in the autonomous control mode reaches a minimum level ($T_{minimum}$ 0.79), and then begins to increase until upper decision threshold $T_{upper}$ 724 is reached at the point where confidence indicator 704 intersects confidence indicator 702 ($T_{upper}=0.94$ at $d=1.6$). Between $T_{lower}$ 722 and $T_{upper}$ 724, confidence indicator 702 is greater than confidence indicator 704. In other words, confidence in the manual control mode is greater than the autonomous control mode. As d approaches positive values after $T_{upper}$ 724, confidence indicator 704 is greater than confidence indicator 702 and gradually increases back to 1. In other words, confidence in the autonomous control mode is again greater than the manual control mode.

Allocation function graph 710 depicts allocation function 712, which is a function of the confidence in the autonomous control mode, i.e., confidence indicator 704.

In this embodiment, allocation function 712 returns a value of 0 or 1 based on the value of confidence indicator 704. Referring to Equation 1, the value 0 indicates that the autonomous control mode has been selected for the shared control mode, and the value 1 indicates that the manual control mode has been selected for the shared control mode. In one example, the shared control mode is initially set to the autonomous control mode, and allocation function 712 has an initial setting of 0. As tool 24 approaches the beginning of a pseudo-blood occlusion in tissue 4, the normalized distance d approaches lower decision threshold $T_{lower}$ 722. When tool 24 crosses $T_{lower}$ 722, allocation function 712 returns the value 1, which changes the shared control mode to the manual control mode. As tool 24 approaches the end of the pseudo-blood occlusion in tissue 4, the normalized distance d approaches upper decision threshold $T_{upper}$ 724. When tool 24 crosses $T_{upper}$ 724, allocation function 712 returns the value 0, which changes the shared control mode back to the autonomous control mode.

Figure 10A:
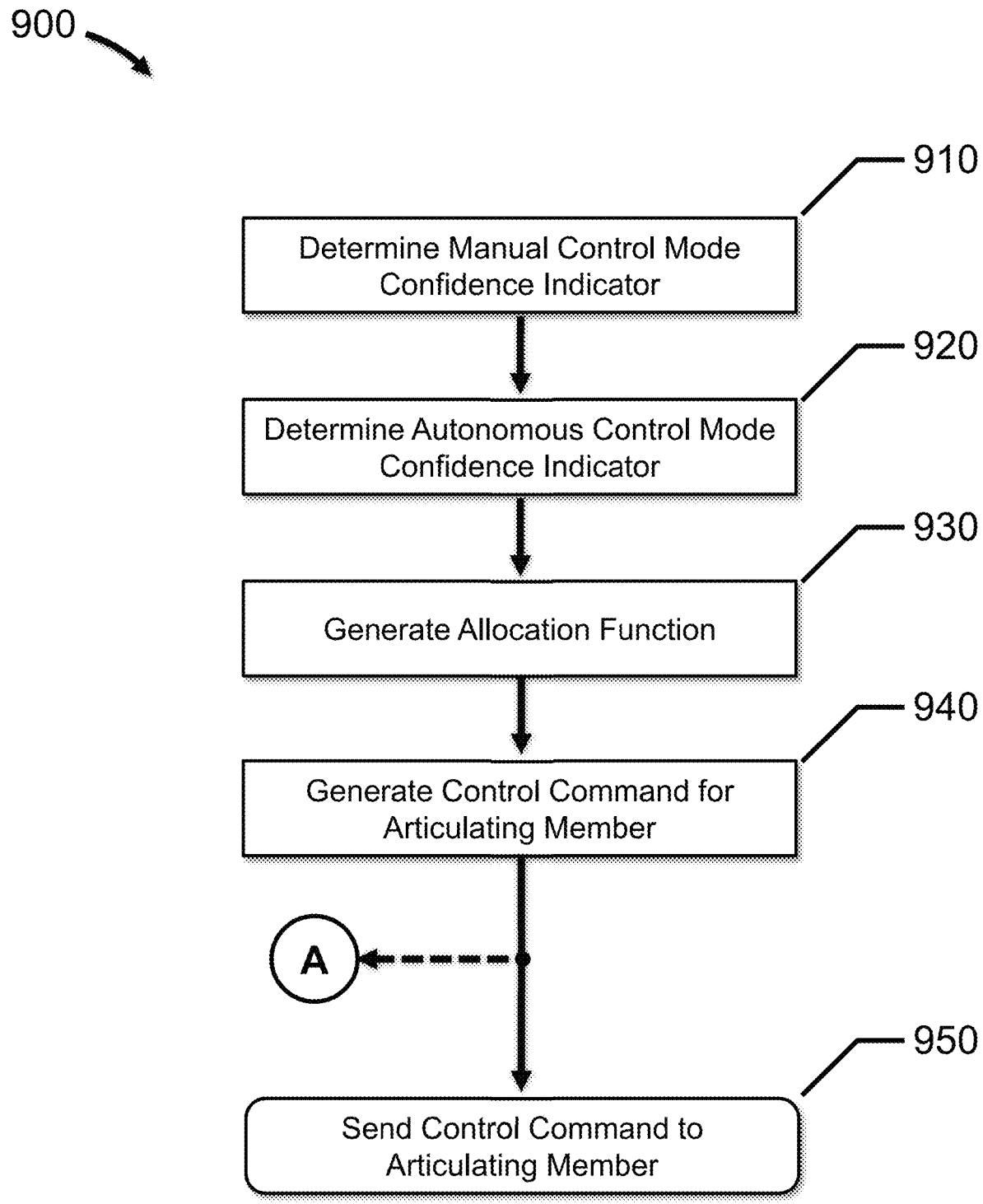
FIGS. 10A and 10B present flow diagrams depicting at least some of the functionality of the shared control module depicted in FIG. 2, in accordance with embodiments of the present disclosure.
Figure 10B:
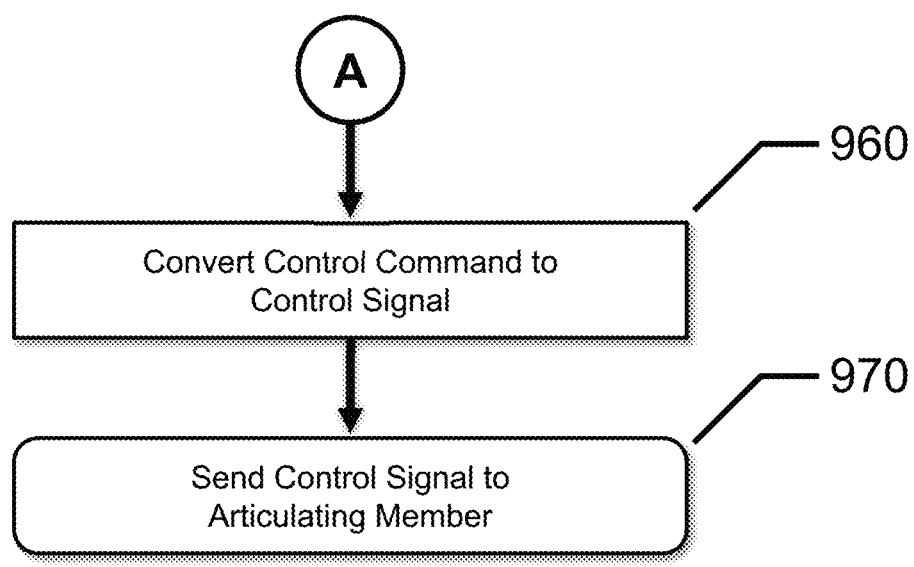

FIGS. 10A and 10B present flow diagrams depicting at least some of the functionality of shared control module 134 depicted in FIG. 2, in accordance with embodiments of the present disclosure FIG. 10A presents a flow diagram for controlling an articulating member including a tool, in accordance with an embodiment of the present disclosure.

At 910, a manual control mode confidence indicator is determined based on a manual control mode for the articulating member of the robot. As discussed above, tracking error data are acquired during the performance of a predetermined task under the manual control mode. The tracking error data represent the deviations between a reference trajectory and the actual trajectory of the tool. The manual control mode confidence indicator is determined based on this tracking error data. In one embodiment, the tracking error data may be normalized using a metric associated with the predetermined task, such as, for example, occlusion size, and then a curve may be fitted to the data to produce a normalized tracking error function. The manual control mode confidence indicator is then derived from the normalized tracking error function.

At 920, an autonomous control mode confidence indicator is determined based on an autonomous control mode for the articulating member of the robot. As discussed above, tracking error data are acquired during the performance of a predetermined task under the autonomous control mode. The tracking error data represent the deviations between a reference trajectory and the actual trajectory of the tool. The autonomous control mode confidence indicator is determined based on this tracking error data. In one embodiment, the tracking error data may be normalized using a metric associated with the predetermined task, such as, for example, occlusion size, and then a curve may be fitted to the data to produce a normalized tracking error function. The autonomous control mode confidence indicator is then derived from the normalized tracking error function.

At 930, an allocation function is generated based on the manual control mode confidence indicator and the autonomous control mode confidence indicator. As discussed above, the manual and autonomous control mode confidence indicators are used to locally select the most reliable control mode as the predetermined task is performed. For example, if the manual control mode confidence indicator is more or less constant, the allocation function $\alpha(t)$ and the decision thresholds for locally switching between manual control mode and autonomous control mode may be determined based on the autonomous control mode confidence indicator. Conversely, if the autonomous control mode confidence indicator is more or less constant, the allocation function $\alpha(t)$ and the decision thresholds for locally switching between manual control mode and autonomous control mode may be determined based on the manual control mode confidence indicator. In another example, the manual and autonomous control mode confidence indicators are blended to yield an allocation function $\alpha(t)$ that combines control commands from the manual control mode and control commands from the autonomous control mode.

At 940, a control command is generated for the articulating member of the robot based on the allocation function. As discussed above, when $\alpha(t)$ is 0, the autonomous control command A(t) is selected as the control command. In other words, the control command is not influenced by the manual control command when $\alpha(t)$ is 0. Conversely, when $\alpha(t)$ is 1, the manual control command M(t) is selected as the control command. In other words, the control command is not influenced by the autonomous control command when $\alpha(t)$ is 1. When $\alpha(t)$ is a number between 0 and 1, the manual control command and the autonomous control command are blended, based on the value of the allocation function $\alpha(t)$, to generate the control command. As discussed above, the allocation function $\alpha(t)$ changes as a function of the independent variable x. For example, the independent variable x may be the confidence in the autonomous control mode, as discussed above.

At 950, the control command is sent to the articulating member. As discussed above, in one embodiment, the control command is input to a low level controller, which converts the control command to a robot-specific control signal. The robot-specific control signal is then sent to the robot over the appropriate I/O Interface. In another embodiment, the control command is sent directly to the robot, which converts the control command to the appropriate robot-specific control signal.

Figure 16:
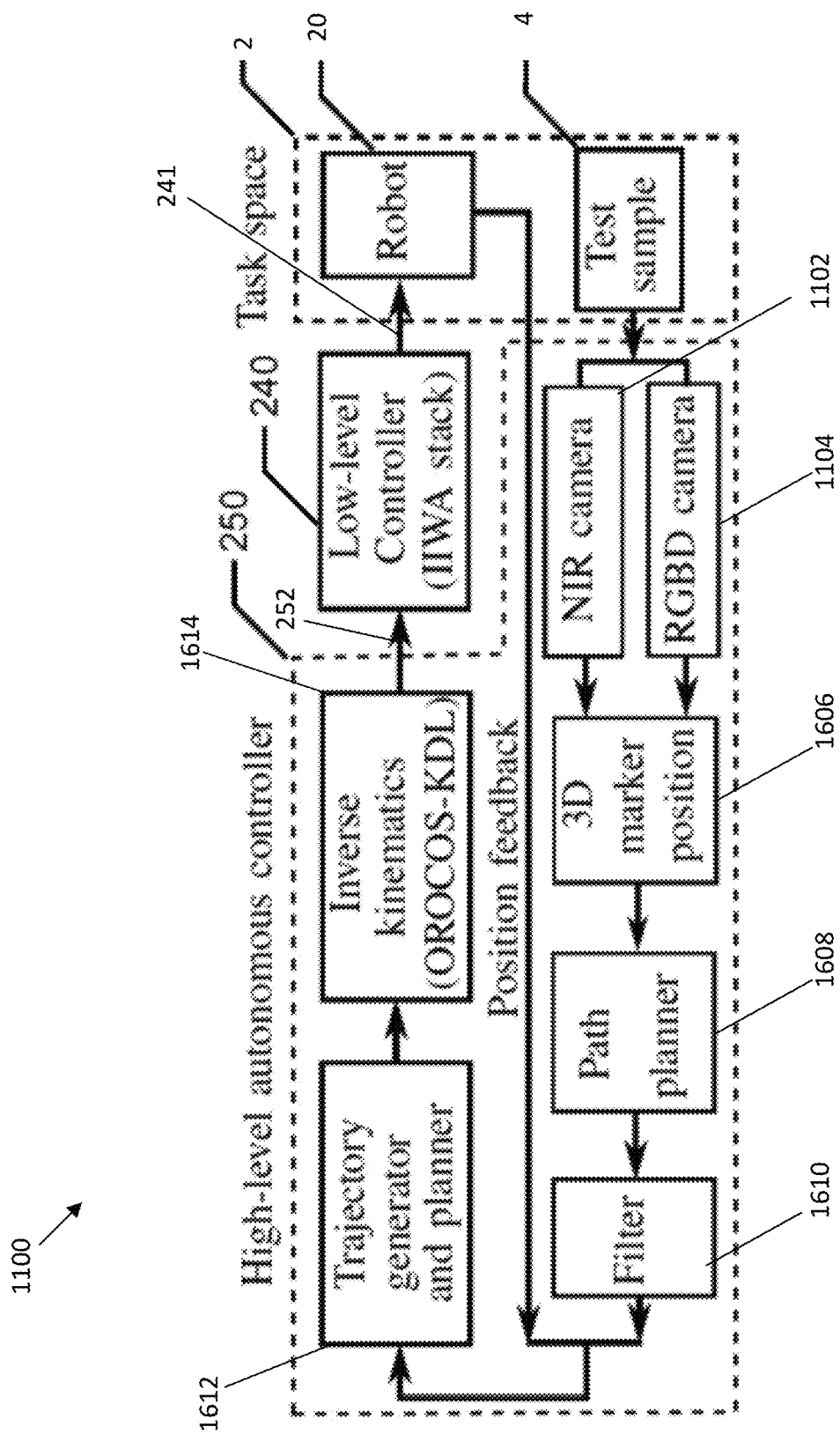
FIG. 16 shows an illustrative block diagram corresponding to a portion of the RAS system of FIG. 11, including a supervised autonomous control subsystem and low level controller, in accordance with embodiments of the present disclosure.

It should be understood that the "autonomous control mode" referred to in connection with claim 10A may correspond to a fully autonomous control mode (e.g., in connection with subsystem 220 of FIG. 3D) or to a supervised autonomous control mode (e.g., in connection with subsystem 250 of FIG. 16).

FIG. 10B presents a flow diagram for controlling an articulating member including a tool, in accordance with an embodiment of the present disclosure.

At 960, the control command is converted to a robot-specific control signal, as discussed above.

At 970, the control signal is sent to the articulating member, as discussed above.

FIGS. 11-18 depict various features of an RAS system, in accordance with the present disclosure.

Generally, surgical imaging is challenging, particularly when it comes to intra-operative tracking of soft tissue. During the surgery, a variety of inevitable and unpredictable factors such as breath, heartbeat, patient movements and interventional surgical procedures cause organ shifts and tissue deformation. The direct vision of an MIS surgical scene may be obstructed by the patient's body, such as in head and neck cancer surgeries. The oral cavity squamous cell carcinoma (OSCC) and oropharyngeal squamous cell carcinoma (OPSCC) are the two most common cancers in the head and neck region, and minimally invasive transoral robotic surgery (TORS) is an effective therapeutic method for their removal. Pre-operative examination with flexible endoscopy, computed tomography (CT) and magnetic resonance imaging (MRI) may be used to identify the tumor margins. Narrow-band imaging (NBI) with only green and blue light to highlight the malignant lesions improves the identification of disease-free resection margins, and is an alternative to white light (WL) endoscopy. Based on pre-operative images, surgeons can mark the tumor margins with ink and use them as references during the resection while receiving 2D/3D and WL/NBI visual feedback from the endoscope. However, the marked tumor margins can easily get obscured by blood and charred tissue when observing the surgery on a video display.

As will be described, biocompatible near-infrared (NIR) markers may be used for robot guidance in these and other surgical situations, and provide strong penetration of the NIR light, durability, and bio-compatibility. More specifically, by observing the NIR light with higher wavelength than the visual light, the NIR markers can always be seen intra operatively with high signal to noise ratio (SNR), even when obstructed by blood and tissue. In long-term multi-modality tumor treatment scenarios, several rounds of chemotherapy are performed before the surgery and the tumor dimension shrinks over time. In one embodiment, the location of the tumor is marked before chemotherapy, which provides surgeons with the original tumor region intra-operatively rather than the shrunken tumor post chemotherapy.

In some embodiments, NIR markers described herein may made from FDA-approved NIR fluorophore Indocyanine Green (ICG), cyanoacrylate (Dermabond) and acetone. Once the marker is injected into the tissue, it forms a solid long lasting bead. NIR markers may be used on target tissue locations for suture planning via linear interpolation as well as 2D pattern cutting for pseudo-tumor resection. Additionally, NIR markers may be used on soft and unstructured 3D tissues in combination with more complex control methods compared to the 2D scenario. In some embodiments, a single point cloud of a tissue surface may be acquired (e.g., using a NIR camera, a RGBD camera, or a combination of the two), and a straight-line, 3D incision path for the robot may be determined. The start and end points may be manually selected in some embodiments.

Figure 11:
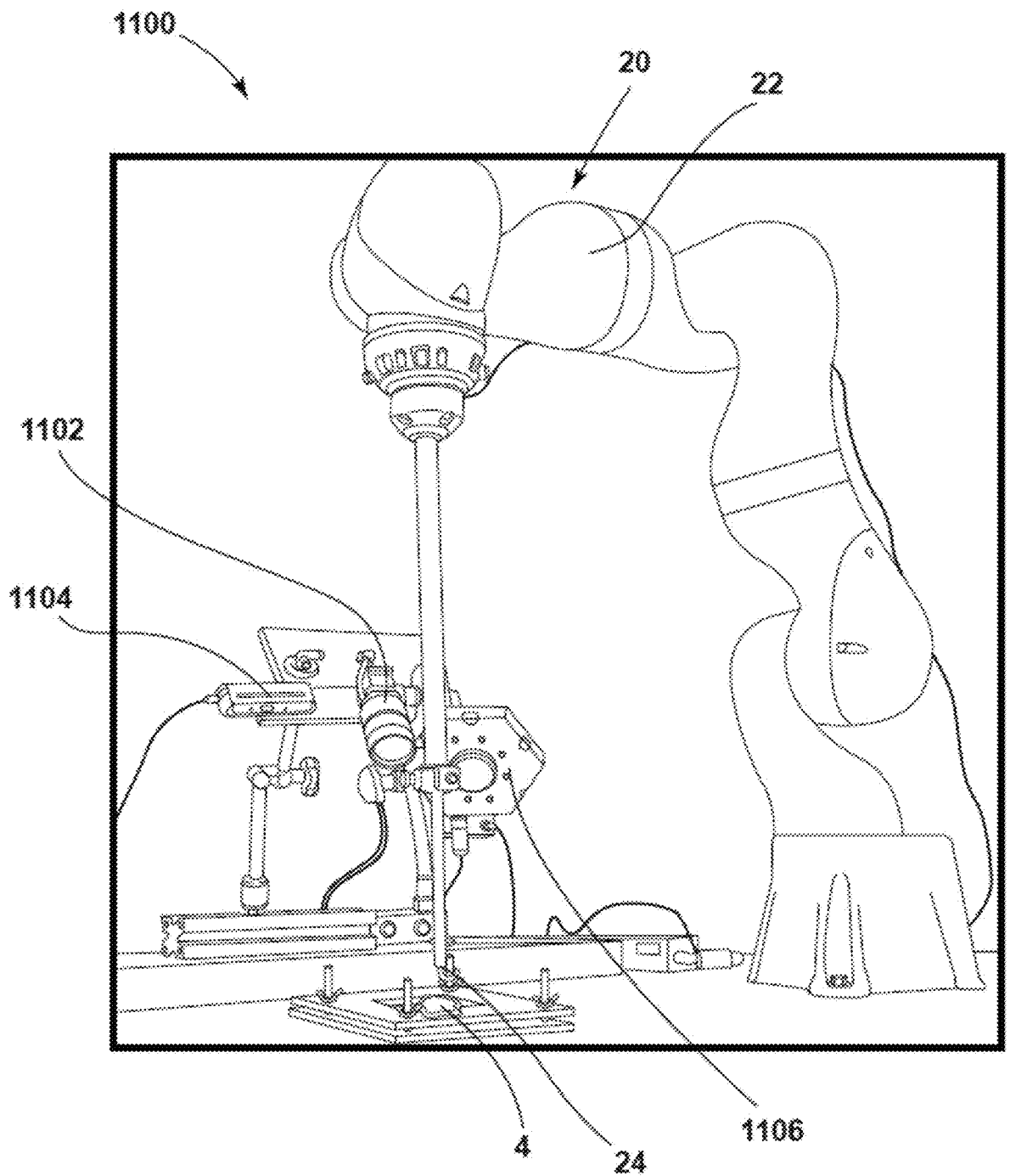
FIG. 11 shows an illustrative RAS system having a dual camera system, in accordance with embodiments of the present disclosure.

FIG. 11 shows an illustrative RAS system 1100 that is included in a testbed. The RAS system 1100 may include a robot 20 having a robotic arm 22 (e.g., a 7-DOF KUKA lightweight robotic arm), a near-infrared (NIR) camera 1102 (e.g., which may be a 845 nm±55 nm NIR camera), a Red-Green-Blue-Depth (RGBD) camera 1104 (e.g., which may be a Realsense D415 RGBD camera), a light source 1106 (e.g., which may be an infrared or NIR light source, and which may include a 760 nm high power light emitting diode), and an electrocautery tool 24. Examples of various functions of the RAS system 1100 will be illustrated with respect to a tissue sample 4.

In at least some ways, the RAS system 1100 may correspond to the RAS system 10 of FIGS. 1 and 2, but with a dual camera imaging system that includes the cameras 1102 and 1104 instead of the camera 40, which may allow for 3D and NIR imaging. Components of the RAS system 1100 having counterparts in the RAS system 10 may be referred to with the same reference numerals. Accordingly, some details of the RAS system 1100 are were already described in connection with RAS system 10 are not repeated here for the sake of brevity.

As will be described, the NIR camera 1102 and the RGBD camera 1104 may be included in a supervised autonomous control subsystem 250 (e.g., which may correspond to the supervised control subsystem 250 shown of FIG. 3), shown in FIG. 16, of a shared control system that includes the robot 20. The subsystem 250 may control the robot 20 and electrocautery tool 24 to produce precise and consistent incisions on complex three-dimensional (3D) soft tissues, such as the tissue sample 4. The supervised autonomous control subsystem 250 may provide a supervised autonomous control mode in which an operator (e.g., a surgeon) may identify key points on a tissue of interest, such as, for example, a tumor, by selecting the NIR markers outlining the tumor using a GUI. In the supervised autonomous control mode, the operator may validate the electrocautery path before autonomous control is initiated. The subsystem may autonomously generate and filter a complete 3D electro-surgery pattern between multiple key points marking the tumor bed. Since the path planning and filtering is done via continuous and multiple measurements of the 3D tissue surface information, the resulting executed incision may be more accurate than a conventional single-step, offline path planning method. Compared to 2D image-based visual serving, the supervised autonomous control mode may provide a more accurate 3D incision on real tissues, including a more accurate depth of cut.

Electrocautery tool 24 may be added to robot 20 for performing incisions on the tissue samples. Electrocautery tool 24 may use a needle electrode to send a cutting waveform, which may be generated via an electro-surgical generator (e.g., an DRE ASG-300 electro-surgical generator), to the target tissue. The cutting waveform may vaporize tissues in contact with the electrode.

Figure 12A:
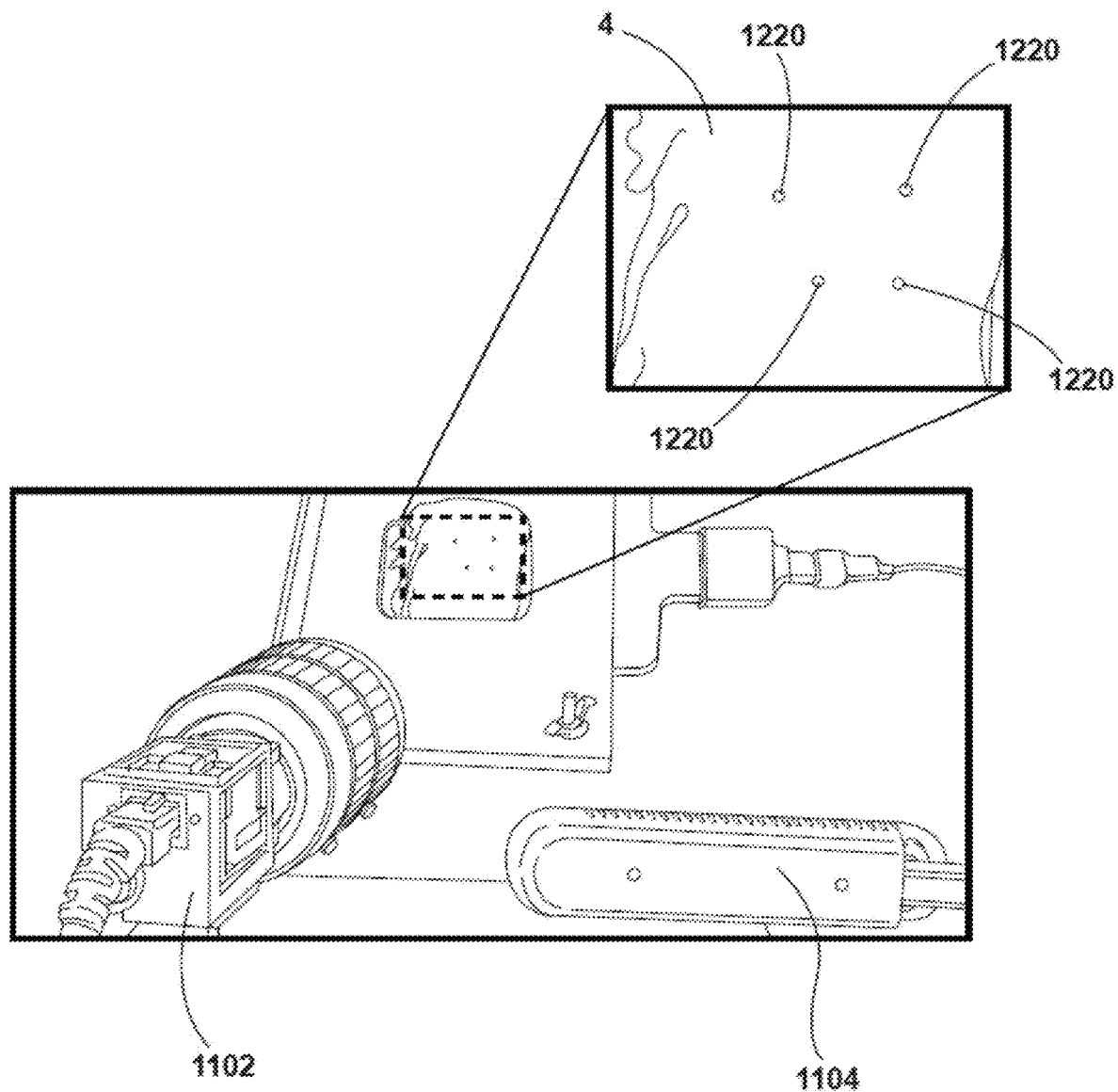
FIG. 12A shows a perspective view of a testbed of the RAS system of FIG. 11, in accordance with embodiments of the present disclosure.

FIG. 12A shows a perspective view of the testbed of FIG. 11 and the dual camera imaging system of the RAS 1100 that includes the NIR camera 1102 and the RGBD camera 1104. The dual camera system may detect: NIR markers 1220 disposed in or on the tissue sample 4, their 3D positions, a tissue surface (e.g., of tissue sample 4), and a manual control interface for result comparisons. The RGBD camera 1104 may obtain 3D tissue surface information. The NIR camera 1102 may detect the NIR markers 1220 when they are illuminated by the light source 1106. In some embodiments, other 3D cameras, such as plenoptic cameras and structured illumination cameras, may be used instead of or in addition to the RGBD camera 1104.

In some embodiments, in order to prevent interference of the projector of the RGBD camera 1104 with the readings captured by the NIR camera 1102, the projector may be periodically switched back and forth between on and off states (e.g., with a state transition occurring every 0.22 seconds) via software triggers that control the RGBD camera 1104. The NIR camera 1102 may be configured to capture images only when the projector of the RGBD camera 1104 is turned off.

A real-time imaging system (e.g., which may be included in subsystem 250 of FIG. 16) may extract the 3D position of the biocompatible NIR markers 1220 by ray tracing the positions of the NIR markers 1220 via a co-registered point cloud generated by the RGBD camera 1104. The positions of the RGBD camera 1104 and the NIR camera 1102 may be compared to a checkerboard, and relative positions of the cameras with respect to each other may be determined (e.g., using the "transform package in Robot Operating System (ROS)). A hand-eye calibration may be performed by finding the position of the checkerboard in the robot coordinates. The 3D position and orientation of the cameras 1102, 1104 compared to the robot 20 are then determined. A visual serving platform (VISP) may be used to track portions of the NIR images captured by the NIR camera 1102 corresponding to the NIR markers 1220 between NIR image frames captured by the NIR camera. The operator may select the markers via mouse clicks (e.g., with a mouse of the I/O devices 142 of the computer 100 shown in FIG. 2). It should be understood that while NIR cameras, NIR images, and NIR markers are described, these elements are intended to be illustrative and not limiting. In alternate embodiments, other suitable camera types, image types, and/or marker types may be used in place of the NIR camera 1102, the NIR image data, and the NIR markers 1220 to provide landmark/feature detection as a basis for path planning.

Figure 12B:
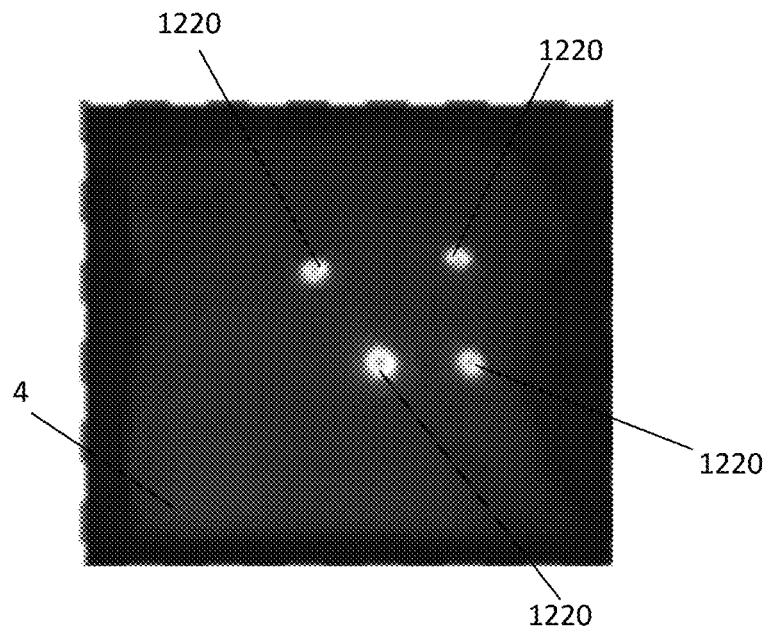
FIG. 12B shows an illustrative image of sample tissue and near-infrared (NIR) markers captured by an NIR camera of the RAS system, in accordance with embodiments of the present disclosure.

FIG. 12B shows an illustrative image captured by the NIR camera 1102, showing the NIR markers 1220 disposed on the tissue sample 4.

Figure 12C:
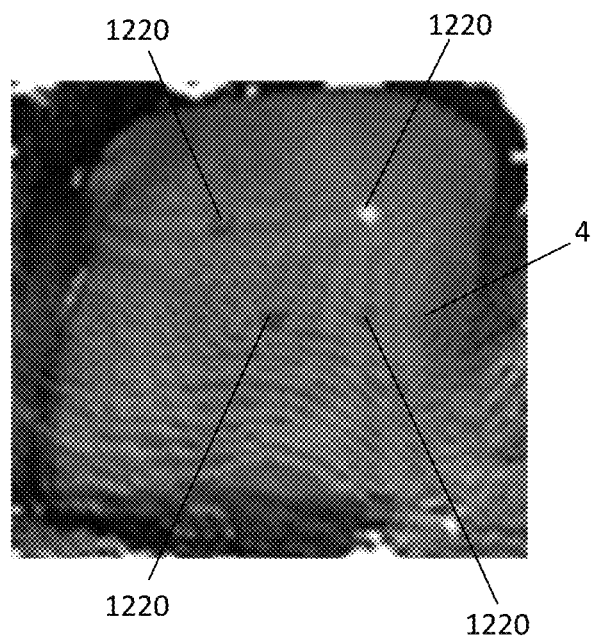
FIG. 12C shows an illustrative point cloud image of the tissue sample captured by a RGBD camera of the RAS system with positions of NIR markers overlaid on the point cloud image, in accordance with embodiments of the present disclosure.

FIG. 12C shows an illustrative point cloud image of the tissue sample 4 captured by the RGBD camera 1104. In the present example, the point cloud image has been overlaid with the 3D positions of the NIR markers 1220 (e.g., by the subsystem 250).

Figure 13:
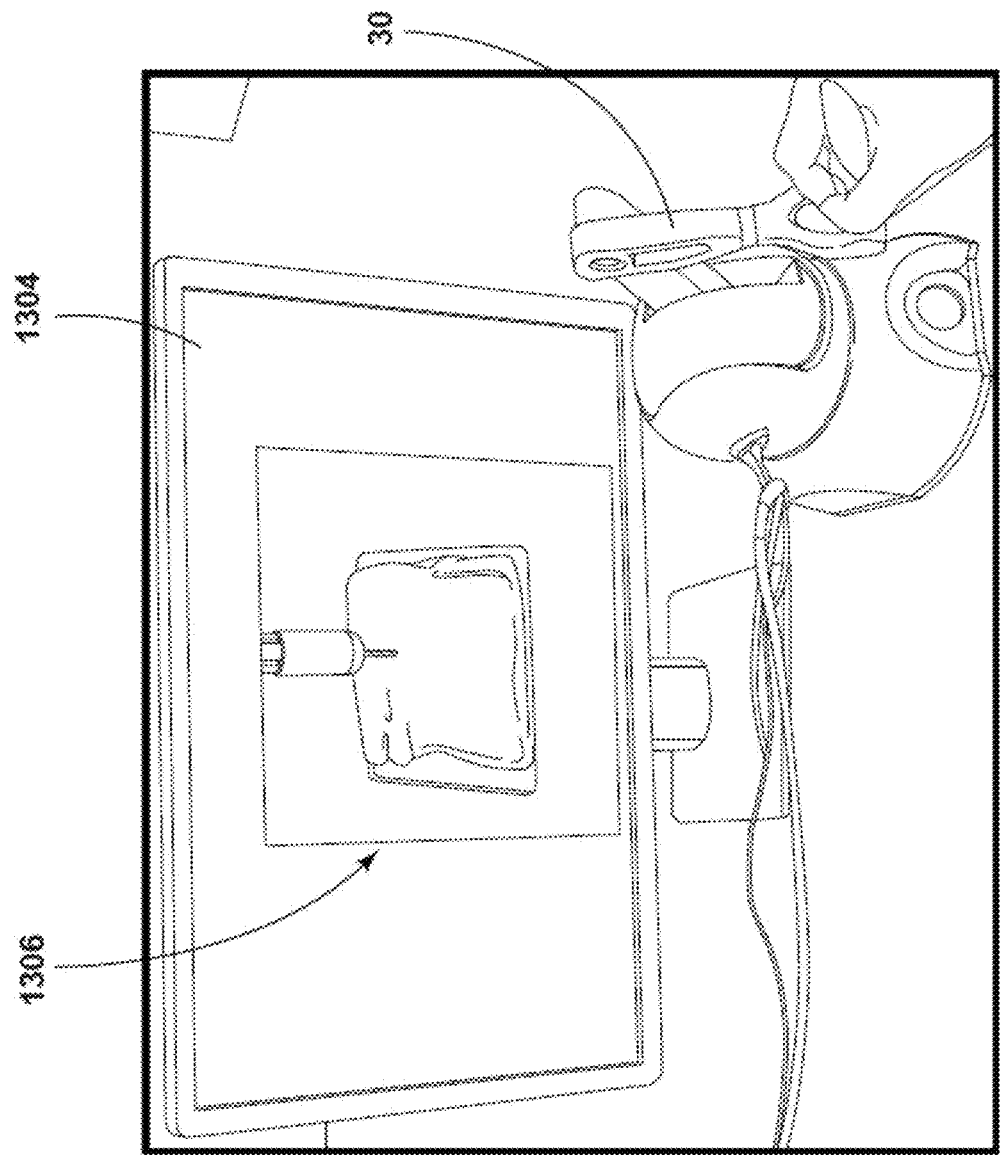
FIG. 13 shows illustrative system components which may be used in connection with a manual control mode of the RAS system, in accordance with embodiments of the present disclosure.

In one embodiment, supervised autonomous control subsystem 210 may include a manual control mode, some aspects (e.g., system components) of which are shown in FIG. 13. Using this interface, a surgeon manually controls the 3D motion of the tool-tip of the robot 20 using the input device 30. The coordinate frame transformations between input device 30, the camera view frame, and the robot frame are done in real-time via the ROS transform package, which matches all the motions that supervised autonomous control subsystem 250 may perform. Camera 40 provides high-resolution real-time visual feedback to the surgeon, and the NIR marker positions are overlaid on this view (e.g., green dots shown in FIG. 12C) as a reference for the surgeon. In such embodiments, a third camera (not shown), which may be an RGB camera (e.g., camera 40 of FIG. 1), may be included in the RAS system 10, and may capture high-resolution video 1306, which is displayed on the monitor 1304 (e.g., which may correspond to the display 50 of FIG. 1) to provide real-time visual feedback to the operator. The positions of NIR markers 1220 (e.g., having been previously identified from the NIR image(s) and point cloud image(s) captured by the cameras 1102 and 1104, respectively) may be overlaid over the video 1306.

Figure 14A:
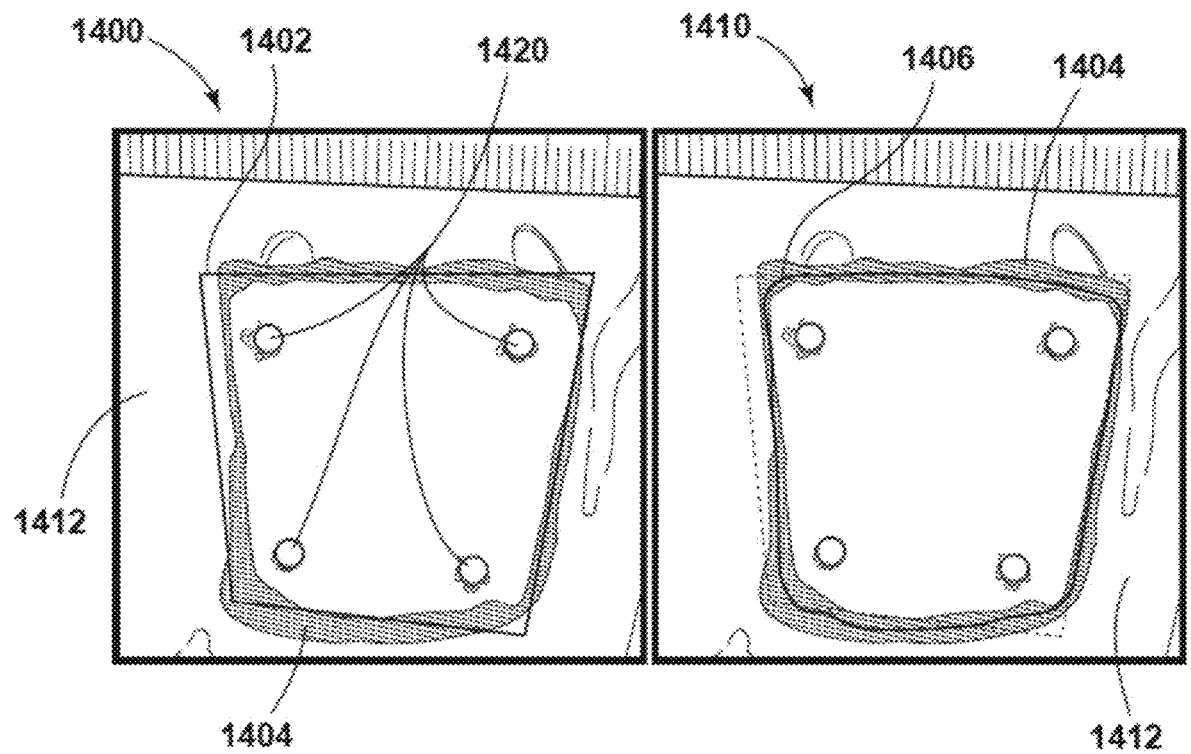
FIG. 14A shows illustrative overlays 1400 and 1410 corresponding to an exemplary manual cutting task that may be performed using the RAS system of FIG. 11, in accordance with embodiments of the present disclosure.
Figure 14B:
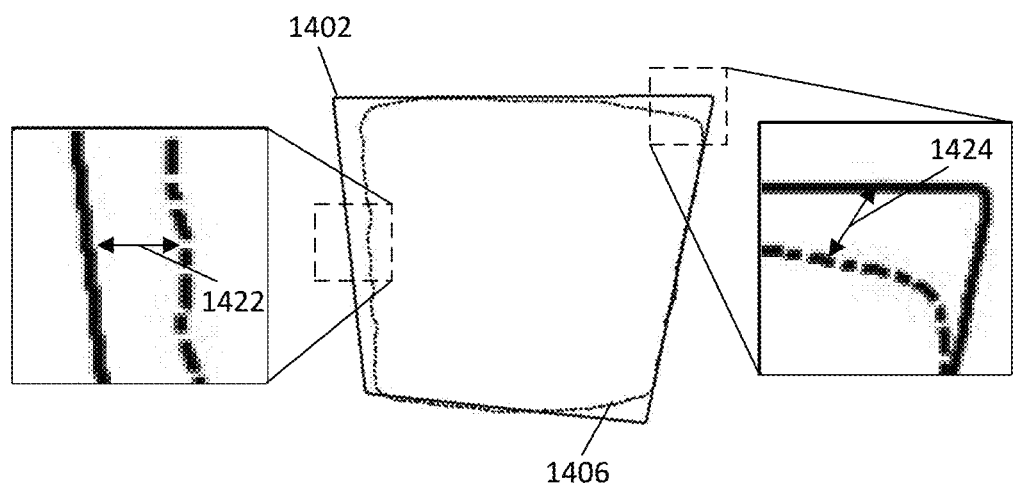
FIG. 14B shows an illustrative comparison between a desired incision path and an actual incision path, which may be use to evaluate error following the cutting task, in accordance with embodiments of the present disclosure.

FIG. 14A depicts illustrative overlays 1400 and 1410 corresponding to an exemplary cutting task that uses 4 NIR markers 1420. Overlay 1400 depicts the desired incision pattern 1402 and an incision path 1404 on a tissue sample 1412 (e.g., which may correspond to tissue sample 4 of FIG. 11). The tissue sample 1412 may have been cut using subsystem 210, 220, 250, or a combination of these. Overlay 1410 depicts an approximation 1406 of corresponding edges of the incision path 1404, which may be compared to the desired incision path 1402 for surface error measurement. FIG. 14B shows an example comparison between the desired incision pattern 1402 and the approximation 1406. Two regions are shown in higher resolution to illustrate surface error 1422 and 1424. The comparison may be performed by a post-processing system (not shown) in order to estimate error.

Figure 15A:
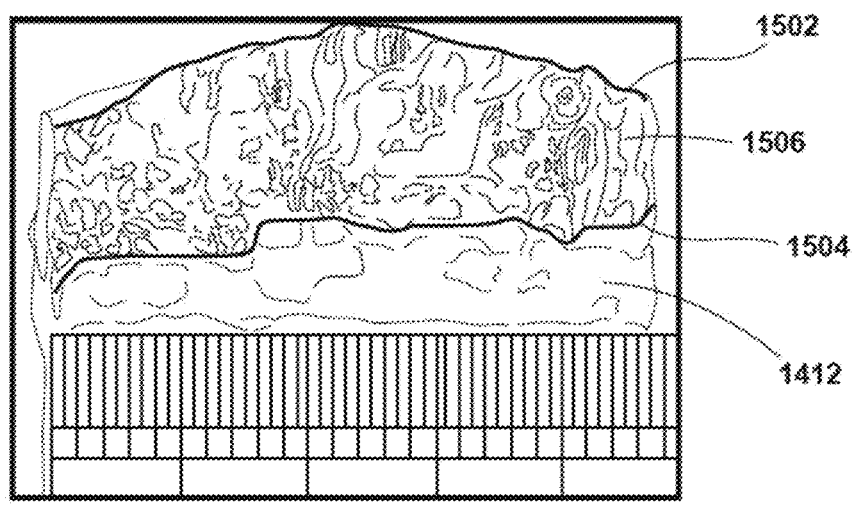
FIG. 15A shows an illustrative side-view of a tissue sample following the exemplary manual cutting task, in accordance with embodiments of the present disclosure.
Figure 15B:
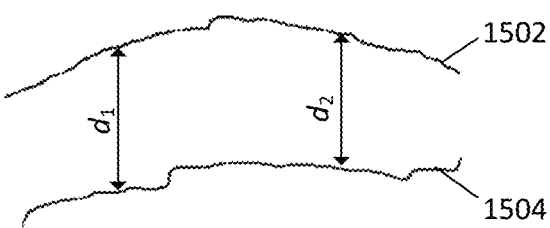
FIG. 15B shows an illustrative comparison of upper and lower edges of the cut portion of the tissue shown in FIG. 15A, in accordance with embodiments of the present disclosure.

FIG. 15A depicts a side view of the tissue sample 1412 of FIG. 14A. A post-processing system (not shown) may extract an estimated top edge 1502 and an estimated bottom edge 1504 of a cut portion 1506 of the tissue sample 1412 for depth error measurement. The estimated top edge 1502 and the estimated bottom edge 1504 may be identified automatically be the subsystem 250 in some embodiments, or may alternatively be identified based on manual input by an operator in other embodiments. FIG. 15B shows an illustrative comparison of the estimated top edge 1502 and bottom edge 1504. Distances (e.g., d1, d2) between corresponding pixels of the top edge 1502 and the bottom edge 1504 may be calculated by the subsystem 250 and may be compared to a desired depth to calculate error. While only one side of the sample 1412 is shown here, it should be understood that the depths of all four sides of the incision may be measured and corresponding error values may be calculated in this way.

While the examples of FIGS. 14A-15B are provided in the context of a manual cutting task, it should be understood that the results of automated cutting tasks and/or automation-assisted cutting tasks may be similarly analyzed to determine error.

FIG. 16 depicts a block diagram of a portion of the RAS system 1100, which includes the supervised autonomous control subsystem 250 and a low-level controller 240. As shown, the subsystem 250 may include the NIR camera 1102, the RGBD camera 1104, a 3D marker position module 1606, a path planner module 1608, a filter 1610, a trajectory generator and planner module 1612, and an inverse kinematics module 1614. In some embodiments, the supervised autonomous control subsystem 250 may be included in a shared control system (e.g., system 230 of FIGS. 3A and 3B), and supervised autonomous control commands 252 that may be generated by the subsystem 250 may be analyzed by such a control system to estimate corresponding error and/or confidence indicators, and may, in combination with separate manual control commands, be used as the basis for generating an allocation function and shared control commands, as will be described.

Real-time video frames from the RGBD camera 1104 and the NIR camera 1102 are collected and processed by the 3D marker position module 1606 to obtain the 3D coordinates of the NIR markers (e.g., markers 1220) in the robot frame. An offsetting technique is applied by the path planner module 1608 to project the NIR marker positions outwards on the point cloud and allow planning an incision path with specified margins around the NIR markers. The offsetting technique executed by the path planner module 1608 uses the 3D vectors formed from the previous and next markers to the current marker, calculates a 5 mm offset on the superposition of the vectors and projects it to the tissue surface by finding the closest point the point cloud. A path planning algorithm executed by the path planner module 1608 calculates a 3D path on the point cloud model of the tissue surface between each two consecutive projected NIR marker positions (e.g., the corners of the desired pattern 1402 in overlay 1400 of FIG. 14A). The path planner module may thereby generate and output reference waypoints. The filter 1610 eliminates the dynamic inter-frame noise of the resulting path so that it is usable in the robot controllers. Real-time position feedback may be sent from the robot to the subsystem 250, to be processed by the trajectory generator and planner module 1612. The reference waypoints output by the path planner 1608 and filtered by the filter 1610 and the real-time robot positions may be received and used by the trajectory generator and planner module 1612 to obtain smooth time-based trajectories using, for example, Reflexxes Motion Libraries in the robot frame. The task-space trajectories of the robot 20 may be converted to the joint-space trajectories by the inverse kinematics module 1614 using, for example, Kinematics and Dynamics Library (KDL) of Open Robot Control Systems (OROCOS).

Low-level closed-loop robot controllers may be implemented so that the robot 20 follows the desired joint space trajectories and hence the 3D path waypoints on the tissue 4. For example, the subsystem 250 may output a supervised autonomous control command 252 to the low level controller 240, which then converts autonomous control command 252 to supervised autonomous control signal 241 and sends the autonomous control signal 241 to the robot 20.

As another example, in connection with both FIGS. 3A and 16, the autonomous control command 252 may instead be sent to a shared control system 230, which may process the autonomous control command 252 and a separate manual control command 212 and apply an allocation function α(t) that defines respective percentages of the manual control command 212 and the supervised autonomous control command 252 that are combined to form a shared control command 232, which is then sent to the low level controller 240, which converts the shared control command 232 to a shared control signal 231, which is sent to the robot 20 to control the robot 20.

Figure 17:
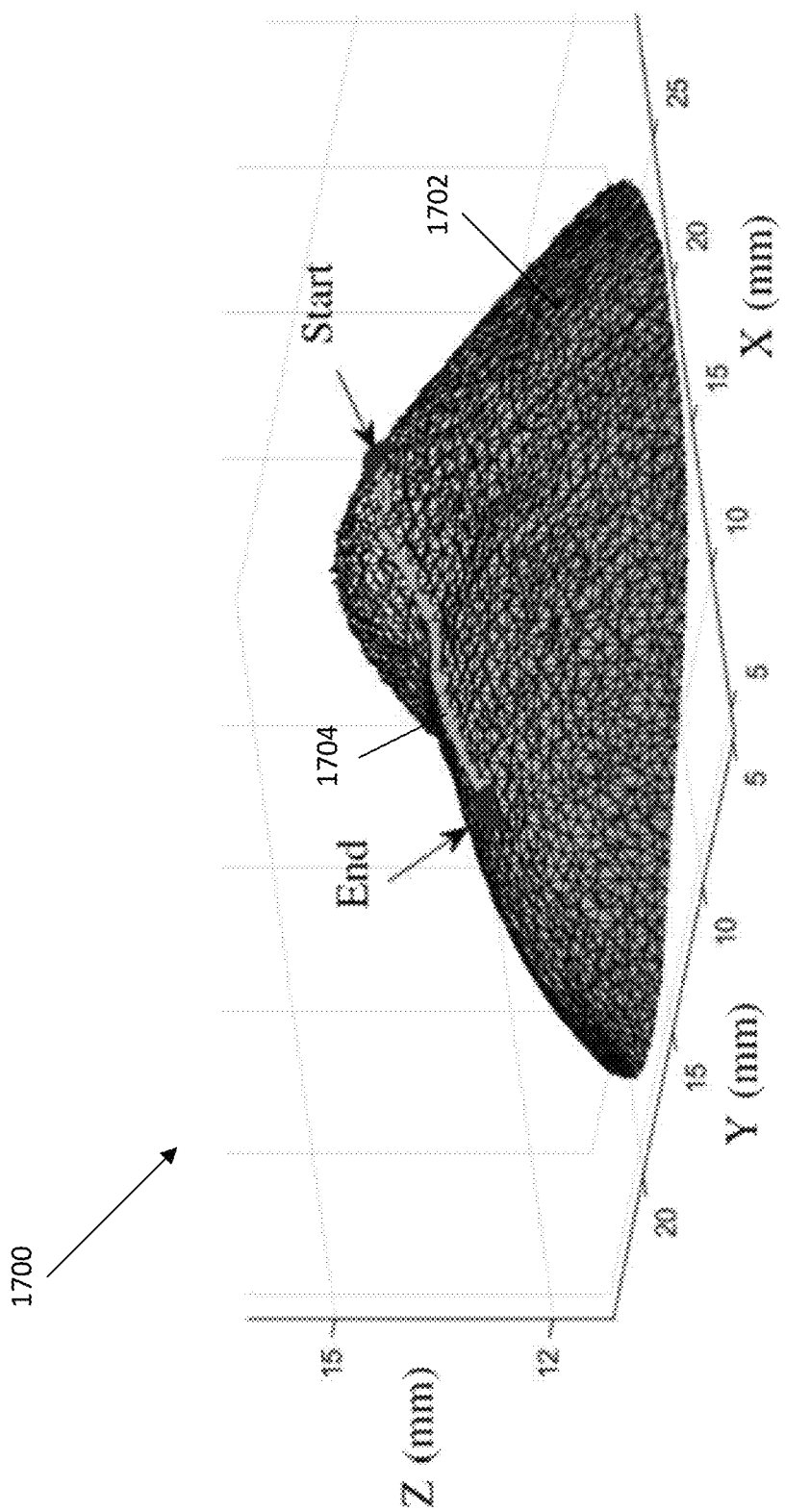
FIG. 17 shows an illustrative graph of a point cloud that may be captured with the RGBD camera of the RAS system of FIG. 11 that includes a path generated for cutting between a start point and an end point on the point cloud, in accordance with embodiments of the present disclosure.

The 3D path planning algorithm implemented by the path planner module 1608 may determine a 3D path between a start point and an end point on a point cloud using, for example, PCL in C++. FIG. 17 shows an illustrative 3D graph 1700 of a point cloud 1702, which may be generated by the RGBD camera 1104. The 3D path planning algorithm may generate a path 1704 that connects a defined start point on the point cloud to a defined end point on the point cloud. First, for example, the point cloud 1702 may be captured by the RGBD camera 1104 and a pass-through filter may be applied to extract the point cloud from a region of interest near the tissue sample 4. Applying the region of interest on the point cloud 1702 may avoid the need for processing the entire raw point cloud and hence may reduce the computation time. Next, a statistical outlier removal (SOR) filter may be applied by the planner module 1608 to reduce the noise in the current point cloud 1702. The SOR filter measures the average distance p and standard deviation a of each point to its k nearest neighbors and rejects neighbors that lie beyond the distance μ+aσ. In addition, a moving least square (MLS) filter may be applied by the path planner module 1608 to create a smooth distribution of the point cloud 1702 by calculating a fitting surface on each point in a sphere radius r through higher order polynomial that fits the original points, and resampling missing points based on the fitting surface. In one embodiment, the parameters may be set to around k=10 neighbors and around a=1 to filter the outliers, and around r=0.01 to create a smoother point cloud. A mesh is then created by the path planner module 1608 using, for example, Delaunay triangulation among the point cloud. The shortest path between a start point and an end point is then computed using, for example, the Dijkstra algorithm, which determines an optimal path (i.e., shortest distance) if it exists.

Figure 19:
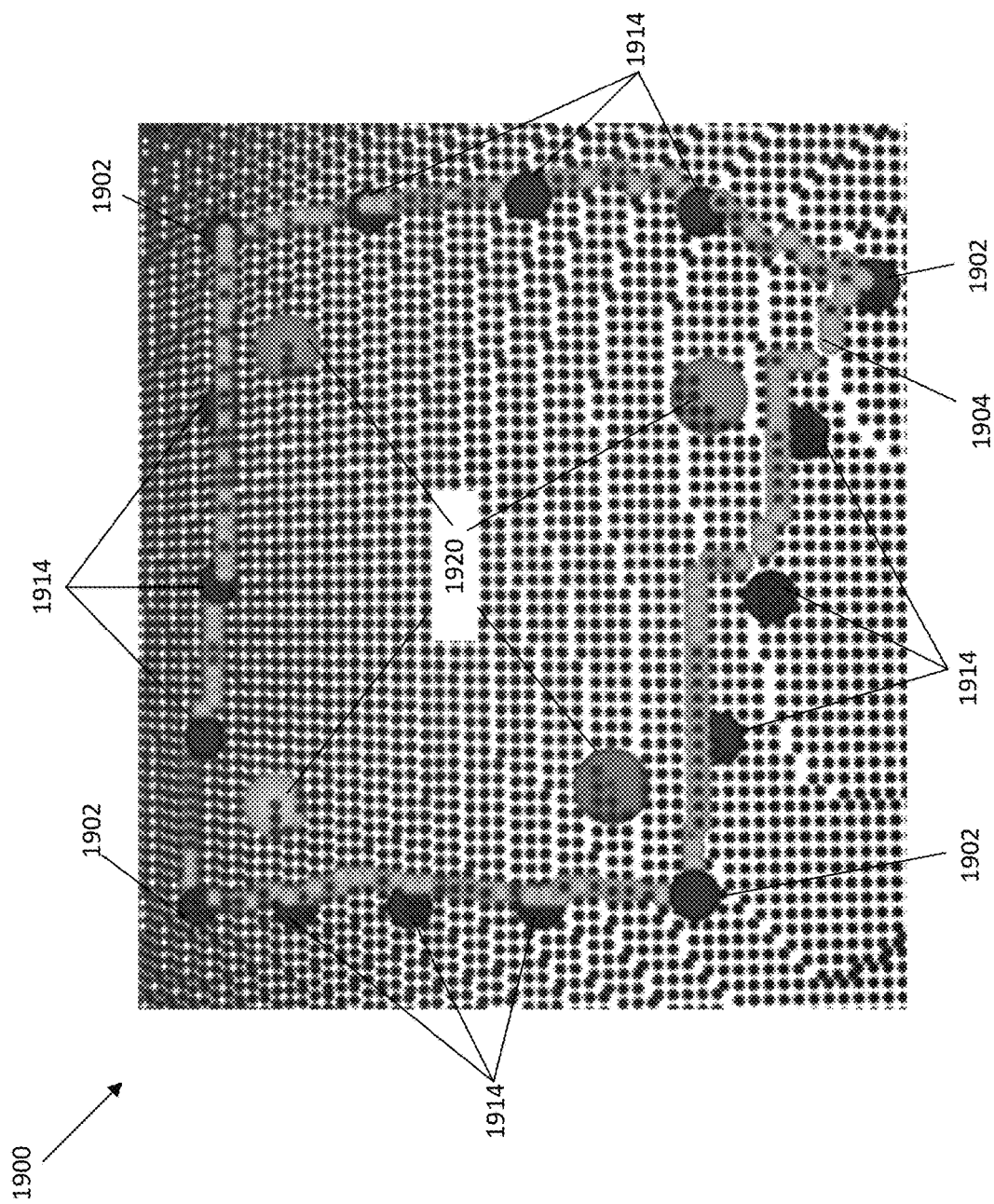
FIG. 19 shows an illustrative example of a series of paths, waypoints, and corresponding NIR markers overlaid on a point cloud, in accordance with embodiments of the present disclosure.

To determine the start and end points of the path 1704, NIR markers (e.g., NIR markers 1220) may be used on the tissue and their positions are projected on the point cloud with a desired offset, as described above. This process is repeated for each two consecutive projected markers as start and end points of each segment of incision (e.g., as illustrated in FIG. 19).

Due to the inherent limitations of various sensing technologies and motions of cameras or objects in the scene, in-frame noise and inter-frame noise may affect the quality of results when using 3D point clouds for real-time measurements and control. In-frame noise may distort the surface of an object of interest, such as, for example, causing a flat surface to appear bumpy. For solid objects, template matching may reduce and/or eliminate the effect of in-frame noise. Other methods for in-frame noise reduction include smoothing and removing outliers for reducing surface or volume noise. Such techniques may be applied (e.g., by the filter 1610 in conjunction with the path planner 1608) to each measurement of point cloud data.

Figure 18A:
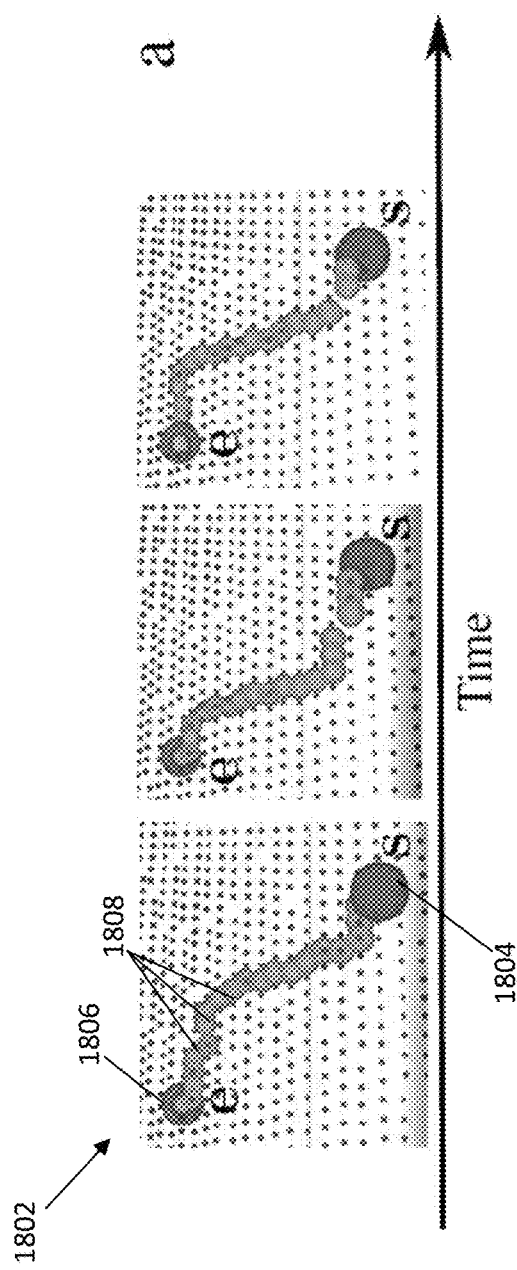
FIG. 18A shows an illustrative sequence of frames that include a raw, unfiltered path that may be generated by a path planner of a supervised autonomous control subsystem, in accordance with embodiments of the present disclosure.

Inter-frame noise, however, occurs in real-time measurements and is related to the slight noisy motion of the point cloud from the previous camera frame to the current one. When used in real-time path planning, inter-frame noise may cause a time-varying number of way-points at the output of path planning algorithm (e.g., the output of the path planner module 1608), and/or a noisy motion of these points between the frames. Inter frame noise may affect autonomous control when performing delicate and precise tasks such as tumor resection with small margins of error. FIG. 18A shows a sequence of frames 1802 that include raw/unfiltered paths generated over time by the path planner module 1608. Each path includes a start point 1804, an end point 1806, and several waypoints 1808. As shown, the waypoints 1808 may experience noisy motion between frames due to inter-frame noise.

Figure 18B:
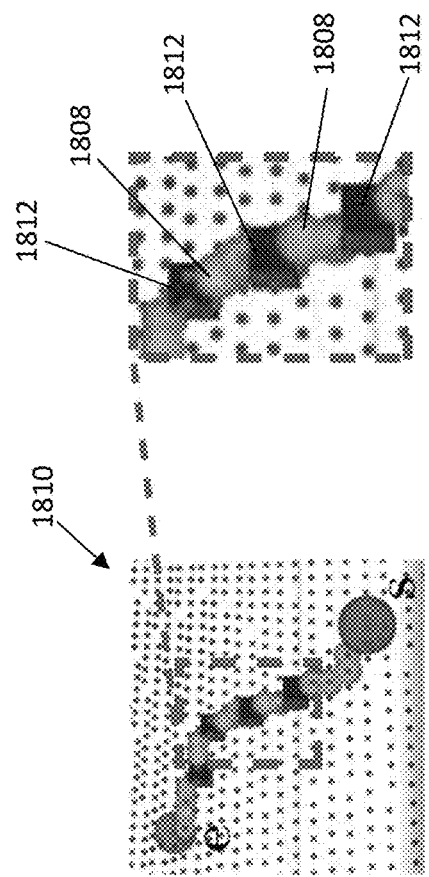
FIG. 18B shows an illustrative frame that includes tracked waypoints of the raw, unfiltered path, in accordance with embodiments of the present disclosure.
Figure 18C:
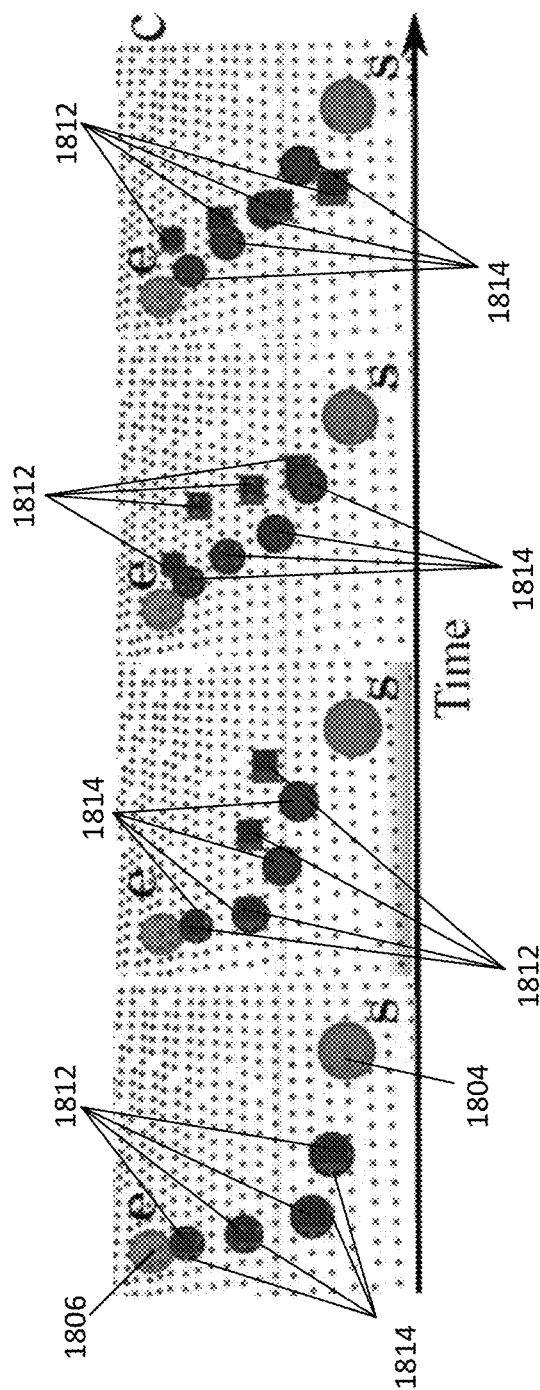
FIG. 18C shows an illustrative sequence of frames that include the tracked waypoints and filtered waypoints that may be output by a filter of the supervised autonomous control system, in accordance with embodiments of the present disclosure.

FIG. 18B shows an individual frame 1810 showing tracked waypoints 1812 that are a subset of the waypoints 1808 that are selected for tracking between frames to counter in-frame noise. For example, a fixed number n (e.g., 4) of way-points 1808 (i.e., the tracked waypoints 1812) on the 3D path may be tracked between the frames. A filtering or estimation algorithm may then be applied to the fixed number of way-points n (e.g., by the filter 1610) over time to obtain a filtered path as additional measurements are acquired. To counter inter-frame noise, a recursive least square (RLS) estimation method may be used to track the waypoints 1812 on the path. For example, for dynamic cases, a Kalman filter (KF), an Extended KF, an Unscented KF, etc., or a particle filter, etc., may be used. FIG. 18C shows, over time, tracked waypoints 1812 and filtered waypoints 1814 generated by the filter 1610 based on the tracked waypoints 1812.

A fixed number of candidate waypoints 1812 and their positions on the noisy path (defined as $w_i$) are first determined, and then a filtering method is applied by the filter 1610. In one embodiment, the candidate waypoints 1812 are determined using a waypoint extraction method, and then the candidate waypoints are filtered using a recursive least squares (RLS) method. Other methods are also contemplated.

For the waypoint extraction method, $s \in \mathcal{R}^3$ and $e \in \mathcal{R}^3$ are the start and end points of the desired path segment on the point cloud, and $P_{se_k} \in \mathcal{R}^3$ is the current calculated path at the time instant k with $n_k$ path points between s and e, and length $l_k$. The elements $n_k$ (i.e. the number of waypoints 1808 in FIG. 18A) and $l_k$ will change dynamically depending on the current reading of the noisy point cloud data and how the path planning algorithm detects the trajectory at that time instant. The path will include at least $n_{min} > 0$ waypoints (i.e., $n_k \geq n_{min}$, $\forall k \geq 0$). A fixed number of waypoints $w_i \in \mathcal{R}^3$, i∈ $\{1, \ldots, n\}$ (e.g., which may interchangeably refer to the tracked waypoints 1812 of FIGS. 18B and 18C) are selected from this path, and then tracked and filtered as more measurements of the noisy path $P_{se_k}$ are collected. If $n \leq n_{min}$ waypoints are selected for tracking, a fixed number of points are always used in the filtering algorithm to track their dynamics over time, and $n_{min}$ may be determined dynamically over time based on the resolution and density of the point cloud obtained from the 3D sensor/camera in the neighborhood of s and e. In order to find the position of the tracked waypoints $_i$, they are equally distributed along $P_{se_k}$ using the total length $l_k$ (i.e., breaking $l_k$ into n+1 equal sections). The positions of $w_i$ are determined as a point on the current path $P_{se_k}$ that is the closest point to the location $$\frac{i}{n+1} l_k$$

from the start points (e.g., at $\frac{1}{4}l_k$, $\frac{2}{4}l_k$, and $\frac{3}{4}l_k$ for n=3).

The RLS method, which may be applied after the waypoint extraction method, filters the positions of the waypoints $w_i$ to produce filtered waypoints (i.e. the filtered waypoints 1814 in FIG. 18C) using the noisy measurements of the path. With unknown but constant waypoint positions on the tissue, the augmented vector of $w_i$ is $w \in \mathcal{R}^{3n \times 1}$ and the corresponding obtained measurements are:

$$y_k = H_k w + v_k$$

where $H_k \in \mathcal{R}^{3n \times 3n}$ is the output/measurement matrix, $y_k \in \mathcal{R}^{3n \times 1}$ is the current measurement of W and is obtained by augmenting the positions of $w_i$ detailed above, and $v_k \in \mathcal{R}^{3n \times 1}$ is the measurement noise. The augmented vector of the estimation of $w_i$ at time step k is $\tilde{w}_k \in \mathcal{R}^{3n \times 1}$, and the estimation error is:

$$\epsilon_k = w - \tilde{w}_k.$$

The cost function is the aggregated variance of the estimation errors:

$$J_k = E(\epsilon_k^T \epsilon_k) \qquad (4)$$

The following sequential algorithm minimizes the cost function (i.e., Equation 4) in order to obtain an accurate estimation of w:

$$K_k = P_{k-1} H_k^T (H_k P_{k-1} H_k^T + R_k)^{-1},$$

$$P_k = (I - K_k H_k) P_{k-1},$$

$$\tilde{w}_k = \tilde{w}_{k-1} + K_k(y_k - H_k \tilde{w}_{k-1}).$$

Here, $K_k \in \mathcal{R}^{3n \times 3n}$ is the estimation gain matrix, $H_k \in \mathcal{R}^{3n \times 3n} = E(v_k^T v_k)$ is measurement noise covariance matrix, and $P_k \in \mathcal{R}^{3n \times 3n}$ is estimation-error covariance matrix, and I is the identity matrix. After each measurement of $y_k$, the estimation $\tilde{w}_k$ (e.g., which may correspond to the filtered waypoints 1814) is updated, which over time, converges to constant values. If the positions of the start and end points s and e suffer from the point cloud noise similar to the waypoints on the path, with a simple change of index l to include $i \in \{1, \ldots n+1\}$, these points are tracked and filtered as well.

FIG. 19 shows a snapshot example of an autonomous incision path 1900 with an offset around four NIR markers 1920 (e.g., NIR markers 1220 of FIG. 12A) and n=3 filtered waypoints 1914 (e.g., filtered waypoints 1814 of FIG. 18C) between the start/end points 1902 of each path. For comparison, the noisy (i.e., unfiltered) path 1904 is also shown. In one example embodiment, the initial filter parameter values may be $P_0 = 100 I_{3n}$ (i.e., $w_i$ unknown a priori), $H_0 = I_{3n}$ (i.e., all x,y,z readings of $w_i$ are obtained from the point cloud), $R_0 = 2 I_{3n}$ (adjusted accordingly), and $K_0 = 0.01 I_{3n}$, where $I_{3n}$ is the identity matrix. The measurements matrix $H_k$ may be constant with a fixed level of noise during the measurements for $R_k$. Therefore, $\forall k$ with $H_k = H_0$ and $R_k = R_0$. However, the filter may continue updating $K_k$, $P_k$, and $\tilde{w}_k$ until a steady-state level is achieved.

In order to control the depth of incisions, the planned incision path may be shifted by about 5 mm below the tissue surface along the z axis of the robot tool direction which is perpendicular to the tissue, and hence the robot 20 may perform the cut with the desired depth according to Equation 5:

$$\begin{bmatrix} x \\ y \\ z \\ 1 \end{bmatrix} = H_r^t H_t^c \left( \begin{bmatrix} x \\ y \\ z \\ 1 \end{bmatrix}_c + \begin{bmatrix} 0 \\ 0 \\ 0.005 \\ 1 \end{bmatrix} \right)_t \qquad (5)$$

where $H_r^T$ is the homogenous transformation for converting the electrocautery tool 24 to the robot base coordinates, $H_t^c$ is the transformation for converting the camera to robot coordinates, and $[x\ y\ z\ 1]_c$ is formed by the coordinates of $\tilde{w}_k$.

The tissue (e.g., tissue sample 4) in contact with the electrode immediately vaporizes when the power setting on the electrocautery tool 24 matches the clinical setting and proper robot velocities are chosen for following the path. The contact forces with the tissue during the electrocautery are negligible and no disturbances interfere with the robot controllers.

FIGS. 20-26 depict various additional features of a RAS system (e.g., the RAS system 1100 of FIG. 11), in accordance with another embodiment of the present disclosure.

Different confidence indicator identification methods for supervised autonomous control subsystem 250 may be used. More specifically, the accuracies of the NIR marker position estimation and path planning algorithms may be evaluated via an identification pattern that is positioned at different configurations with respect to the camera system and is also subjected to different noises. These criteria may affect the accuracy of the incision paths performed by the autonomous robot controller.

Figure 20:
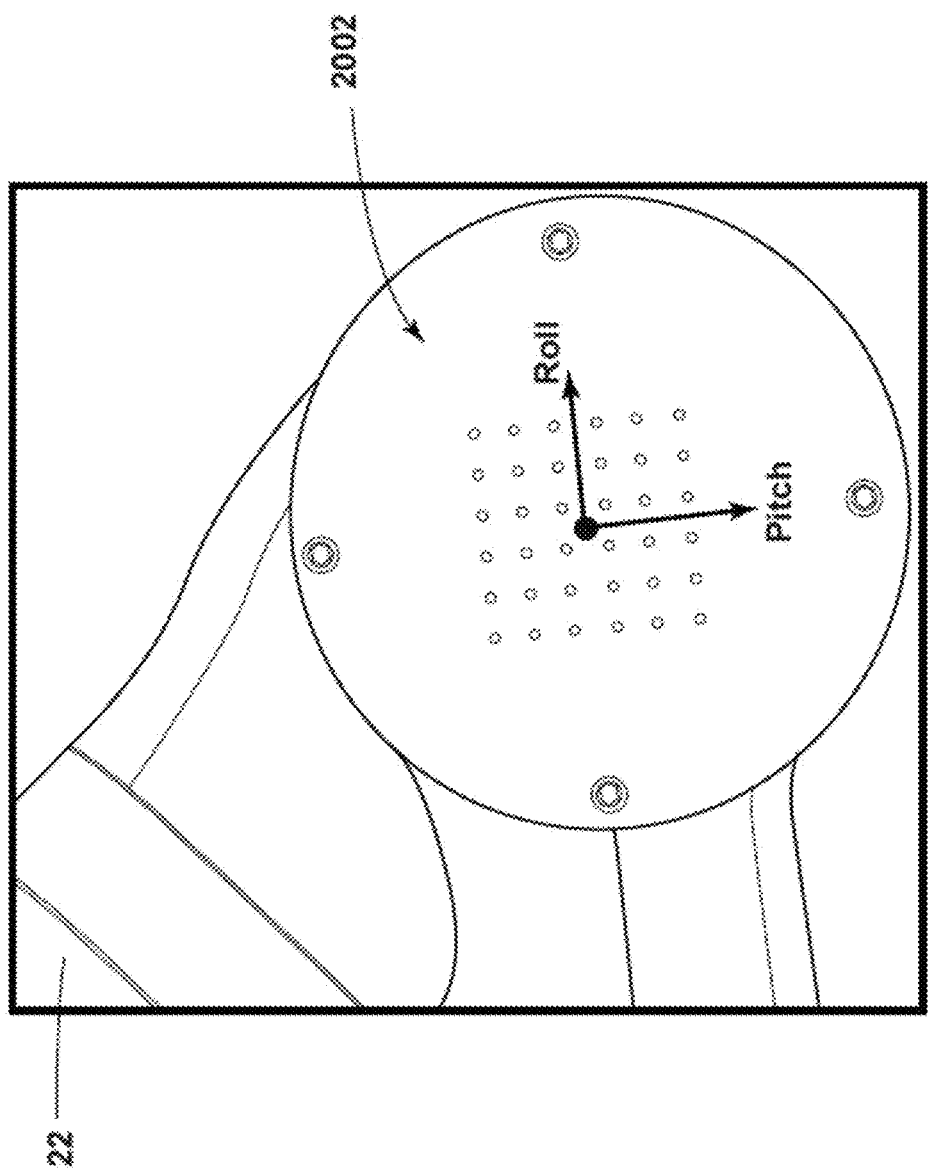
FIG. 20 shows an illustrative identification pattern that may be used to assess accuracy of a 3D NIR marker projection method that may be performed by the RAS system, in accordance with an embodiment.

FIG. 20 depicts an identification pattern 2002 mounted on arm 22 of the robot 20. In order to assess the accuracy of the 3D NIR marker projection method described above, a pattern with a known geometry may be used, such as, for example, the identification pattern 2002. This pattern 2002 shown in the present example includes 36 marker wells which are equally spaced at 1-cm horizontal and vertical intervals to form a symmetric grid about the center of the identification pattern. This known geometry is used as the ground truth or baseline to evaluate how the accuracy of the camera system (e.g., cameras 1102 and 1104 of FIGS. 11 and 16) for 3D marker position projection varies as different parameters such as distance to the camera, angular positions, etc., are varied.

Figure 21:
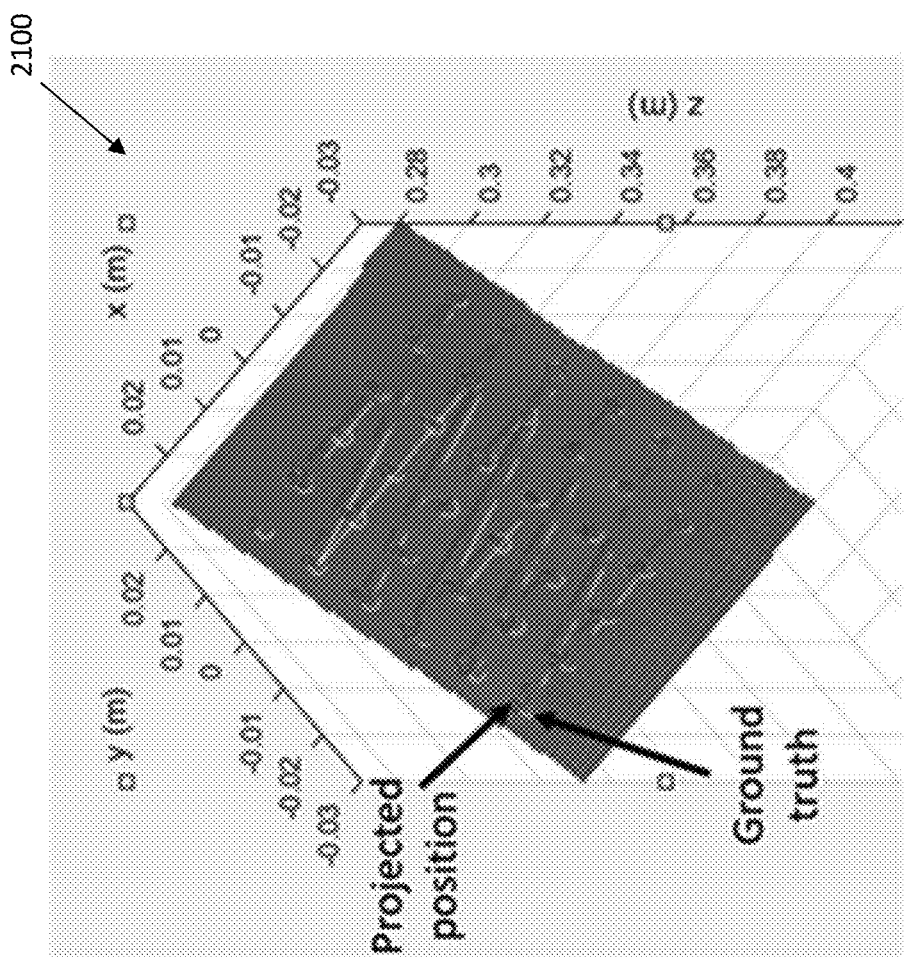
FIG. 21 shows an illustrative graph that provides an example of evaluating marker projection errors, in accordance with embodiments of the present disclosure.

FIG. 21 shows a graph 2100, which provides an example of evaluating marker projection errors at a 31 cm distance with a −40 degree roll angle and a 0 degree pitch angle. Examples of baseline data and projected marker positions via the camera system are shown. The projection error is calculated using the average 3D distances between the baseline and the corresponding projections.

Figure 22:
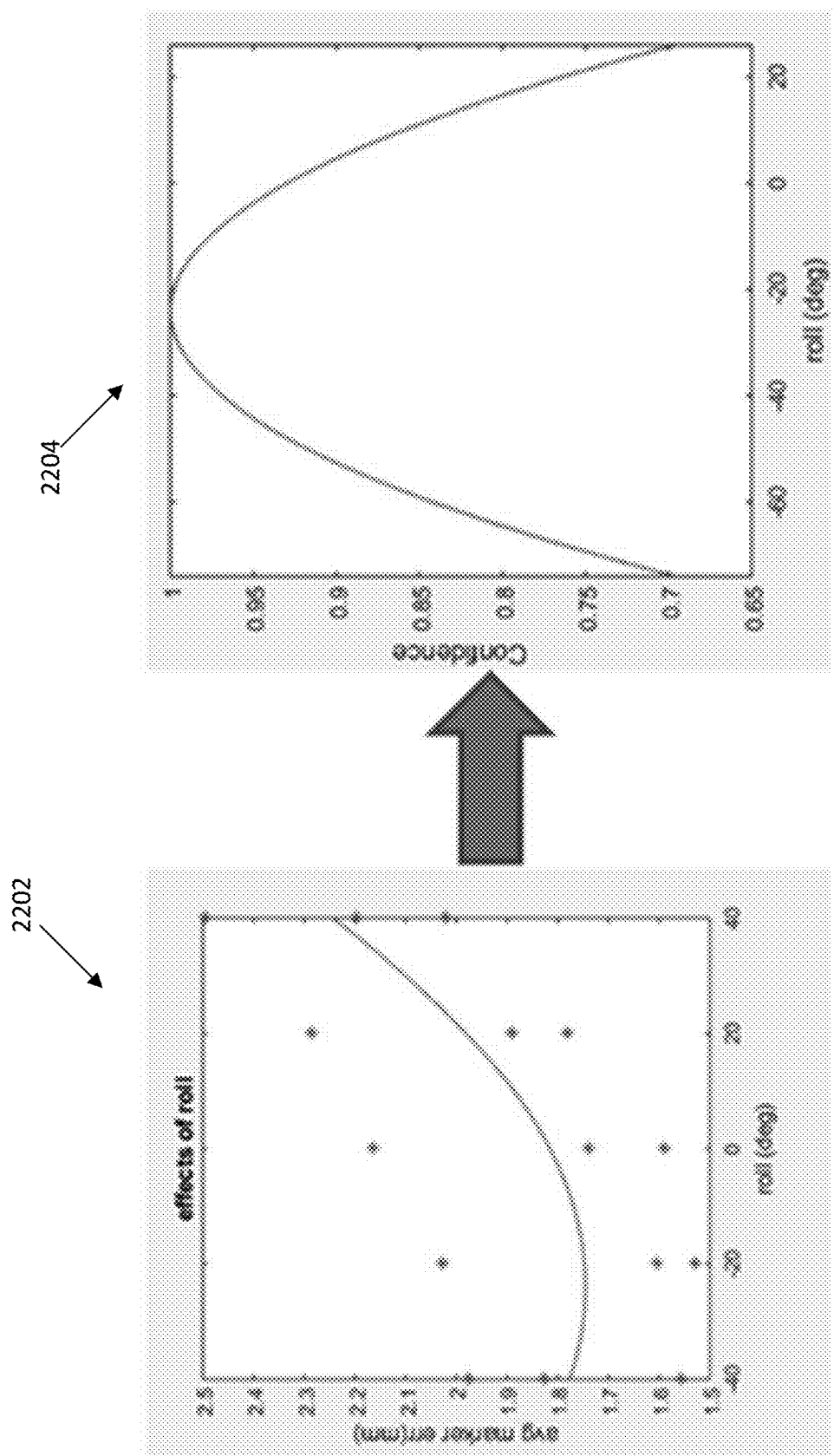
FIG. 22 shows an illustrative graph that provides an example of the effects of changes in roll angle on marker projection error and an illustrative graph of the corresponding confidence indicator (model), in accordance with embodiments of the present disclosure.

FIG. 22 depicts a graph 2202 illustrating the effects of changes in roll angle on marker projection error, and a graph 2204 illustrating the corresponding identified confidence indicator.

Figure 23:
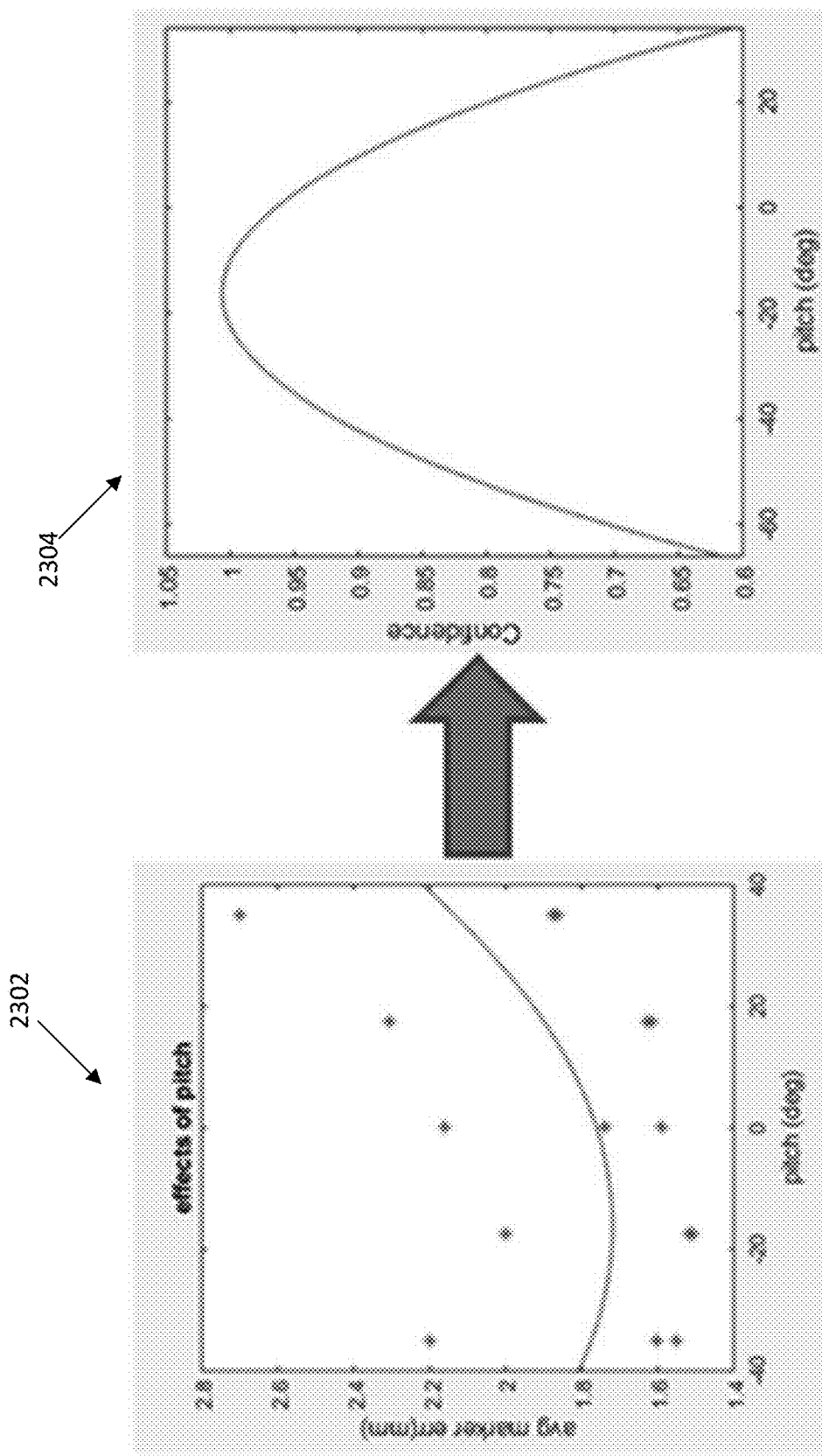
FIG. 23 shows an illustrative graph that provides an example of the effects of changes in pitch angle on marker projection error and an illustrative graph of the corresponding confidence indicator (model), in accordance with embodiments of the present disclosure.

FIG. 23 depicts a graph 2302 illustrating the effects of changes in pitch angle on marker projection error, and a graph 2304 illustrating the corresponding identified confidence indicator.

Figure 24:
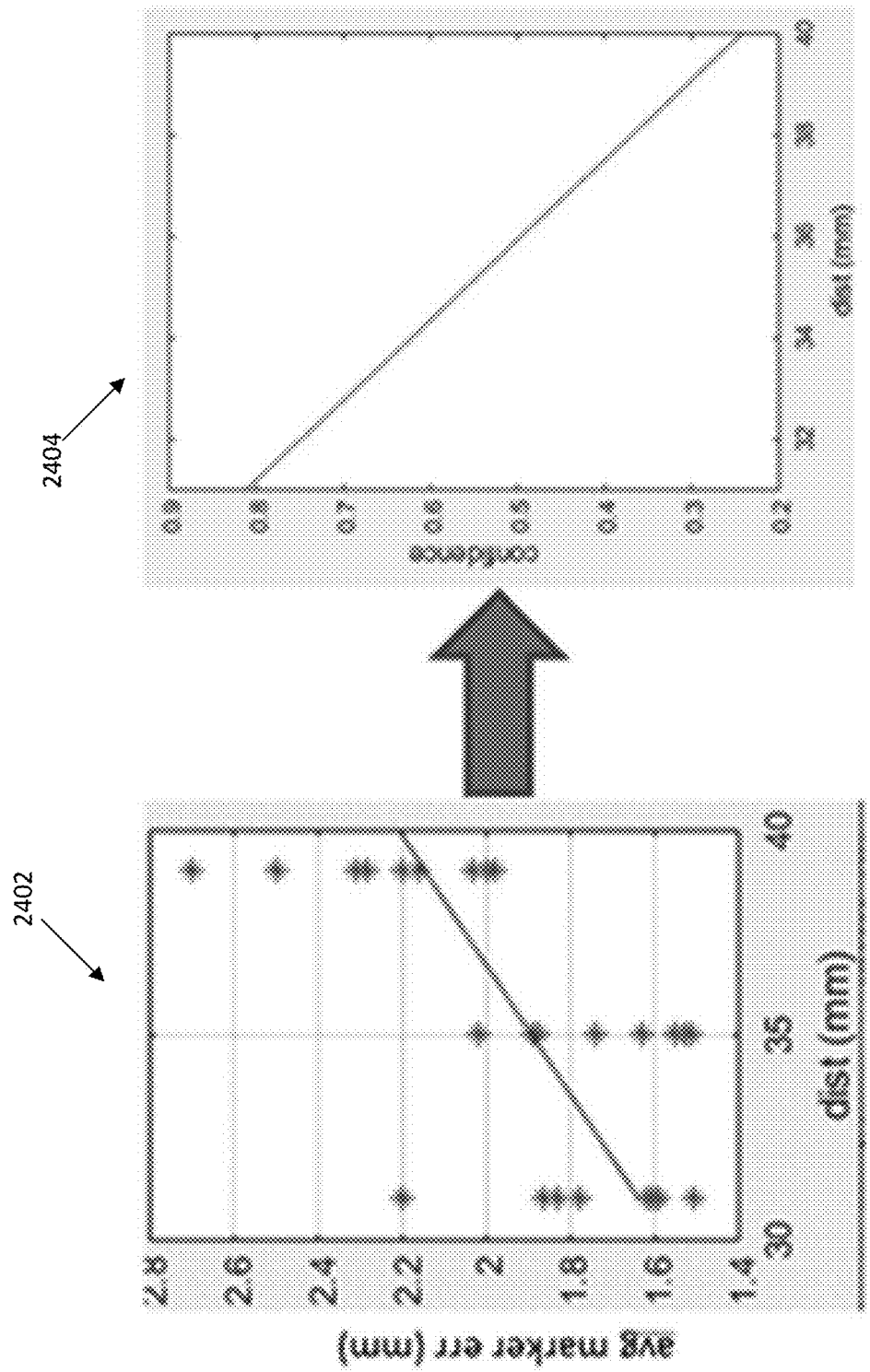
FIG. 24 shows an illustrative graph that provides an example of the effects of changes in distance on marker projection error and an illustrative graph of the corresponding confidence indicator (model), in accordance with embodiments of the present disclosure.

FIG. 24 depicts a graph 2402 illustrating the effects of changes in distance on marker projection error, and a graph 2404 illustrating the corresponding identified confidence indicator.

The results of evaluating marker projection errors for a combination of three different pattern distances from the camera system (i.e. 31 cm, 35 cm, 39 cm), five different angular positions for roll (i.e. at −40 degrees, −20 degrees, 0 degrees, 20 degrees, 40 degrees), and five different angular positions for pitch (i.e. at −35 degrees, −17.5 degrees, 0 degrees, 17.5 degrees, 35 degrees) of the identification pattern are summarized in FIGS. 22-24. In graphs 2202, 2302, and 2402, raw data is shown with star makers and the fitted model with a solid curve. As it can be seen in FIGS. 20 and 21, for both of the roll and pitch angles, the error models have a minimum error at a certain angular position (e.g. −24 degrees for roll and −16 degrees for pitch).

As the value of angular positions degrease or increase from these minimum error locations, the marker projection error increases. In general, depending on the camera system configuration, the angles at which the minimum error occurs can take the generic form of rmin for roll and Pmin for pitch.

The confidence indicators are calculated by inverting and shifting the curve fitted to the error models so that lower errors are associated with higher confidence values. As a representative example for FIG. 22, the error model for roll angle is err=$0.0001r^2+0.0058$ r+1.815 (with r being the roll angle) and the corresponding confidence indicators is $C_{A1}$=2.745−err. Similarly, for FIG. 21, the error model for pitch angle is err=$0.0002p^2+0.0051$ p+1.761 (with p being the pitch angle) and the corresponding confidence indicators is $C_{A2}$=2.725−err.

When considering the effect of distance on the marker projection error, as seen in FIG. 22, the error increases with distance. For example, the error model identified for data shown in FIG. 22 is err=0.00634 d−0.3296, where d is the distance of the pattern from the camera system. The corresponding identified model, by inverting and shifting the error models for distance error, is $C_{A3}$=2.45−err. Additionally, a scaling method may be implemented to normalize the confidence values between 0 and 1.

Figure 25A:
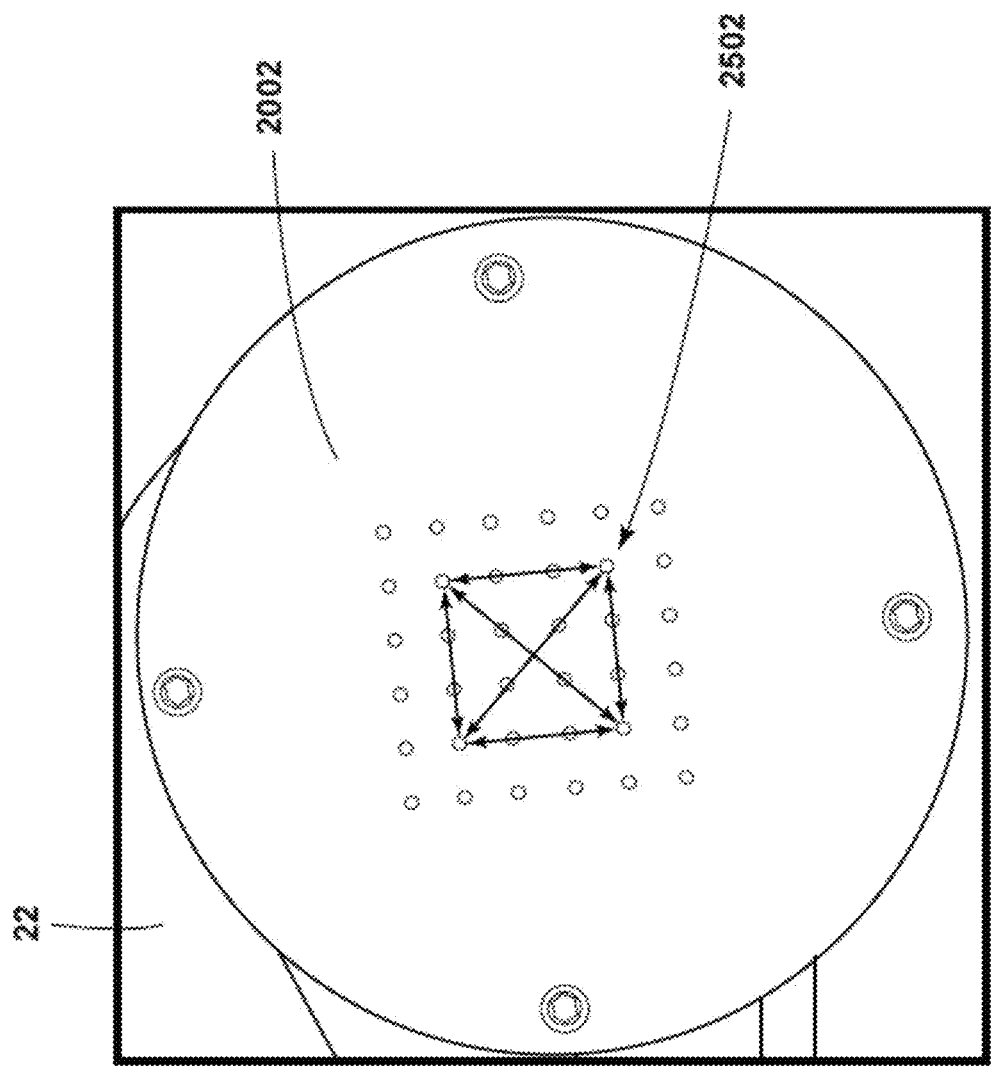
FIG. 25A shows an illustrative desired path planning pattern overlaid on an identification pattern, in accordance with embodiments of the present disclosure.

The identification pattern 2002 can also be used for testing the accuracy of the path planning algorithm when the 3D point cloud is locally subjected to noise resulting in low density data. Clinical sources of noise include external or additional light sources used for illuminating the surgical scene for the surgeon. These light sources may cause local or global reflections and point cloud density degradations in real-time data coming from the camera system. FIG. 25A depicts an illustrative desired path planning pattern 2502 overlaid on the identification pattern 2002 of FIG. 20. To determine the magnitude of the error introduced by light sources, a symmetric set of 12 paths on the identification pattern between 4 different markers is first determined (i.e., the desired path planning pattern 2502). In the present example, a white light source is used to project random external noises on the pattern to disturb the 3D point cloud obtained from the camera system. Data are collected at different angles and distances similar to the pattern configurations described for marker projection error.

Figure 25B:
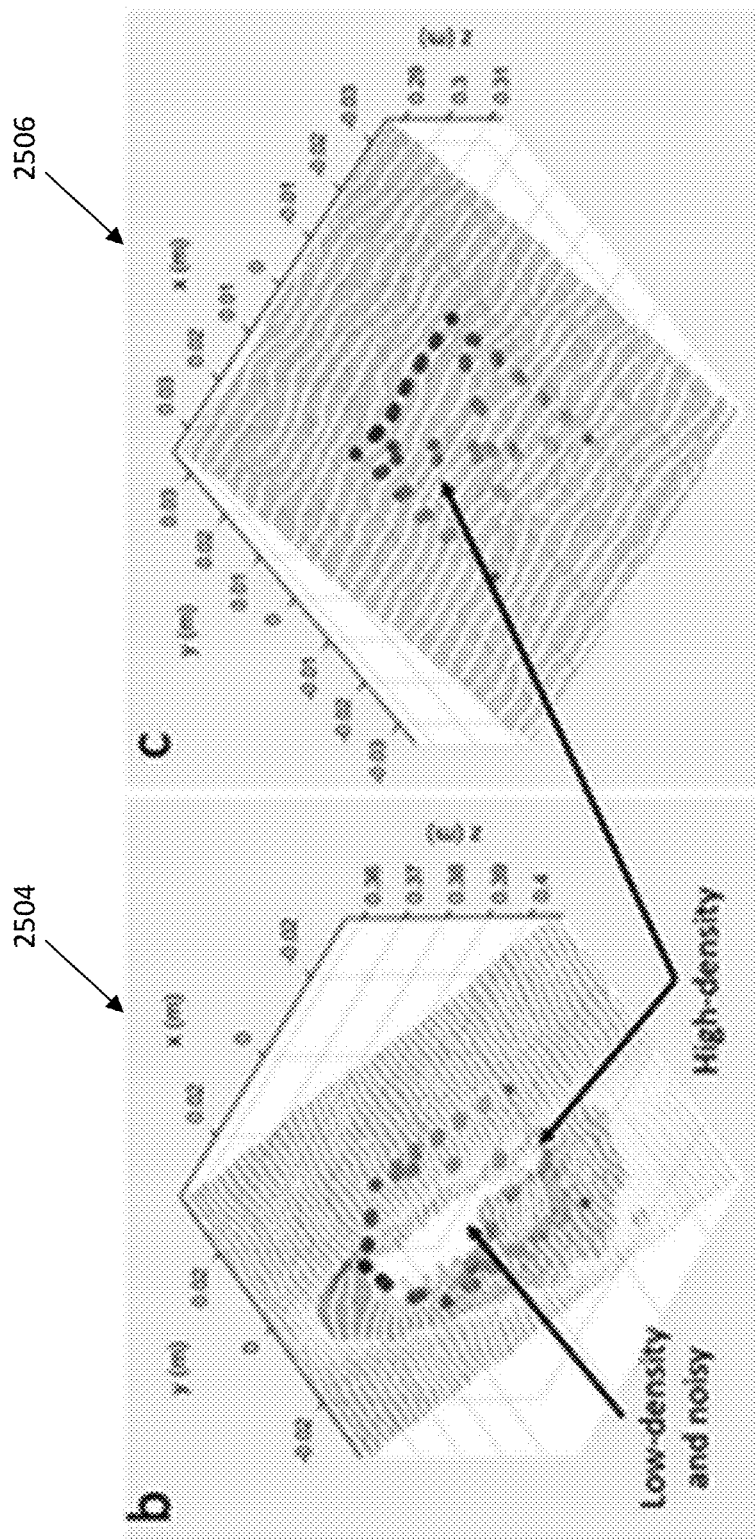
FIG. 25B shows an illustrative 3D graph demonstrating effects of local noise on point cloud density and path planning accuracy, and an illustrative 3D graph illustrating path planning under no external noise, in accordance with embodiments of the present disclosure.

FIG. 25B shows a 3D graph 2504 that illustrates effects of local noise on the point cloud density and path planning accuracy, and a 3D graph 2506 that illustrates path planning under no external noise. As shown in graph 2504, the path planner determines a less than optimal path between the markers within the low-density point cloud regions in the presence of local noise. As shown in graph 2506, the path planner may determine a more accurate path when noise is minimally present on the identification pattern point cloud.

Figure 26:
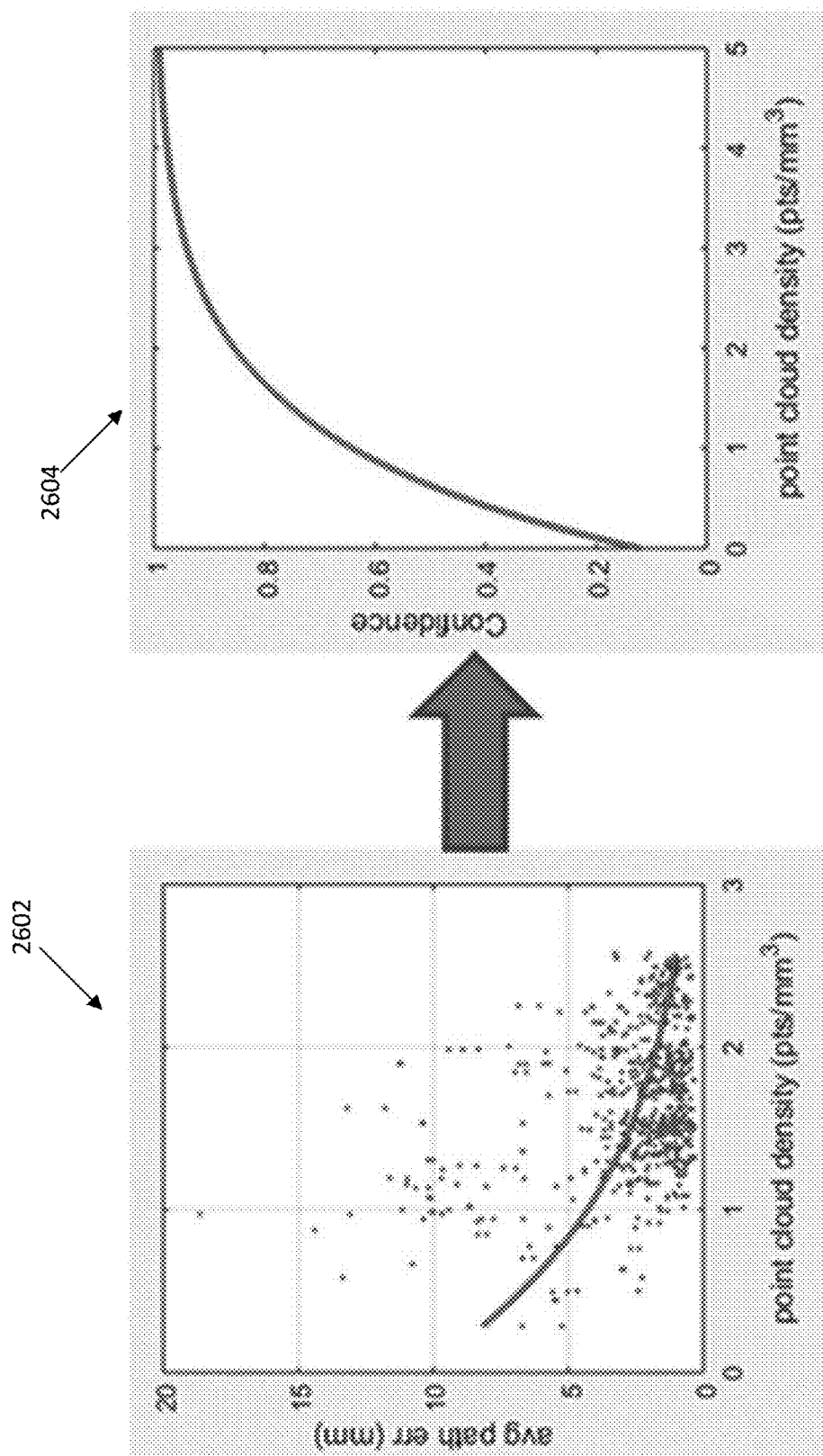
FIG. 26 shows an illustrative graph depicting a path planning error model and corresponding effects of changes in point cloud density on path planning error, and an illustrative graph depicting the corresponding confidence indicator (model), in accordance with embodiments of the present disclosure.

FIG. 26 depicts a graph 2602 illustrating a path planning error model and corresponding effects of changes in point cloud density on path planning error, and a graph 2604 illustrating the corresponding identified confidence indicator.

As shown, the path planning error exponentially decreases as the point cloud density increases because the path planning algorithm relies on the density of the point cloud to produce accurate paths between the markers. In this example, the error model (e.g., density error model) is err=$10.55e^{-0.899s}$ (where s is the point cloud density) and the confidence indicator is obtained by scaling and inverting the error model as $$C_{A4} = \frac{12}{err - 12}.$$

Figure 27:
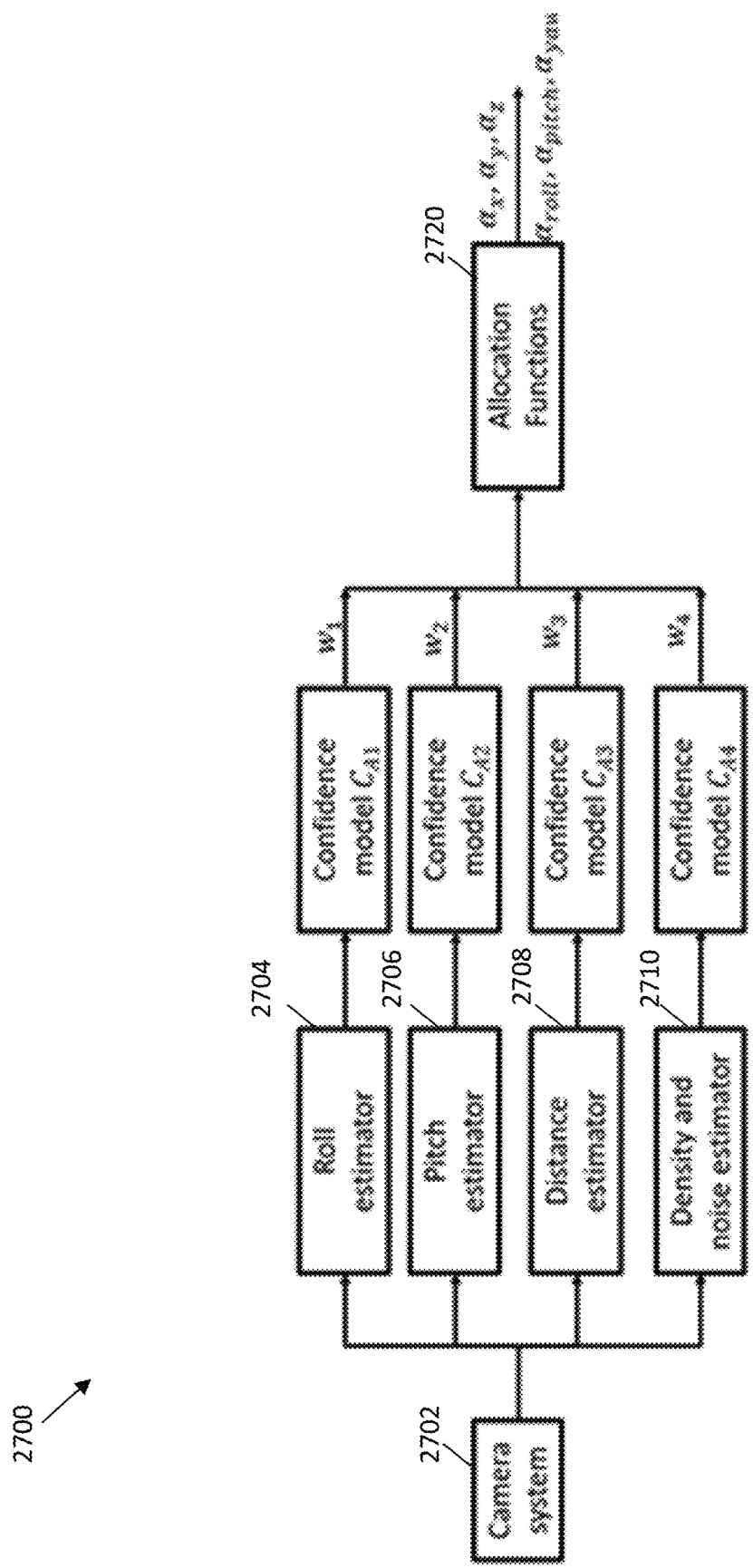
FIG. 27 shows an illustrative system by which confidence indicators may be generated for roll, pitch, distance, and point cloud density, and corresponding allocation functions may be generated based thereon, in accordance with embodiments of the present disclosure.

The confidence indicators identified above can be used during surgery to estimate the autonomous incision error based on the distance and angular positions of the target tissue in the camera system, as well as the quality of the 3D point cloud data from the tissue. FIG. 27 shows an illustrative a block diagram of a multi-criteria confidence-based allocation system for 3D incision tasks, according to an embodiment of the present disclosure.

As shown the system 2700 may include a camera system 2702 (e.g., which may include some or all of the subsystem 250 of FIG. 16), a roll estimator 2704, a pitch estimator 2706, a distance estimator 2708, a density and noise estimator 2710, the confidence indicators (e.g., "confidence models") $C_{A1}$, $C_{A2}$, $C_{A3}$, and $C_{A4}$, and allocation functions 2720. As shown, image data captured by the camera system 2702 may be processed (e.g., in parallel) by the estimators 2704-2710 to generate roll, pitch, yaw, distance, and point cloud density estimates, respectively, along with corresponding error. The confidence indicators $C_{A1}$, $C_{A2}$, $C_{A3}$, and $C_{A4}$, may be used to calculate confidence values based on the errors from the estimators 2704-2710. In some embodiments, the confidence indicators $C_{A1}$, $C_{A2}$, $C_{A3}$, and $C_{A4}$ may, in combination, correspond to either of the confidence indicators 237 and 238 of FIG. 3B, and the allocation functions 2720 may correspond to at least a portion of the adaptive confidence-based autonomy allocation module 239 of FIG. 3B.

In some embodiments, the allocation functions 2720 may correspond to the allocation functions 800 shown in FIG. 9. As described in connection with FIG. 9, the allocation functions may include $a_x$, $a_y$, $a_z$, $a_{rm}$, $a_{pitch}$, $a_{yaw}$ (e.g., corresponding to the movement of the tool 24 of the robot 20 in along x, y, z, axes and roll, pitch, and yaw of the tool 24 of the robot 20) and, in the context of the present example of FIG. 27, x=$w_1 C_{A1} + w_2 C_{A2}$ $w_3 C_A 3 + w_4 C_{A4}$ is the weighted confidence indicator outputs.

Each translational (x-y-z) and rotational (roll-pitch-yaw) motion of robot tool can be considered separately and can be assigned an allocation function of the allocation functions 2720 that uses weighted confidence indicators as input (i.e., the weights $w_1$–$w_4$). The confidence-based allocation functions $\alpha_x$, $\alpha_y$, $\alpha_z$, $\alpha_{roll}$, $\alpha_{pitch}$, $\alpha_{yaw}$ can be selected from the different forms shown and described in connection with FIG. 9 and may be used (e.g., when controlling the robot 20, the arm 22, and/or the tool 24) to generate shared control commands and/or shared control signals (e.g., shared control command 232 and/or shared control signal 231 of FIGS. 3A and 3B) to minimize the incision error. The allocation functions do not necessarily need to be different and in some cases, similar allocation functions can be used for controlling different degrees of freedom of the robot 20 (e.g., and the corresponding arm 22 and/or tool 24).

Figure 28:
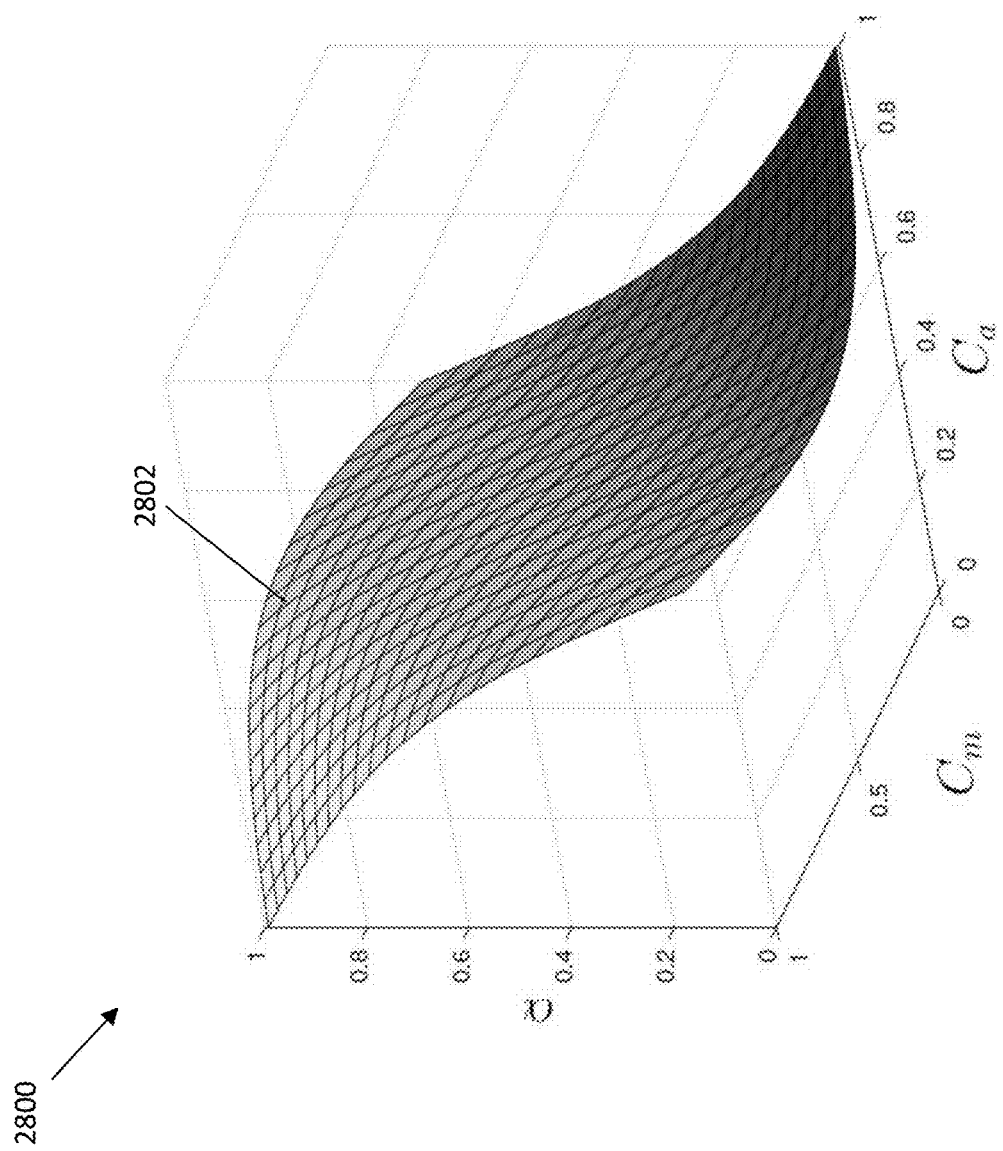
FIG. 28 shows an illustrative graph depicting an allocation function that is calculated based on manual and automatic control confidence indicators, in accordance with embodiments of the present disclosure.

In some embodiments, the allocation functions 2720 may additionally or alternatively include the allocation functions described below in connection with FIG. 28 and Equations 7 and 8.

An example of the design and implementation of the allocation function α when a similar function is used for all the translational (x-y-z) and rotational (roll-pitch-yaw) motion of the robot 20 (e.g., and the corresponding arm 22 and/or tool 24). FIG. 28 shows an illustrative graph 2800 of an allocation function 2802 that is calculated based on both manual control confidence indicators $C_M$, described above, and automatic control confidence indicators $C_A$ (e.g., which may include or be calculated based on $C_{A1}$-$C_{A4}$). The total error for the manual control may be normalized as $\text{err}_M(t) \in [0,1]$ and for the autonomous control as $\text{err}_A(t) \in [0,1]$. The total error resulting from a confidence-based shared control may be defined according to Equation 6:

$$\text{err}(t) = \alpha(t)\text{err}_M(t) + (1-\alpha(t))\text{err}_A(t) \quad (6)$$

which is the weighted compound error from the manual and autonomous control sources. The optimal solution to minimizing err(t) by a choice of α(t) can be found according to Equation 7:

$$\alpha(t) = \begin{cases} 0 & \text{if } \text{err}_M \geq \text{err}_A \\ 1 & \text{if } \text{err}_M < \text{err}_A. \end{cases} \quad (7)$$

However, the allocation function in Equation 7 may cause noisy/jittery allocations of autonomy, which are not necessarily easy for a human to follow due to sudden and frequent changes. An alternate solution is provided in Equation 8:

$$\alpha(t) = \overline{\alpha} - \frac{\overline{\alpha} - \underline{\alpha}}{1 + e^{-s\left(\frac{x-b}{\overline{x}-\underline{x}}\right)}} \quad (8)$$

where $x \in [\underline{x}, \overline{x}]$ is the independent variable with lower/upper bound $\underline{x}/\overline{x}$ for the allocation function. In the allocation function of Equation 8, b is a bias at which $$\alpha(t) = \frac{\overline{\alpha} + \underline{\alpha}}{2},$$

and s is a steepness control parameter. When $s \to \infty$, the allocation function of Equation 8 turns to a step an non-smooth function. In some embodiments, $x = C_A - C_M \in [-1,1]$ may be selected, that is the difference between the overall confidence in the autonomous control $C_a$ and the manual control $C_m$. In some embodiments, the upper and lower bounds may be selected as $\overline{\alpha}=1$, $\underline{\alpha}=0$, b=0 for a symmetric and normalized allocation a function according to the Equations 9-12:

$$\dot{\alpha} = \frac{\partial \alpha}{\partial C_A} \dot{C}_A + \frac{\partial \alpha}{\partial C_M} \dot{C}_M \quad (9)$$

where

-continued $$\frac{\partial \alpha}{\partial C_M} = \frac{s}{2} \frac{e^{-\frac{s}{2}(C_A - C_M)}}{\left(1 + e^{-\frac{s}{2}(C_A - C_M)}\right)^2} \quad (10)$$

and $$\frac{\partial \alpha}{\partial C_A} = -\frac{\partial \alpha}{\partial C_M}, \quad (11)$$

then we obtain $$\dot{\alpha} = \frac{s}{2} \frac{e^{-\frac{s}{2}(C_A - C_M)}}{\left(1 + e^{-\frac{s}{2}(C_A - C_M)}\right)^2} (\dot{C}_A - \dot{C}_M). \quad (12)$$

Since $C_A - C_M \in [-1,1]$, $$e^{-\frac{s}{2}(C_A - C_M)}$$

is bounded in [0, 1] if s>0 is chosen. If $\dot{C}_A$ and $\dot{C}_M$ are Lipschitz continuous (i.e. no sudden failure occurs in either manual or autonomous control modes to cause a discontinuous change in the confidence indicators), $\dot{\alpha}$ is largely affected by s. For example s may be set to 5 or around 5 for both smooth and fast allocation of autonomy between the manual and autonomous robot controllers.

Figure 29:
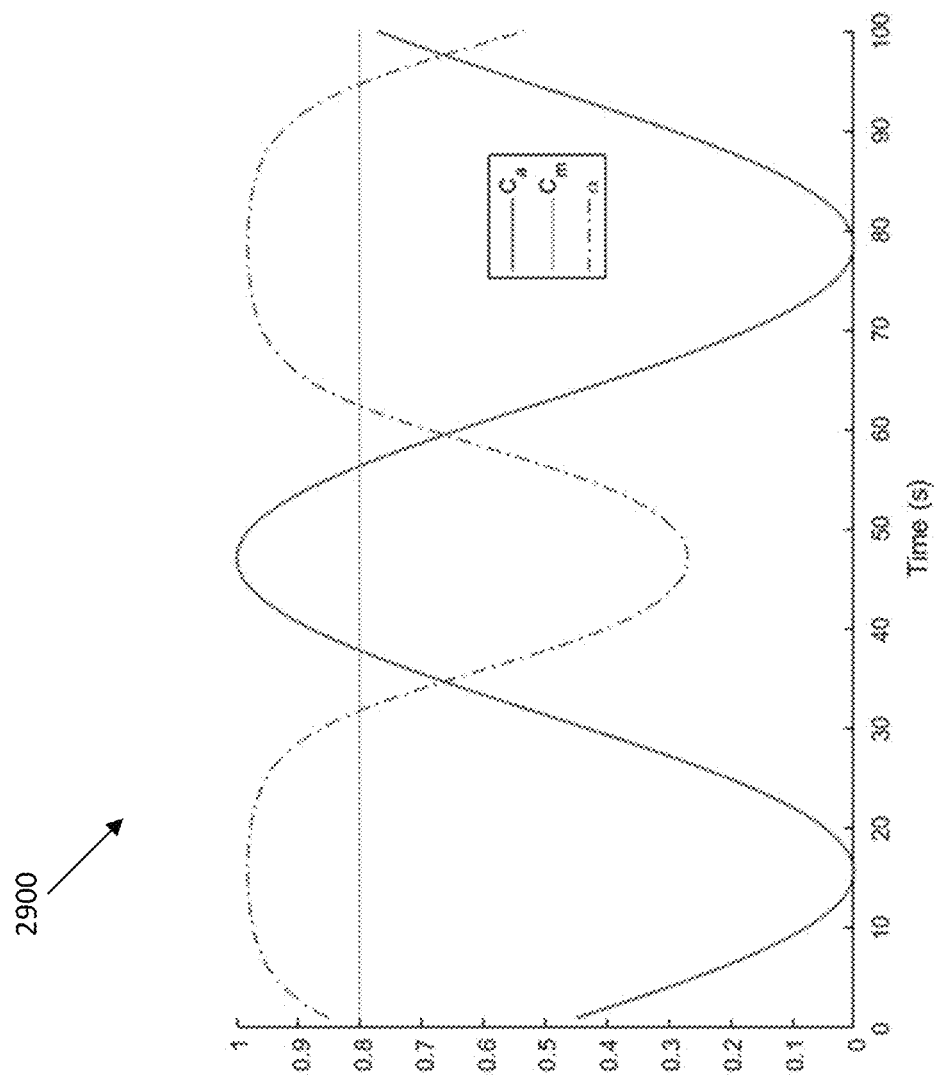
FIG. 29 shows an illustrative graph depicting autonomy allocation for time-varying confidence in autonomous and manual control, where the manually controlling operator has a high level of skill, in accordance with embodiments of the present disclosure.

FIG. 29 shows a graph 2900 illustrating autonomy allocation for time-varying confidence in autonomous control and manual control, where the manually controlling operator has a high level of skill, resulting in little allocation of autonomous control.

Figure 30:
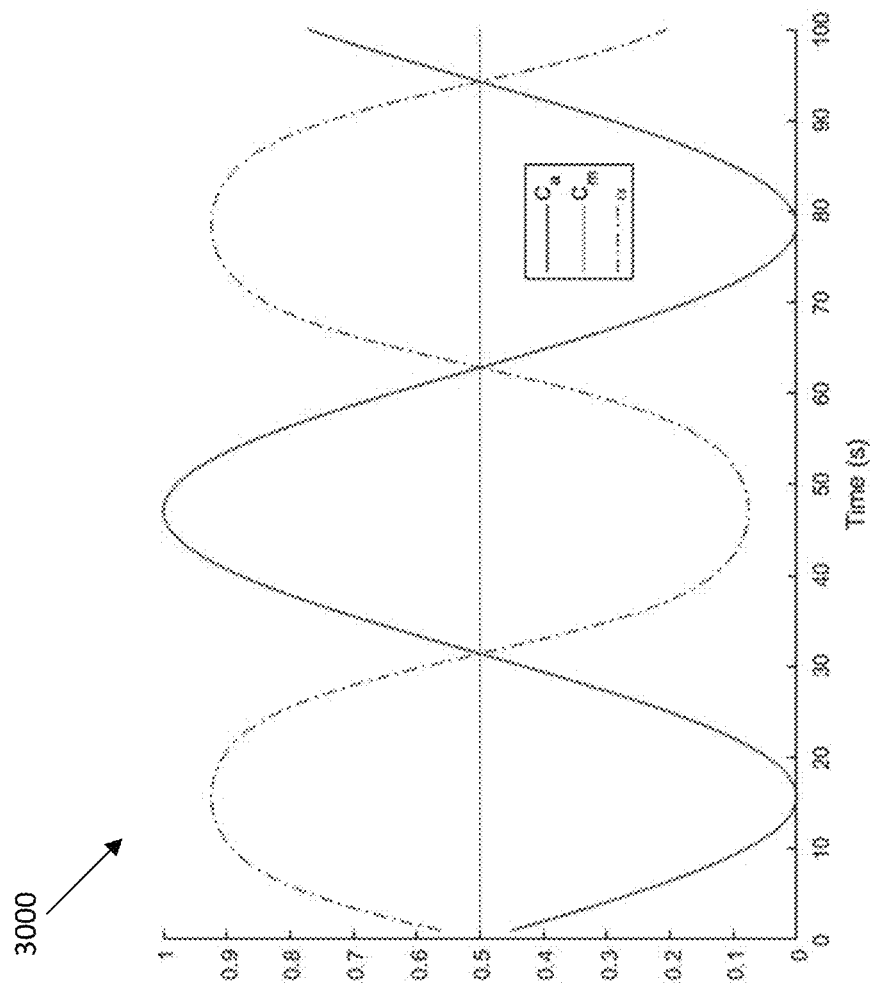
FIG. 30 shows an illustrative graph depicting autonomy allocation for time-varying confidence in autonomous and manual control, where the manually controlling operator has a moderate level of skill, in accordance with embodiments of the present disclosure.

FIG. 30 shows a graph 3000 illustrating autonomy allocation for time-varying confidence in autonomous control and manual control, where the manually controlling operator has a moderate level of skill, resulting in moderate allocation of autonomous control.

Figure 31:
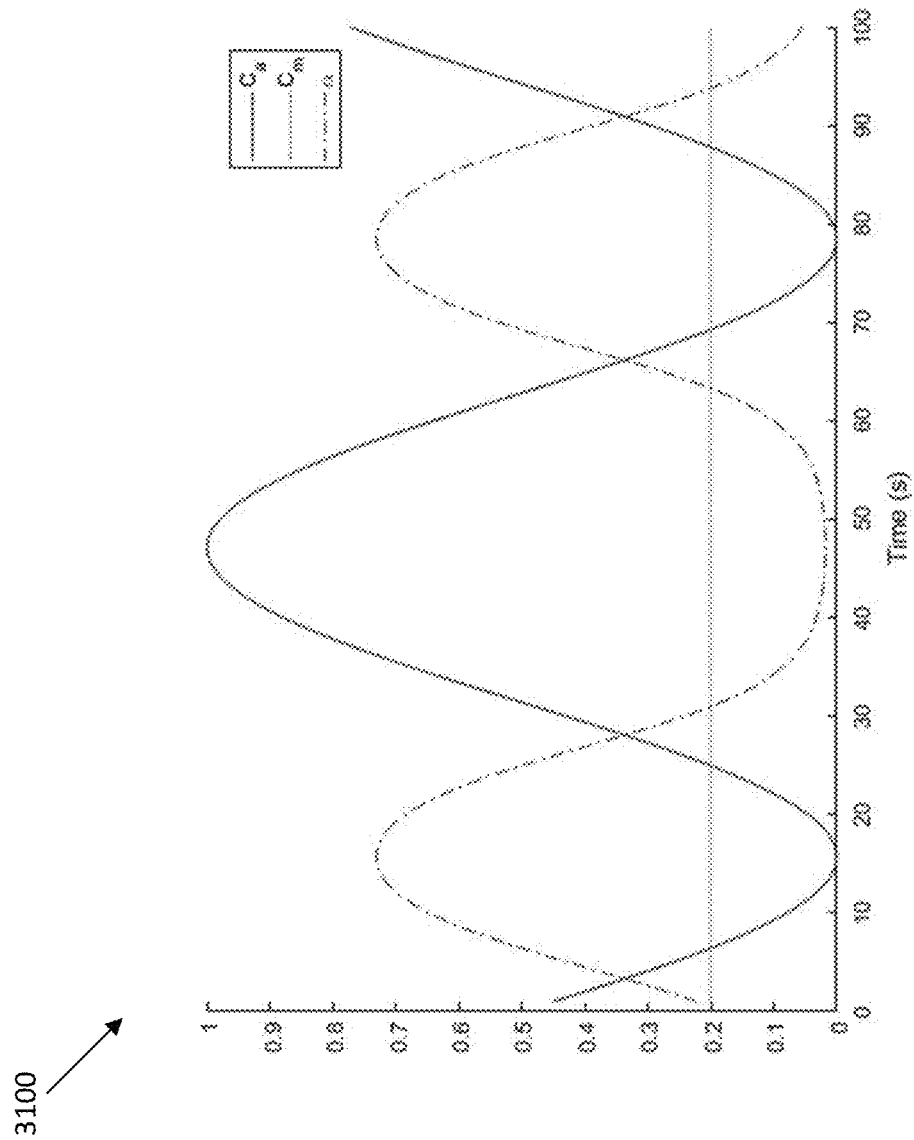
FIG. 31 shows an illustrative graph depicting autonomy allocation for time-varying confidence in autonomous and manual control, where the manually controlling operator has a low level of skill, in accordance with embodiments of the present disclosure.

FIG. 31 shows a graph 3100 illustrating autonomy allocation for time-varying confidence in autonomous control and manual control, where the manually controlling operator has a low level of skill, resulting in high allocation of autonomous control.

Figure 32A:
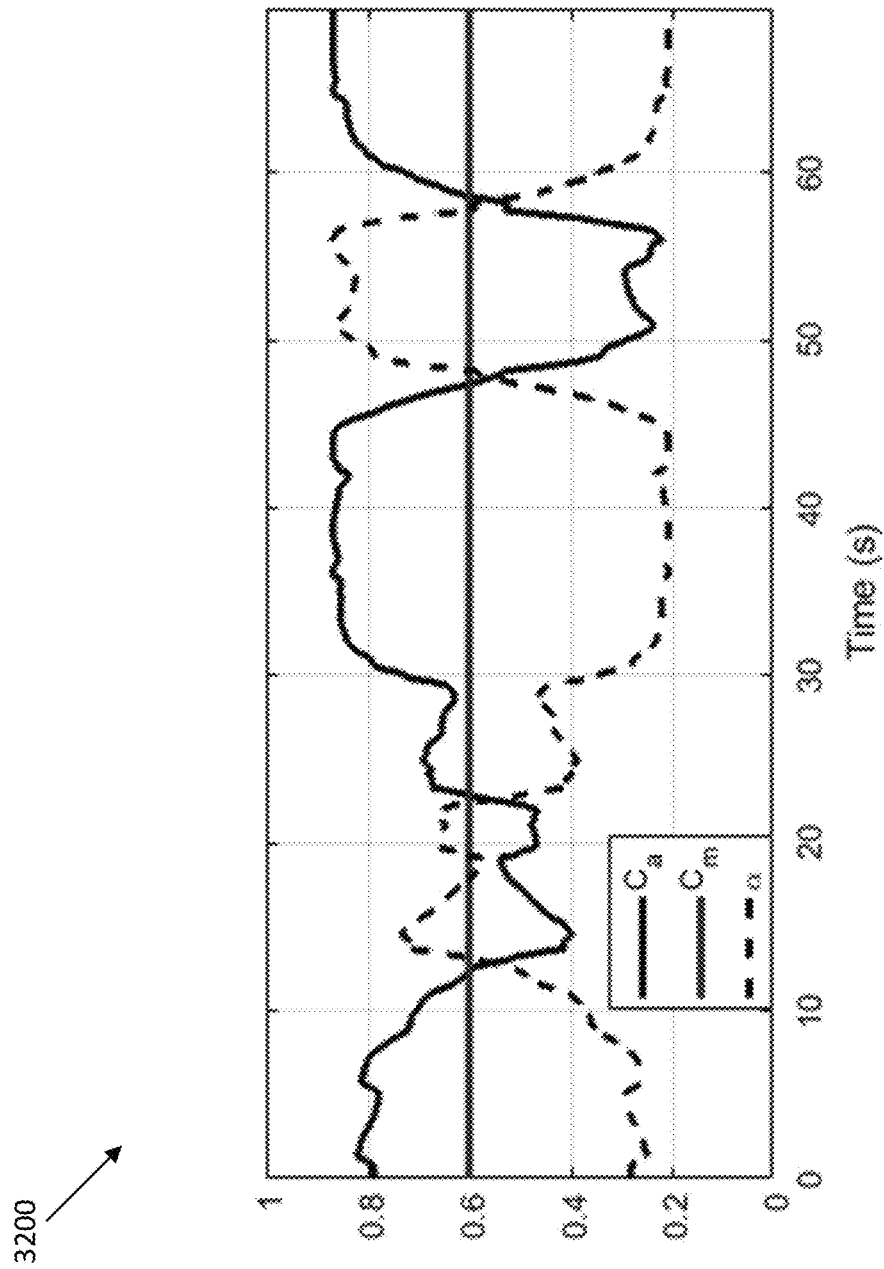
FIG. 32A shows an illustrative graph depicting an allocation function compared to automatic and manual confidence indicators, in accordance with some embodiments of the present disclosure.

FIG. 32A shows an example of autonomy allocation using the RAS system 1100 of FIG. 11. As shown in the illustrative graph 3200, the shared control strategy smoothly produces a smaller α(t) when the autonomous control is superior to manual control and vice versa.

Figure 32B:
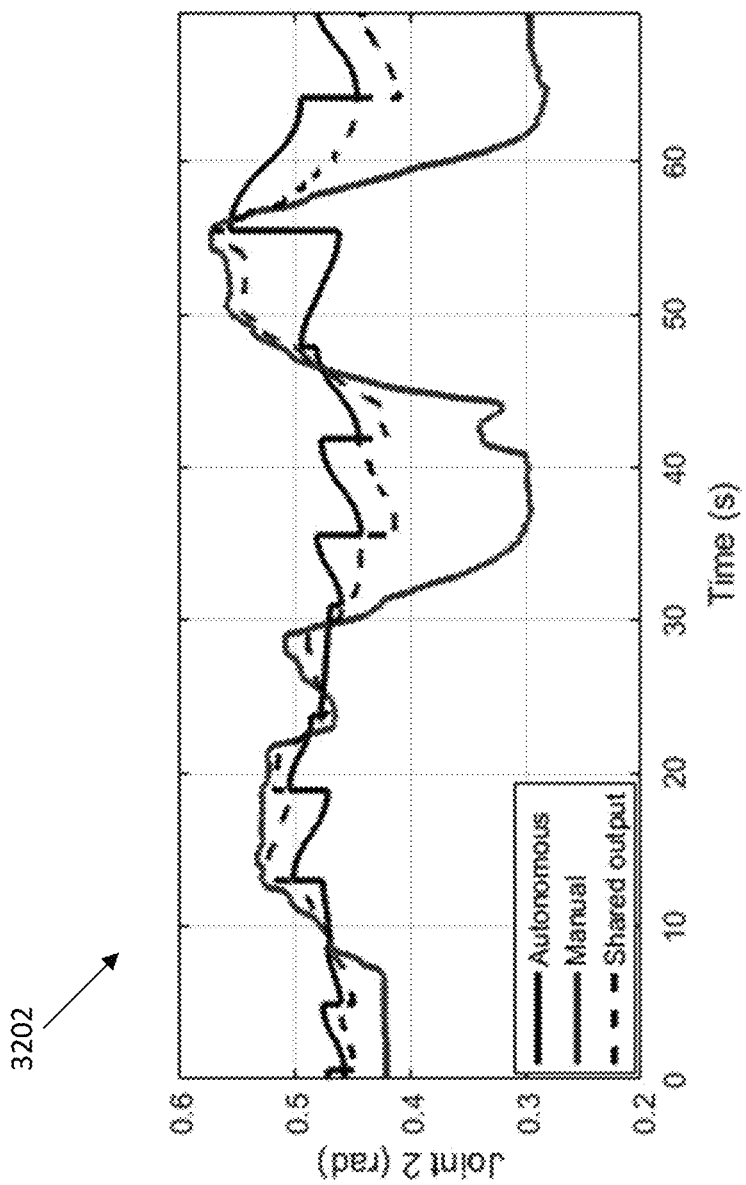
FIG. 32B shows an illustrative graph depicting a shared output for controlling a second joint of a robot of an RAS system compared to autonomous and manual control signals based on which the shared output is generated, in accordance with embodiments of the present disclosure.

FIG. 32B shows a graph 3202 illustrating autonomous and manual commands sent to the 2nd joint of the robot 20 and the overall shared output applied to the 2nd joint.

Figure 32C:
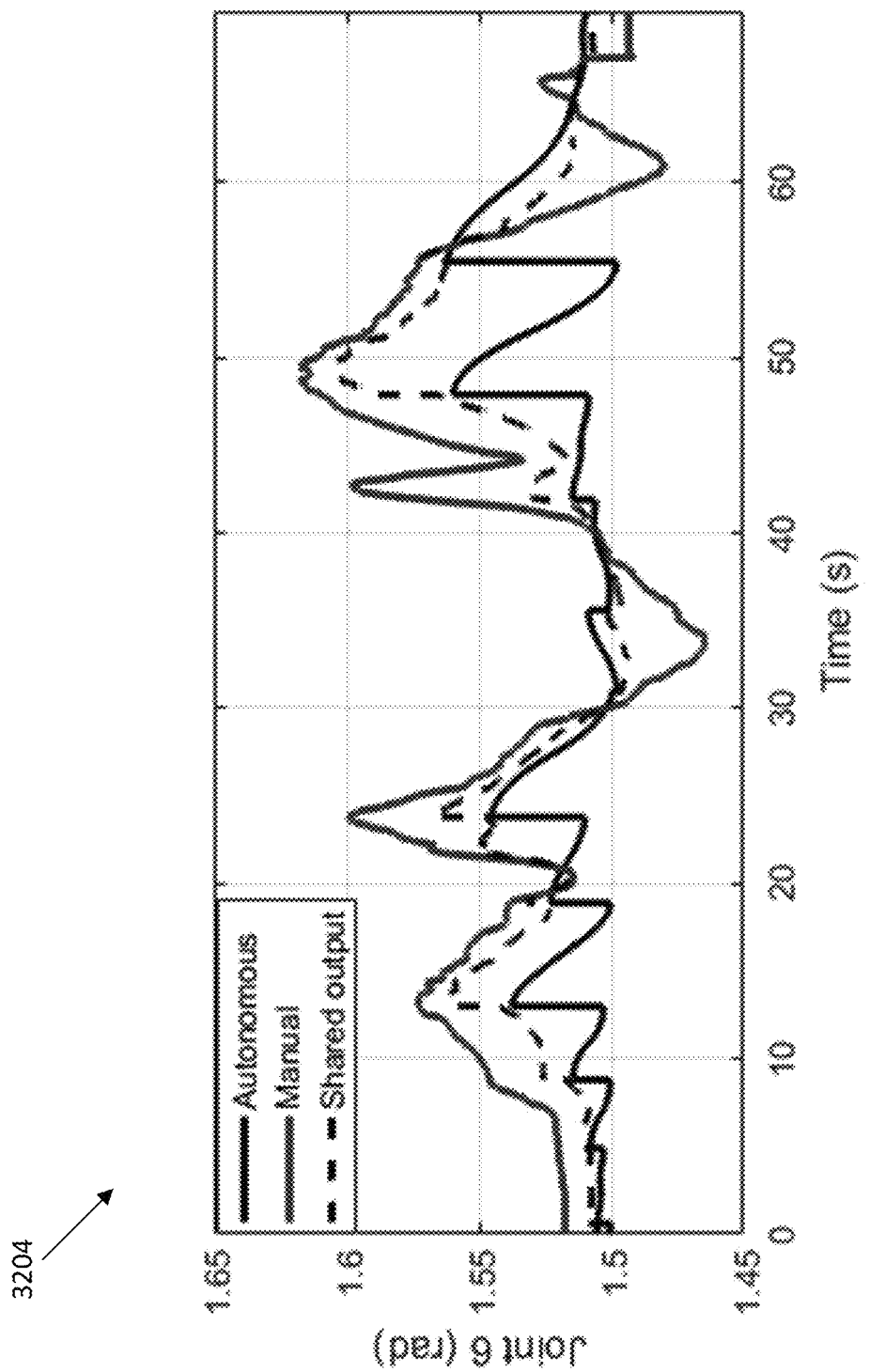
FIG. 32C shows an illustrative graph depicting a shared output for controlling a sixth joint of a robot of an RAS system compared to autonomous and manual control signals based on which the shared output is generated, in accordance with embodiments of the present disclosure.

FIG. 32C shows a graph 3204 illustrating autonomous and manual commands sent to the 6th joint of the robot 20 and the overall shared output applied to the 6th joint.

Figure 33:
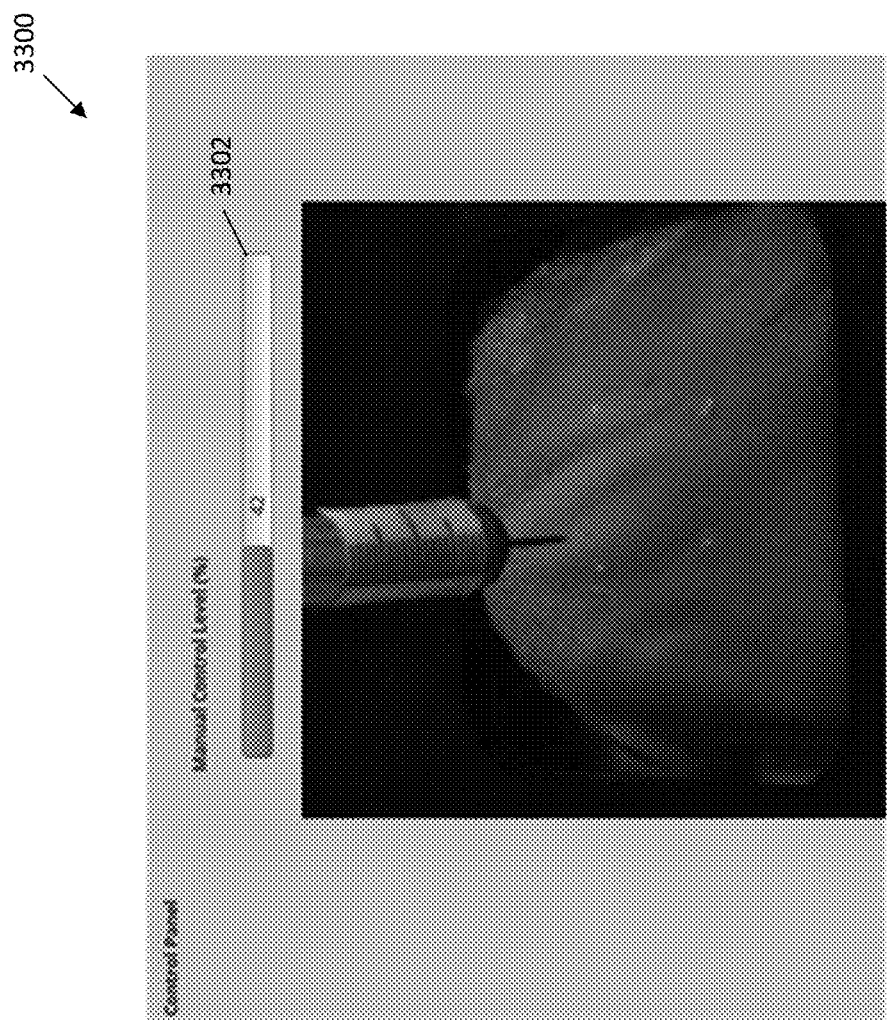
FIG. 33 illustrates a graphical user interface that includes an indicator of a level of shared control of the articulated member of a robot, in accordance with embodiments of the present disclosure.

FIG. 33 shows an illustrative user interface 3300 that may be displayed (e.g., via the monitor 1304 of FIG. 13) to the operator and that include 3302 an indicator depicting, in real-time or near-real-time, how much control the operator has over the robot (e.g., compared to the percentage of control that is being handled autonomously by the system 250).

Figure 34:
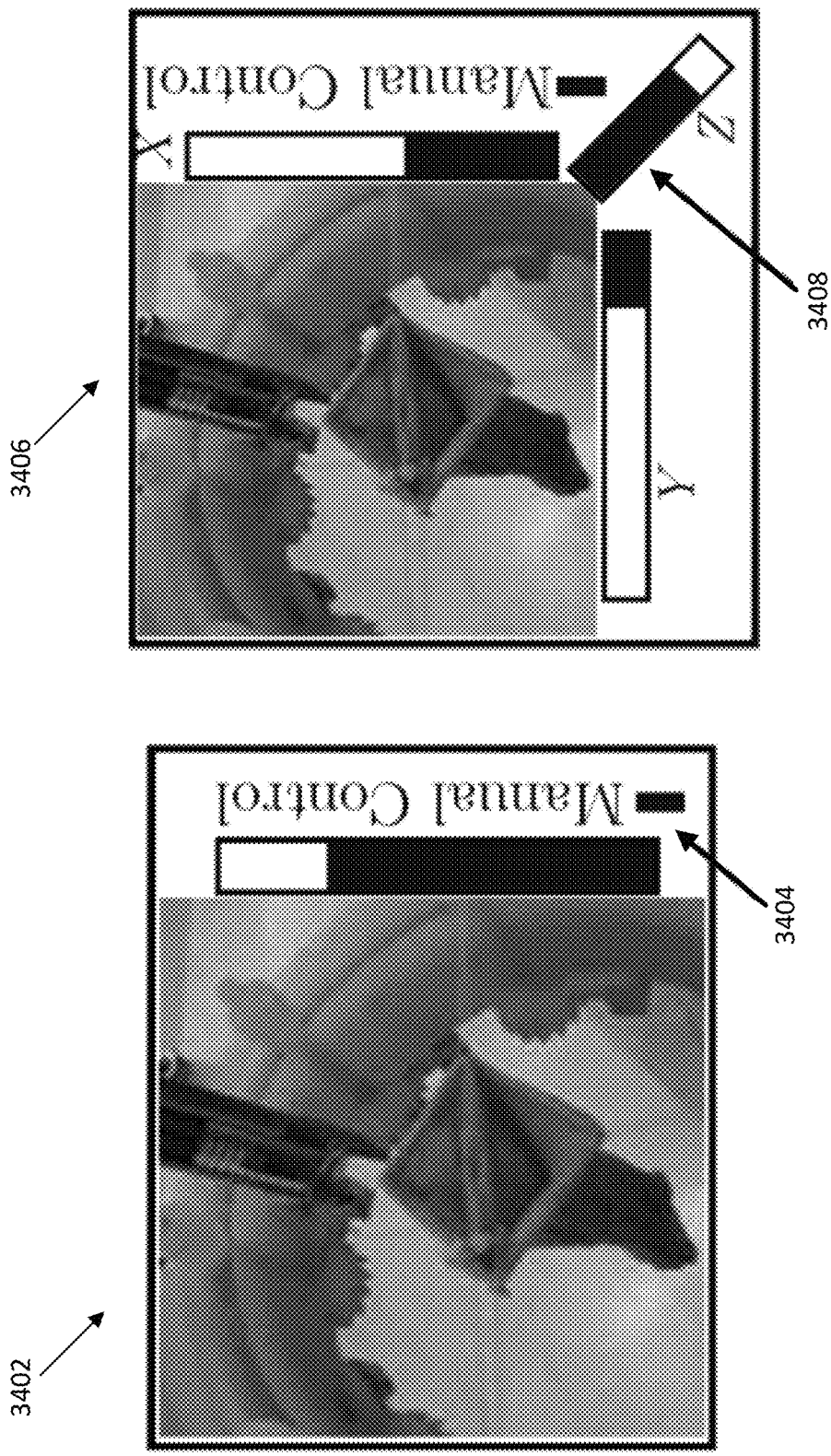
FIG. 34 illustrates a graphical user interface that includes manual control indicators for an RAS system, in accordance with embodiments of the present disclosure.
Figure 35:
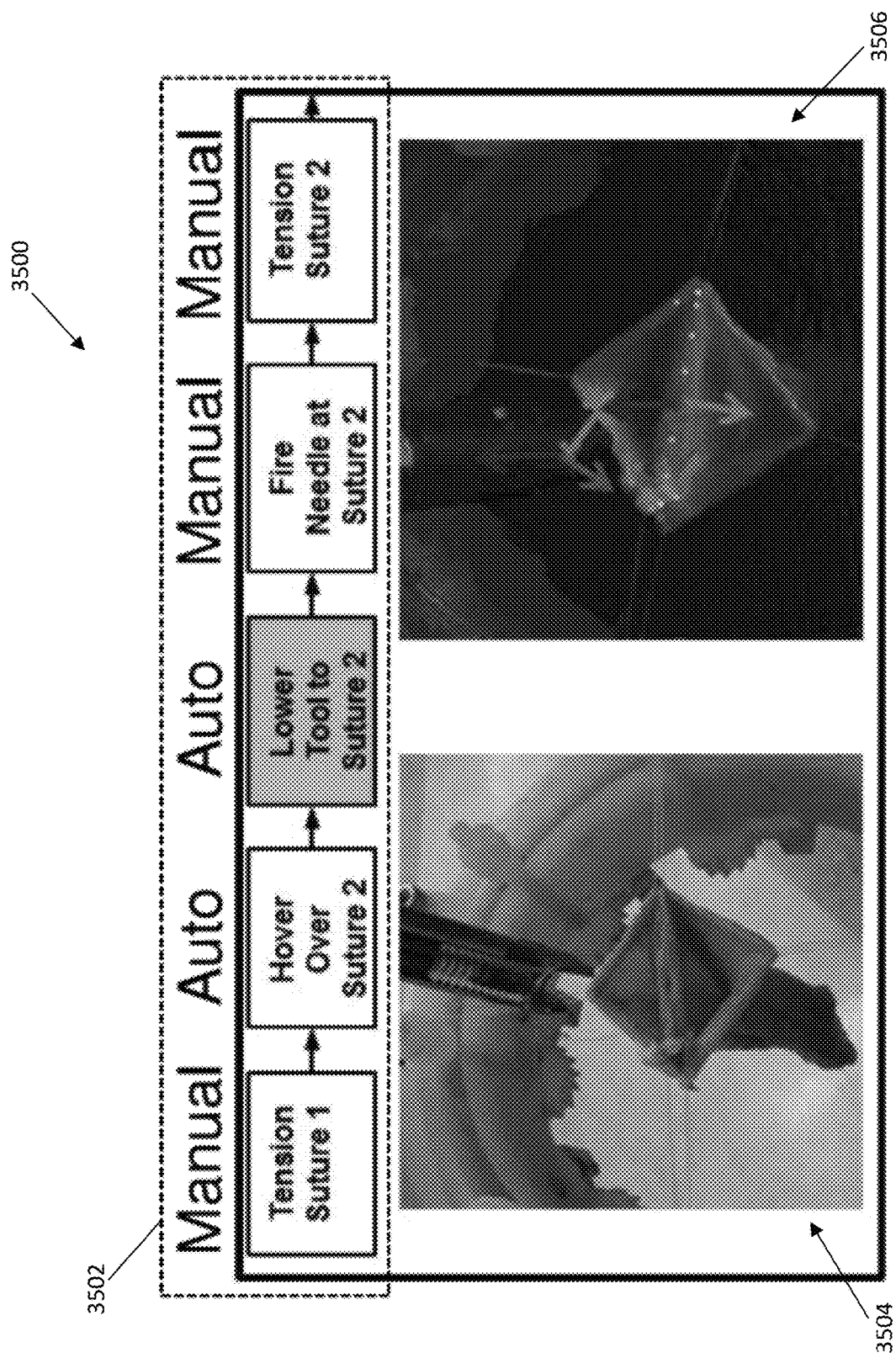
FIG. 35 illustrates a graphical user interface that includes regular and NIR video of a task space along with a procedure and control mode indicator corresponding to an RAS system, in accordance with embodiments of the present disclosure.

FIGS. 34 and 35 depict graphical user interfaces for RAS system 1100, (e.g., which may be displayed on the monitor 1304 of FIG. 13) in accordance with embodiments of the present disclosure. These GUIs are depicted for a suturing procedure.

As shown in FIG. 34, graphical user interface (GUI) 3402 depicts a video image of a task space (e.g., task space 2 of FIG. 16) and unidimensional control mode indicator 3404. A graphical user interface (GUI) 3406 depicts a video image of a task space (e.g., task space 2 of FIG. 16) and multidimensional control mode indicator 3408.

As shown in FIG. 35, a graphical user interface (GUI) 3500 depicts a visual video image 3504 of a task space (e.g., task space 2, FIG. 16), a NIR video image 3506 of the task space, and procedure and control mode indicator 3502.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," "for example," or the like) provided herein, is intended merely to better illuminate the embodiments and does not pose a limitation on the scope of the embodiments.

No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the preceding description, it is understood that terms such as "first," "second," "top," "bottom," "up," "down," "above," "below," and the like, are words of convenience and are not to be construed as limiting terms. Also, the terms apparatus, device, system, etc. may be used interchangeably in this text.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A system comprising:
   a camera system that includes a first camera and a second camera;
   an articulating member that includes a tool;
   a computer comprising:
      at least one processor; and
      a non-transitory memory configured to store computer-readable instructions which, when executed, cause the at least one processor to:
         receive image data from the first camera;
         receive point cloud image data from the second camera,
         wherein the image data and the point cloud image data correspond to a tissue on which markers are disposed;
         identify marker positions of the markers based on the image data and the point cloud image data;
         generate a path between a first point on the point cloud and a second point on the point cloud based at least on the marker positions;
         filter the path;
         receive real-time position data corresponding to the articulating member;
         generate a three-dimensional (3D) trajectory based on the filtered path and the real-time position data;
         generate control commands based on the 3D trajectory; and
         control the articulating member and the tool to follow the 3D trajectory based on the control commands.

2. The system of claim 1, wherein the tool comprises an electrocautery tool, and wherein the computer-readable instructions which cause the at least one processor to control the articulating member and the tool further cause the electrocautery tool to cut the tissue along the path.

3. The system of claim 1, wherein the first camera comprises a near-infrared (NIR) camera, wherein the second camera comprises a red-blue-green-depth (RGBD) camera, wherein the image data comprises NIR image data, and wherein the markers comprise NIR markers.

4. The system of claim 1, wherein the computer-readable instructions which cause the at least one processor to generate the path further cause the at least one processor to:
identify projected marker positions by applying an offsetting technique to project the marker positions outward on a point cloud of the point cloud image data; and
generate reference waypoints on the point cloud between two of the projected marker positions, such that the reference waypoints of the path are separate from the marker positions by at least a predetermined margin, wherein the path comprises the reference waypoints.

5. The system of claim 4, wherein the computer-readable instructions which cause the at least on processor to filter the path further cause the at least one processor to:
select tracked waypoints as a subset of the reference waypoints; and
generate filtered waypoints by applying a filtering algorithm to track the tracked waypoints.

6. The system of claim 5, wherein the filtering algorithm is selected from the group consisting of: a recursive least square algorithm, a Kalman filter, an extended Kalman filter, an unscented Kalman filter, and a particle filter.

7. The system of claim 1, wherein the computer-readable instructions, when executed, further cause the at least one processor to:
calculate at least one autonomous confidence indicator based on autonomous incision error;
calculate a manual confidence indicator based on manual incision error;
generate at least one allocation function based on the manual confidence indicator and the at least one autonomous confidence indicator; and
generate the control commands based on the at least one allocation function.

8. The system of claim 7, wherein the at least one autonomous confidence indicator is selected from the group consisting of: a roll angle confidence indicator which is generated based on roll angle error, a pitch angle confidence indicator which is generated based on pitch angle error, a distance confidence indicator which is generated based on distance error, and a density confidence indicator which is generated based on density error; and wherein the at least one allocation function comprises a plurality of allocation functions corresponding to movement of the articulating member in three-dimensional directions, and roll, pitch, and yaw of the articulated member.

9. A system, comprising:
an articulating member including a tool; and
a computer, coupled to the articulating member, including a processor configured to:
determine a first confidence indicator based on a manual control mode for the articulating member, wherein the first confidence indicator is based on first data acquired when the processor is operating in the manual control mode during a first performance of a predetermined task using the tool, and the first data include manual tracking error data associated with a first trajectory of the tool during the first performance of the predetermined task;
determine a second confidence indicator based on an autonomous control mode for the articulating member,
generate an allocation function based on the first confidence indicator and the second confidence indicator, and
generate a control command for the articulating member based on the allocation function.

10. The system of claim 9, further comprising a camera system that includes a first camera and a second camera, wherein the processor is further configured to:
receive image data from the first camera;
receive point cloud image data from the second camera, wherein the image data and the point cloud image data correspond to a tissue on which markers are disposed;
identify marker positions of the markers based on the image data and the point cloud image data;
generate a path between a first point on the point cloud and a second point on the point cloud based at least on the marker positions;
filter the path;
receive real-time position data corresponding to the articulating member;
generate a three-dimensional (3D) trajectory based on the filtered path and the real-time position data;
generate control commands based on the 3D trajectory; and
control the articulating member and the tool to follow the 3D trajectory based on the control commands.

11. The system of claim 9, wherein the second confidence indicator is based on second data acquired when the processor is operating in the autonomous control mode during a second performance of the predetermined task, and the second data include autonomous tracking error data associated with a second trajectory of the tool during the second performance of the predetermined task.

12. The system of claim 11, wherein, when the processor is operating in a shared control mode to perform the predetermined task using the tool, the processor is further configured to:
generate a manual control command for the articulating member based on input data received from an input device coupled to the processor;
generate an autonomous control command for the articulating member;
generate the control command based on the allocation function, the autonomous control command and the manual control command;
convert the control command into a robot-specific control signal; and
send the robot-specific control signal to the articulating member.

13. The system of claim 12, wherein the allocation function selects either the manual control command or the autonomous control command as the control command.

14. The system of claim 13, wherein the allocation function defines at least one decision threshold and determines which of the manual control command or the autonomous control command is selected as the control command.

15. The system of claim 12, wherein the control command is a combination of the manual control command and the autonomous control command, and the allocation function defines respective percentages of the manual control command and the autonomous control command.

16. The system of claim 12, wherein the processor is further configured to provide a graphical user interface (GUI) on a display coupled to the processor, the GUI including an image of a work space in which the predetermined task is performed, a desired trajectory of the tool for the predetermined task, at least one manual control mode region along the desired trajectory, and at least one autonomous control mode region along the desired trajectory.

17. The system of claim 16, wherein the processor is further configured to receive, from the input device, a user selection of either the manual control command or the autonomous control command as the control command.

18. The system of claim 11, wherein the predetermined task is a two-dimensional pattern cutting surgical task.

19. A method comprising:
generating image data and point cloud image data corresponding to a region of interest on which markers are disposed;
identifying marker positions of the markers based on the image data and the point cloud image data;
generating a path between a first point of the point cloud image data and a second point of the point cloud image data, based at least on the marker positions;
receiving real-time position data corresponding to an articulating member;
generating a three-dimensional (3D) trajectory for the articulating member based on the path and the real-time position data;
generating control commands based on the 3D trajectory; and
controlling the articulating member to follow the 3D trajectory based on the control commands.

20. A system comprising:
an articulating member including a tool;
a first camera;
a second camera; and
a computer, coupled to the articulating member, including a processor configured to:
determine a first confidence indicator based on a manual control mode for the articulating member;
determine a second confidence indicator based on an autonomous control mode for the articulating member,
generate an allocation function based on the first confidence indicator and the second confidence indicator,
generate a control command for the articulating member based on the allocation function;
receive image data from the first camera;
receive point cloud image data from the second camera, wherein the image data and the point cloud image data correspond to a tissue on which markers are disposed;
identify marker positions of the markers based on the image data and the point cloud image data;
generate a path between a first point on the point cloud and a second point on the point cloud based at least on the marker positions;
filter the path;
receive real-time position data corresponding to the articulating member;
generate a three-dimensional (3D) trajectory based on the filtered path and the real-time position data;
generate control commands based on the 3D trajectory; and
control the articulating member and the tool to follow the 3D trajectory based on the control commands.

* * * * *